United States Patent
Ray et al.

(10) Patent No.: US 9,074,253 B2
(45) Date of Patent: Jul. 7, 2015

(54) METHODS FOR DIAGNOSIS, PROGNOSIS AND TREATMENT OF PRIMARY AND METASTATIC BASAL-LIKE BREAST CANCER AND OTHER CANCER TYPES

(71) Applicant: JOHN WAYNE CANCER INSTITUTE, Santa Monica, CA (US)

(72) Inventors: Partha S. Ray, Los Angeles, CA (US); Sanjay Bagaria, Jacksonville, FL (US); Xiaojiang Cui, Pearland, TX (US); Jinhua Wang, Los Angeles, CA (US)

(73) Assignee: JOHN WAYNE CANCER INSTITUTE, Santa Monica, CA (US)

( * ) Notice: Subject to any disclaimer, the term of this patent is extended or adjusted under 35 U.S.C. 154(b) by 0 days.

(21) Appl. No.: 14/040,034

(22) Filed: Sep. 27, 2013

(65) Prior Publication Data

US 2014/0134626 A1    May 15, 2014

Related U.S. Application Data

(63) Continuation of application No. 12/852,453, filed on Aug. 7, 2010, now abandoned, which is a continuation of application No. PCT/US2010/044817, filed on Aug. 6, 2010.

(60) Provisional application No. 61/231,984, filed on Aug. 6, 2009.

(51) Int. Cl.
*C12Q 1/68* (2006.01)

(52) U.S. Cl.
CPC ............ *C12Q 1/6881* (2013.01); *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0058340 A1 | 3/2004 | Dai et al. |
| 2010/0166745 A1 | 7/2010 | Mather et al. |

FOREIGN PATENT DOCUMENTS

| | | |
|---|---|---|
| WO | WO2009/009739 | 1/2009 |

OTHER PUBLICATIONS

Carrivick, et al. (2006) "Identification of prognostic signatures in breast cancer microarray data using Bayesian techniques", Journal of the Royal Society: Interface, 3: 367-81.*
Ravdin, et al. (1992) "Prognostic Significance of Progesterone Receptor Levels in Estrogen Receptor-Positive Patients With Metastatic Breast Cancer Treated With Tamoxifen: Results from a Prospective Southwest Oncology Group Study", Journal of Clinical Oncology, 10(8): 1284-91.*
Lacroix (2006) "Significance, detection and markers of disseminated breast cancer cells", Endocrine-Related Cancer, 13: 1033-67.*
C. Sotiriou & C. Desmedt (2006) "Gene expression profiling in breast cancer", Annals of Oncology, 17(Supplement 10): x259-x262.*
Knudsen (2008) "Evaluation of the Branched-Chain DNA Assay for Measurement of RNA in Formalin-Fixed Tissues", Journal of Molecular Dynamics, 10(2): 169-76.*
Ray, et al. (May 20, 2009) "Role of FOXC1 in regulation of basal-like/triple negative breast cancer", Journal of Clinical Oncology, 27(15S, May 20 Supplement): ABSTRACT 11016.*
Akaike H. A new look at the statistical model identification. IEEE Trans Automatic Control 1974;19:716-23.
Akaogi K, Nakajima Y, Ito I, Kawasaki S, Oie SH, Murayama A et al (2009). KLF4 suppresses estrogen-dependent breast cancer growth by inhibiting the transcriptional activity of ERalpha. Oncogene 28: 2894-902.
Albergaria A, Paredes J, Sousa B, Milanezi F, Carneiro V, Bastos J et al (2009). Expression of FOXA1 and GATA-3 in breast cancer: the prognostic significance in hormone receptor-negative tumours. Breast Cancer Res 11: R40.
Andre F, Job B, Dessen P, et al. Molecular characterization of breast cancer with high-resolution oligonucleotide comparative genomic hybridization array. Clin Cancer Res 2009;15:441-51.
Aslakson CJ, Miller FR. Selective events in the metastatic process defined by analysis of the sequential dissemination of subpopulations of a mouse mammary tumor. Cancer Res 1992;52:1399-405.
Belguise K, Sonenshein GE (2007). PKCtheta promotes c-Rel-driven mammary tumorigenesis in mice and humans by repressing estrogen receptor alpha synthesis. *J Clin Invest* 117: 4009-21.
Berry FB, Saleem RA, Walter MA (2002). FOXC1 transcriptional regulation is mediated by N- and C-terminal activation domains and contains a phosphorylated transcriptional inhibitory domain. *J Biol Chem* 277: 10292-7.
Berry FB, Mirzayans F, Walter MA. Regulation of FOXC1 stability and transcriptional activity by an epidermal growth factor-activated mitogen-activated protein kinase signaling cascade. J Biol Chem 2006;281:10098-104.
Biswas DK, Shi Q, Baily S. Strickland I, Ghosh S, Pardee AB et al (2004). NF-kappa B activation in human breast cancer specimens and its role in cell proliferation and apoptosis. *Proc Natl Acad Sci U S A* 101: 10137-42.
Biswas DK, Singh S, Shi Q, Pardee AB, Iglehart JD (2005). Crossroads of estrogen receptor and NF-kappaB signaling. *Sci STKE* 2005: pe27.
Bland JM, Altman DG. Survival probabilities (the Kaplan-Meier method). BMJ. Dec. 5, 1998;317(7172):1572.

(Continued)

Primary Examiner — Robert M Kelly
(74) Attorney, Agent, or Firm — Perkins Coie LLP

(57) ABSTRACT

In one embodiment, a method of theranostic classification of a breast cancer tumor is provided, comprising obtaining a breast cancer tumor sample from a subject, detecting an expression level of FOXC1, comparing the expression level of FOXC1 to a predetermined cutoff level, and classifying the breast cancer tumor sample as belonging to a theranostic basal-like breast cancer tumor subtype or a theranostic hybrid basal-like breast cancer tumor subtype when the expression level of FOXC1 is higher than the predetermined cutoff level. In other embodiments, methods for predicting a prognosis of a basal-like breast cancer and methods of treating a basal-like breast cancer are provided.

2 Claims, 26 Drawing Sheets

(56) References Cited

OTHER PUBLICATIONS

Bloushtain-Qimron N, Yao J, Snyder EL, et al. Cell type-specific DNA methylation patterns in the human breast. Proc Natl Acad Sci U S A 2008;105:14076-81.

Carey LA, Perou CM, Livasy CA, et al. Race, breast cancer subtypes, and survival in the Carolina Breast Cancer Study. JAMA 2006;295:2492-502.

Carey LA, Dees, EC, Sawyer, L., et al. The Triple Negative Paradox: Primary Tumor Chemosensitivity of Breast Cancer Subtypes. Clin Cancer Res Apr. 15, 2001; 13; 8:2329-2334.

Carroll JS, Liu XS, Brodsky AS, Li W, Meyer CA, Szary AJ et al (2005). Chromosome-wide mapping of estrogen receptor binding reveals long-range regulation requiring the forkhead protein FoxA1. *Cell* 122: 33-43.

Charafe-Jauffret E, Monville F, Bertucci F, et al. Moesin expression is a marker of basal breast carcinomas. Int J Cancer 2007; 121: 1779-85.

Cheang MC, Voduc D, Bajdik C, Leung S, McKinney S, Chia SK, et al. Basal-like breast cancer defined by five biomarkers has superior prognostic value than triple-negative phenotype. Clin Cancer Res. Mar. 1, 2008;14(5):1368-76.

Couse JF, Korach KS (1999). Estrogen receptor null mice: what have we learned and where will they lead us? *Endocr Rev* 20: 358-417.

Cui X, Zhang P, Deng W, Oesterreich S, Lu Y, Mills GB et al (2003). Insulin-like growth factor-I inhibits progesterone receptor expression in breast cancer cells via the phosphatidylinositol 3-kinase/Akt/mammalian target of rapamycin pathway: progesterone receptor as a potential indicator of growth factor activity in breast cancer. *Mol Endocrinol* 17: 575-88.

deConinck EC, McPherson LA, Weigel RJ (1995). Transcriptional regulation of estrogen receptor in breast carcinomas. *Mol Cell Biol* 15: 2191-6.

Dent R, Trudeau M, Pritchard KI, et al. Triple-negative breast cancer: clinical features and patterns of recurrence. Clin Cancer Res 2007; 13:4429-34.

Dhasarathy A, Kajita M, Wade PA (2007). The transcription factor snail mediates epithelial to mesenchymal transitions by repression of estrogen receptor-alpha. *Mol Endocrinol* 21: 2907-18.

Eeckhoute J, Keeton EK, Lupien M, Krum SA, Carroll JS, Brown M (2007). Positive cross-regulatory loop ties GATA-3 to estrogen receptor alpha expression in breast cancer. *Cancer Res* 67: 6477-83.

Elsheikh SE, Green AR, Rakha EA, et al. Caveolin 1 and caveolin 2 are associated with breast cancer basal-like and triple-negative immunophenotype. Br J Cancer 2008;99:327-34.

Farmer P, Bonnefoi H, Becette V, et al. Identification of molecular apocrine breast tumours by microarray analysis. Oncogene 2005; 24:4660-71.

Fuqua SA, Schiff R, Parra I, Moore JT, Mohsin SK, Osborne CK et al (2003). Estrogen receptor beta protein in human breast cancer: correlation with clinical tumor parameters. Cancer Res 63: 2434-9.

Ginestier C, Cervera N, Finetti P, Esteyries S, Estemi B, Adelaide J et al (2006). Prognosis and gene expression profiling of 20q13-amplified breast cancers. *Clin Cancer Res* 12: 4533-44.

Gionet N, Jansson D, Mader S, Pratt MA (2009). NF-kappaB and estrogen receptor alpha interactions: Differential function in estrogen receptor-negative and -positive hormone-independent breast cancer cells. *J Cell Biochem* 107: 448-59.

Green S, Walter P, Kumar V, Krust A, Bornert JM, Argos P et al (1986). Human oestrogen receptor cDNA: sequence, expression and homology to v-erb-A. *Nature* 320: 134-9.

Guo S, Sonenshein GE (2004). Forkhead box transcription factor FOXO3a regulates estrogen receptor alpha expression and is repressed by the Her-2/neu/phosphatidylinositol 3-kinase/Akt signaling pathway. *Mol Cell Biol* 24: 8681-90.

Hasegawa M, Moritani S. Murakumo Y, et al. CD109 expression in basal-like breast carcinoma. Pathol Int 2008; 58: 288-94.

Herschkowitz JI, Simin K, Weigman VJ, et al. Identification of conserved gene expression features between murine mammary carcinoma models and human breast tumors. Genome Biol 2007;8:R76.

Hess KR, Anderson K, Symmans WF, et al. Pharmacogenomic predictor of sensitivity to preoperative chemotherapy with paclitaxel and fluorouracil, doxorubicin, and cyclophosphamide in breast cancer. J Clin Oncol 2006;24:4236-44.

Holloway JN, Murthy S, El-Ashry D (2004). A cytoplasmic substrate of mitogen-activated protein kinase is responsible for estrogen receptor-alpha down-regulation in breast cancer cells: the role of nuclear factor-kappaB. *Mol Endocrinol* 18: 1396-410.

Hosey AM, Gorski JJ, Murray MM, Quinn JE, Chung WY, Stewart GE et al (2007). Molecular basis for estrogen receptor alpha deficiency in BRCA1-linked breast cancer. *J Natl Cancer Inst* 99: 1683-94.

Hu Z, Fan C, Oh DS, et al. The molecular portraits of breast tumors are conserved across microarray platforms. BMC Genomics 2006; 7:96.

Ihemelandu CU, Leffall LD, Jr., Dewitty RL, Naab TJ, Mezghebe HM, Makambi KH, et al. Molecular breast cancer subtypes in premenopausal and postmenopausal African-American women: age-specific prevalence and survival. J Surg Res. Nov. 2007; 143(1):109-18.

Ihemelandu CU, Naab TJ, Mezghebe HM, Makambi KH, Siram SM, Leffall LD, Jr., et al. Treatment and survival outcome for molecular breast cancer subtypes in black women. Ann Surg. Mar. 2008;247(3):463-9.

International Search Report and Written Opinion for PCT/US10/44817 dated Aug. 6, 2010.

Ivshina AV, George J, Senko O, et al. Genetic reclassification of histologic grade delineates new clinical subtypes of breast cancer. Cancer Res 2006;66:10292-301.

Karin M, Cao Y, Greten FR, Li ZW (2002). NF-kappaB in cancer: from innocent bystander to major culprit. *Nat Rev Cancer* 2: 301-10.

Keen JC, Davidson NE (2003). The biology of breast carcinoma. *Cancer* 97: 825-33.

Korsching E, Jeffrey SS, Meinerz W, Decker T, Boecker W, Buerger H. Basal carcinoma of the'breast revisited: an old entity with new interpretations. J Clin Pathol 2008; 61: 553-60.

Kos M, Reid G, Denger S, Gannon F (2001). Minireview: genomic organization of the human ERalpha gene promoter region. *Mol Endocrinol* 15: 2057-63.

Kreike B, van Kouwenhove M, Horlings H, et al. Gene expression profiling and histopathological characterization of triple-negative/basal-like breast carcinomas. Breast Cancer Res 2007;9:R65.

Kuiper GG, Carlsson B, Grandien K, Enmark E, Haggblad J, Nilsson S et al (1997). Comparison of the ligand binding specificity and transcript tissue distribution of estrogen receptors alpha and beta. *Endocrinology* 138: 863-70.

Laganiere J, Deblois G, Lefebvre C, Bataille AR, Robert F, Giguere V (2005). From the Cover: Location analysis of estrogen receptor alpha target promoters reveals that FOXA1 defines a domain of the estrogen response. *Proc Natl Acad Sci U S A* 102: 11651-6.

Landis SH, Murray T, Bolden S, Wingo PA (1999). Cancer statistics, 1999. *CA Cancer J Clin* 49: 8-31, 1.

Lin Y, Bai L, Chen W, Xu S The NF-kappaB activation pathways, emerging molecular targets for cancer prevention and therapy. *Expert Opin Ther Targets* 14: 45-55.

Lin Z, Yin P, Reierstad S, O'Halloran M, Coon VJ, Pearson EK et al Adenosine A1 receptor, a target and regulator of estrogen receptoralpha action, mediates the proliferative effects of estradiol in breast cancer. Oncogene 29: 1114-22.

Livasy CA, Karaca G, Nanda R, et al. Phenotypic evaluation of the basal-like subtype of invasive breast carcinoma. Mod Pathol 2006; 19:264-71.

Lu S, Simin K, Khan A, Mercurio AM. Analysis of integrin beta4 expression in human breast cancer: association with basal-like tumors and prognostic significance. Clin Cancer Res 2008; 14: 1050-8.

Lu X, Wang ZC, Iglehart JD, Zhang X, Richardson AL (2008). Predicting features of breast cancer with gene expression patterns. *Breast Cancer Res Treat* 108: 191-201.

Lupien M, Eeckhoute J, Meyer CA, Wang Q, Zhang Y, Li W et al (2008). FoxA1 translates epigenetic signatures into enhancer-driven lineage-specific transcription. *Cell* 1132: 958-70.

(56) References Cited

OTHER PUBLICATIONS

Mahmoodzadeh S, Fritschka S, Dworatzek E, Pham TH, Becher E, Kuehne A et al (2009). Nuclear factor-kappaB regulates estrogen receptor-alpha transcription in the human heart. *J Biol Chem* 284: 24705-14.
Mani SA, Yang J, Brooks M, et al. Mesenchyme Forkhead 1 (FOXC2) plays a key role in metastasis and is associated with aggressive basal-like breast cancers. Proc Natl Acad Sci U S A 2007; 104: 10069-74.
McShane LM, Altman DG, Sauerbrei W, Taube SE, Gion M, Clark GM. REporting recommendations for tumour MARKer prognostic studies (REMARK). Br J Cancer. Aug. 22, 2005;93(4):387-91.
Miller LD, Smeds J, George J, et al. An expression signature for p53 status in human breast cancer predicts mutation status, transcriptional effects, and patient survival. Proc Natl Acad Sci U S A 2005; 102:13550-5.
Moyano JV, Evans JR, Chen F, et al. AlphaB-crystallin is a novel oncoprotein that predicts poor clinical outcome in breast cancer. J Clin Invest 2006; 116: 261-70.
Nakshatri H, Bhat-Nakshatri P, Martin DA, Goulet RJ, Jr., Sledge GW, Jr. (1997). Constitutive activation of NF-kappaB during progression of breast cancer to hormone-independent growth. *Mol Cell Biol* 17: 3629-39.
Nielsen TO, Hsu FD, Jensen K, et al. Immunohistochemical and clinical characterization of the basal-like subtype of invasive breast carcinoma. Clin Cancer Res 2004;10:5367-74.
Nishimura DY, Swiderski RE, Alward WL, Searby CC, Patil SR, Bennet SR et al (1998). The forkhead transcription factor gene FKHL7 is responsible for glaucoma phenotypes which map to 6p25. *Nat Genet* 19: 140-7.
Oh AS, Lorant LA, Holloway JN, Miller DL, Kern FG, El-Ashry D (2001). Hyperactivation of MAPK induces loss of ERalpha expression in breast cancer cells. *Mol Endocrinol* 15: 1344-59.
Osborne CK (1998). Steroid hormone receptors in breast cancer management. *Breast Cancer Res Treat* 51: 227-38.
Panomics. Quantigene FFPE. [online] 2006.
Park WC, Jordan VC (2002). Selective estrogen receptor modulators (SERMS) and their roles in breast cancer prevention. *Trends Mol Med* 8: 82-8.
Parker JS, Mullins M, Cheang MC, et al. Supervised risk predictor of breast cancer based on intrinsic subtypes. J Clin Oncol 2009; 27: 1160-7.
Pawitan Y, Bjohle J, Amler L, et al. Gene expression profiling spares early breast cancer patients from adjuvant therapy: derived and validated in two population-based cohorts. Breast Cancer Res 2005;7: R953-64.
Perou CM, Sorlie T, Eisen MB, et al. Molecular portraits of human breast tumours. Nature 2000;406:747-52.
Piva R, Bianchini E, Kumar VL, Chambon P, del Senno L (1988). Estrogen induced increase of estrogen receptor RNA in human breast cancer cells. *Biochem Biophys Res Commun* 155: 943-9.
Pollack JR, Sorlie T, Perou CM, Rees CA, Jeffrey SS, Lonning PE et al (2002). Microarray analysis reveals a major direct role 'of DNA copy number alteration in the transcriptional program of human breast tumors. *Proc Natl Acad Sci U S A* 99: 12963-8.
Qu Y, Wang J, Sim MS, Liu B, Giuliano A, Barsoum J et al (2009). Elesclomol, counteracted by Akt survival signaling, enhances the apoptotic effect of chemotherapy drugs in breast cancer cells. *Breast Cancer Res Treat.* 121:311-21.
Rakha EA, Elsheikh SE, Aleskandarany MA, Habashi HO, Green AR, Powe DG, et al. Triple-negative breast cancer: distinguishing between basal and nonbasal subtypes. Clin Cancer Res. Apr. 1, 2009;15(7):2302-10.
Rakha, E. A., et al. (2008) Basal-Like Breast Cancer: A Critical Review. J Clin Oncol May 20, 2008; vol. 26; No. 15: 2568-2581.
Ray P, Wang J, Qu Y, Sim M, Shamonki J, Bagaria SP et al (2010). FOXC1 Is a Potential Prognostic Biomarker with Functional Significance in Basal-like Breast Cancer, *Cancer Research* 2010; 70:3870-76.
Ray P, Wang J, Qu Y, Sim M, Shamonki J, Liu, B et al (2009). Role of FOXC1 in regulation of basal-like/triple-negative breast cancer. J Clin Oncol 2009 Annual Meeting Proceedings, 27: 15s.
Richardson AL, Wang ZC, De Nicolo A, et al. X chromosomal abnormalities in basal-like human breast cancer. Cancer Cell 2006:9:121-32.
Rosen EM, Fan S, Isaacs C (2005). BRCA1 in hormonal carcinogenesis: basic and clinical research. *Endocr Relat Cancer* 12: 533-48.
Ryo A, Suizu F, Yoshida Y, Perrem K, Liou YC, Wulf G et al (2003). Regulation of NF-kappaB signaling by Pint-dependent prolyl isomerization and ubiquitin-mediated proteolysis of p65/RelA. *Mol Cell* 12: 1413-26.
Saceda M, Grunt TW, Colomer R, Lippman ME, Lupu R, Martin MB (1996). Regulation of estrogen receptor concentration and activity by an erbB/HER ligand in breast carcinoma cell lines. *Endocrinology* 137: 4322-30.
Saleem RA, Banerjee-Basu S, Berry FB, Baxevanis AD, Walter MA (2003). Structural and functional analyses of disease-causing missense mutations in the forkhead domain of FOXC1. *Hum Mol Genet* 12: 2993-3005.
Sarrio D, Rodriguez-Pinilla SM, Hardisson D, Cano A, Moreno-Bueno G, Palacios J. Epithelial-mesenchymal transition in breast cancer relates to the basal-like phenotype. Cancer Res 2008;68:989-97.
Schuetz CS, Bonin M, Clare SE, Nieselt K, Sotlar K, Walter M et al (2006). Progression-specific genes identified by expression profiling of matched ductal carcinomas in situ and invasive breast tumors, combining laser capture microdissection and oligonucleotide microarray analysis. Cancer Res 66: 5278-86.
Seewaldt VL, Scott V. Images in clinical medicine. Rapid progression of basal-type breast cancer. N. Engl J Med 2007;356:e12.
Shirley SH, Rundhaug JE, Tian J, Cullinan-Ammann N, Lambertz I, Conti CJ et al (2009). Transcriptional regulation of estrogen receptor-alpha by p53 in human breast cancer cells. *Cancer Res* 69: 3405-14.
Singh S, Shi Q, Bailey ST, Palczewski MJ, Pardee AB, Iglehart JD et al (2007). Nuclear factor-kappaB activation: a molecular therapeutic target for estrogen receptor-negative and epidermal growth factor receptor family receptor-positive human breast cancer.*Mol Cancer Ther* 6: 1973-82.
Sorlie T, Perou CM, Tibshirani R, Aas T, Geisler S, Johnsen H et al (2001). Gene expression patterns of breast carcinomas distinguish tumor subclasses with clinical implications. *Proc Natl Acad Sci U S A* 98: 10869-74.
Sorlie T, Tibshirani R, Parker J, et al. Repeated observation of breast tumor subtypes in independent gene expression data sets. Proc Natl Acad Sci U S A 2003;100:8418-23.
Staaf J, Ringnér M, Vallon-Christersson J, Jönsson G, Bendahl PO, Holm K, Arason A, Gunnarsson H, Hegardt C, Agnarsson BA, Luts L, Grabau D, Fernö M, Malmstreöm PO, Johannsson OT, Loman N, Barkardottir RB, Borg A. Identification of subtypes in human epidermal growth factor receptor 2—positive breast cancer reveals a gene signature prognostic of outcome. J Clin Oncol. Apr. 10, 2010;28(11):1813-20.
Stein B, Yang MX (1995). Repression of the interleukin-6 promoter by estrogen receptor is mediated by NF-kappa B and C/EBP beta. *Mol Cell Biol* 15: 4971-9.
Tanimoto K, Eguchi H, Yoshida T, Hajiro-Nakanishi K, Hayashi S (1999). Regulation of estrogen receptor alpha gene mediated by promoter B responsible for its enhanced expression in human breast cancer. *Nucleic Acids Res* 27: 903-9.
Treilleux, Peloux N, Brown M, Sergeant A (1997). Human estrogen receptor (ER) gene promoter-P1: estradiol-independent activity and estradiol inducibility in ER+ and ER- cells. *Mol Endocrinol* 11: 1319-31.
van der Heul-Nieuwenhuijsen L, Dits NF, Jenster G (2009). Gene expression of forkhead transcription factors in the normal and diseased human prostate. *BJU Int* 103: 1574-80.
van de Vijver MJ, He YD, van't Veer U, et al. A gene-expression signature as a predictor of survival in breast cancer. N Engl J Med 2002; 347:1999-2009.

(56) References Cited

OTHER PUBLICATIONS

Van Laere SJ, Van der Auwera I, Van den Eynden GG, van Dam P, Van Merck EA, Vermeulen PB et al (2007). NF-kappaB activation in inflammatory breast cancer is associated with oestrogen receptor downregulation, secondary to EGFR and/or ErbB2 overexpression and MAPK hyperactivation. *Br J Cancer* 97: 659-69.

Wang Y, Klijn JG, Zhang Y, et al. Gene-expression profiles to predict distant metastasis of lymph-node-negative primary breast cancer. Lancet 2005;365:671-9.

Yaziji H, Goldstein LC, Barry TS, Werling R, Hwang H, Ellis GK, et al. HER-2 testing in breast cancer using parallel tissue-based methods. JAMA. Apr. 28, 2004;291(16):1972-7.

Yoshida T, Eguchi H, Nakachi K, Tanimoto K, Higashi Y. Suemasu K et al (2000). Distinct mechanisms of loss of estrogen receptor alpha gene expression in human breast cancer: methylation of the gene and alteration of trans-acting factors. *Carcinogenesis* 21: 2193-201.

Zhao H, Langerod A, Ji Y, Nowels KW, Nesland JM, Tibshirani R et al (2004). Different gene expression patterns in invasive lobular and ductal carcinomas of the breast. *Mol Biol Cell* 15: 2523-36.

Zhao JJ, Lin J, Yang H, Kong W, He L, Ma X et al (2008). MicroRNA-221/222 negatively regulates estrogen receptor alpha and is associated with tamoxifen resistance in breast cancer. *J Biol Chem* 283: 31079-86.

* cited by examiner

SEQUENCE LISTING

<160> NUMBER OF SEQ ID NOS: 14

<210> SEQ ID NO 1
<211> LENGTH: 57
<212> TYPE: DNA
<213> ORGANISM: Artificial Sequence
<220> FEATURE:
<223> OTHER INFORMATION: Mouse FoxC1 shRNA sequence

<400> SEQUENCE: 1
ccgggagcag agctactatc gcgctctcga gagcgcgata gtagctctgc tcttttg    57

<210> SEQ ID NO 2
<211> LENGTH: 58
<212> TYPE: DNA
<213> ORGANISM: Artificial Sequence
<220> FEATURE:
<223> OTHER INFORMATION: Mouse FoxC1 shRNA sequence

<400> SEQUENCE: 2
ccggtgggaa tagtagctgt cagatctcga gatctgacag ctactattcc cattttttg    58

<210> SEQ ID NO 3
<211> LENGTH: 58
<212> TYPE: DNA
<213> ORGANISM: Artificial Sequence
<220> FEATURE:
<223> OTHER INFORMATION: Human FoxC1 shRNA sequence

<400> SEQUENCE: 3
ccggcaagaa gaaggacgcg gtgaactcga gttcaccgcg tccttcttct tgtttttg    58

<210> SEQ ID NO 4
<211> LENGTH: 57
<212> TYPE: DNA
<213> ORGANISM: Artificial Sequence
<220> FEATURE:
<223> OTHER INFORMATION: Human FoxC1 shRNA sequence

<400> SEQUENCE: 4
ccggcccgga caagaagatc accctctcga gagggtgatc ttcttgtccg ggttttt    57

<210> SEQ ID NO 5
<211> LENGTH: 57
<212> TYPE: DNA
<213> ORGANISM: Artificial Sequence
<220> FEATURE:
<223> OTHER INFORMATION: Control shRNA

<400> SEQUENCE: 5
ccggcaacaa gatgaagagc accaactcga gttggtgctc ttcatcttgt tgttttt    57

<210> SEQ ID NO 6
<211> LENGTH: 25
<212> TYPE: DNA
<213> ORGANISM: Artificial Sequence
<220> FEATURE:
<223> OTHER INFORMATION: FOXC1 forward primer

<400> SEQUENCE: 6
cggtatccag ccagtctctg taccg    25

<210> SEQ ID NO 7
<211> LENGTH: 21
<212> TYPE: DNA
<213> ORGANISM: Artificial Sequence

```
<220> FEATURE:
<223> OTHER INFORMATION: FOXC1 reverse primer

<400> SEQUENCE: 7
gttcggcttt gagggtgtgt c                                              21

<210> SEQ ID NO 8
<211> LENGTH: 25
<212> TYPE: DNA
<213> ORGANISM: Artificial Sequence
<220> FEATURE:
<223> OTHER INFORMATION: FOXC1 ERalpha forward primer

<400> SEQUENCE: 8
cggttagatt catcatgcgg aaccg                                          25

<210> SEQ ID NO 9
<211> LENGTH: 21
<212> TYPE: DNA
<213> ORGANISM: Artificial Sequence
<220> FEATURE:
<223> OTHER INFORMATION: FOXC1 ERalpha reverse primer

<400> SEQUENCE: 9
tgtgtagagg gcatggtgga g                                              21

<210> SEQ ID NO 10
<211> LENGTH: 20
<212> TYPE: DNA
<213> ORGANISM: Artificial Sequence
<220> FEATURE:
<223> OTHER INFORMATION: ChIP assay ERalpha forward primer

<400> SEQUENCE: 10
agaagctaga cctctgcagg                                                20

<210> SEQ ID NO 11
<211> LENGTH: 21
<212> TYPE: DNA
<213> ORGANISM: Artificial Sequence
<220> FEATURE:
<223> OTHER INFORMATION: ChIP assay ERalpha reverse prime

<400> SEQUENCE: 11
aagcaggggc aaggaaatat c                                              21

<210> SEQ ID NO 12
<211> LENGTH: 3946
<212> TYPE: DNA
<213> ORGANISM: Artificial Sequence
<220> FEATURE:
<223> OTHER INFORMATION: FOXC1/FKHL7 gene
<300> PUBLICATION INFORMATION:
<308> DATABASE ACCESSION NUMBER: GenBank/AR140209
<309> DATABASE ENTRY DATE: 2001-06-16
<313> RELEVANT RESIDUES IN SEQ ID NO: (1)..(3946)

<400> SEQUENCE: 12
cgagaaaagg tgacgcgggg cccgggcagg cggccggcgc gcggccccccc cccccccgc    60 cctggttatt tggccgcctt cgccggcagc tcagggcaga gtctcctgga aggcgcaggc   120
agtgtggcga gaagggcgcc tgcttgttct ttcttttttgt ctgctttccc ccgtttgcgc  180
ctggaagctg cgccgcgagt tcctgcaagg cggtctgccg cggccgggcc cggccttctc   240
ccctcgcagc gaccccgcct cgcggccgcg cgggccccga ggtagcccga ggcgccggag   300
```

```
gagccagccc cagcgagcgc cgggagaggc ggcagcgcag ccggacgcac agcgcagcgg      360
gccggcacca gctcggccgg gcccggactc ggactcggcg gccggcgcgg cgcggcccgg      420
cccgagcgag ggtgggggc ggcgggcggc gcggggcggc ggcgagcggg ggccatgcag       480
gcgcgctact ccgtgtccag ccccaactcc ctgggagtgg tgccctacct cggcggcgag      540
cagagctact accgcgcggc ggccgcggcg ccggggggcg gctacaccgc catgccggcc      600
cccatgagcg tgtactcgca ccctgcgcac gccgagcagt accgggcgg catggcccgc       660 gcctacgggc cctacacgcc gcagccgcag cccaaggaca tggtgaagcc gccctatagc      720
tacatcgcgc tcatcaccat ggccatccag aacgccccgg acaagaagat caccctgaac      780
ggcatctacc agttcatcat ggaccgcttc cccttctacc gggacaacaa gcagggctgg      840
cagaacagca tccgccacaa cctctcgctc aacgagtgct tcgtcaaggt gccgcgcgac      900
gacaagaagc cgggcaaggg cagctactgg acgctggacc cggactccta caacatgttc      960
gagaacggca gcttcctgcg gcggcggcgg cgcttcaaga agaaggacgc ggtgaaggac     1020
aaggaggaga aggacaggct gcacctcaag gagccgcccc cgcccggccg ccagcccccg     1080
cccgcgccgc cggagcaggc cgacggcaac gcgcccggtc cgcagccgcc gcccgtgcgc     1140
atccaggaca tcaagaccga gaacggtacg tgccctcgc cgccccagcc cctgtccccg     1200
gccgccgccc tgggcagcgg cagcgccgcc gcggtgccca agatcgagag ccccgacagc     1260
agcagcagca gcctgtccag cgggagcagc ccccgggca gctgccgtc ggcgcggcc       1320 ctcagcctgg acgtgcggga ttccgcgccg ccgccgcccg cgccctccgc cccgccgccg     1380
caccatagcc agggcttcag cgtggacaac atcatgacgt cgctgcgggg gtcgccgcag     1440
agcgcggccg cggagctcag ctccggcctt ctggcctcgg cggccgcgtc ctcgcgcgcg     1500
gggatcgcac cccgctggc gctcggcgcc tactcgcccg ccagagctc cctctacagc       1560 tcccctgca gccagacctc cagcgcgggc agctcgggcg gcggcggcgg cggcgcgggg     1620
gccgcggggg gcgcgggcgg cgccgggacc taccactgca acctgcaagc catgagcctg     1680
tacgcggccg gcgagcgcgg gggccacttg cagggcgcgc ccggggggcgc gggcggctcg     1740 gccgtggaca cccccctgcc cgactactct ctgcctccgg tcaccagcag cagctcgtcg     1800
tccctgagtc acggcggcgg cggcggcggc ggcggggagg gccaggaggc cggccaccac     1860
cctgcggccc accaaggccg cctcacctcg tggtacctga accaggcggg cggagacctg     1920
ggccacttgg caagcgcggc ggcggcggcg gcggccgcag gctacccggg ccagcagcag     1980
aacttccact cggtgcggga gatgttcgag tcacagagga tcggcttgaa caactctcca     2040
gtgaacggga atagtagctg tcaaatggcc ttcccttcca gccagtctct gtaccgcacg     2100
tccggagctt tcgtctacga ctgtagcaag ttttgacaca ccctcaaagc cgaactaaat     2160
cgaaccccaa agcaggaaaa gctaaaggaa cccatcaagg caaaatcgaa actaaaaaaa     2220
aaaaatccaa ttaaaaaaaa cccctgagaa tattcaccac accagcgaac agaatatccc     2280
tccaaaaatt cagctcacca gcaccagcac gaagaaaact ctattttctt aaccgattaa     2340
ttcagagcca cctccacttt gccttgtcta aataaacaaa cccgtaaact gttttataca     2400
gagacagcaa aatcttggtt tattaaagga cagtgttact ccagataaca cgtaagtttc     2460
ttcttgcttt tcagagacct gctttcccct cctccgtct ccctctctt gccttcttcc      2520 ttgcctctca cctgtaagat attatttat cctatgttga agggaggggg aaagtccccg     2580
tttatgaaag tcgctttctt tttattcatg gacttgtttt aaaatgtaaa ttgcaacata    2640
gtaatttatt tttaatttgt agttggatgt cgtggaccaa acgccagaaa gtgttcccaa    2700
```

-continued

| | |
|---|---|
| aacctgacgt taaattgcct gaaactttaa attgtgcttt ttttctcatt ataaaaaggg | 2760 |
| aaactgtatt aatcttattc tatcctcttt tctttctttt tgttgaacat attcattgtt | 2820 |
| tgtttattaa taaattacca ttcagtttga atgagaccta tatgtctgga tactttaata | 2880 |
| gagctttaat tattacgaaa aaagatttca gagataaaac actagaagtt acctattctc | 2940 |
| cacctaaatc tctgaaaaat ggagaaaccc tctgactagt ccatgtcaaa ttttactaaa | 3000 |
| agtcttttg tttagattta ttttcctgca gcatcttctg caaaatgtac tatatagtca | 3060 |
| gcttgctttg aggctagtaa aaagatattt ttctaaacag attggagttg gcatataaac | 3120 |
| aaatacgttt tctcactaat gacagtccat gattcgaaaa ttttaagccc atgaatcagc | 3180 |
| cgcggtctta ccacggtgat gcctgtgtgc cgagagatgg gactgtgcgg ccagatatgc | 3240 |
| acagataaat atttggcttg tgtattccat ataaaattgc agtgcatatt atacatccct | 3300 |
| gtgagccaga tgctgaatag attttttcct attatttcag tcctttataa aaggaaaaat | 3360 |
| aaaccagttt ttaaatgtat gtatataatt ctcccccatt tacaatcctt catgtattac | 3420 |
| atagaaggat tgcttttttta aaaatatact gcgggttgga aagggatatt taatctttga | 3480 |
| gaaactattt tagaaaatat gtttgtagaa caattatttt tgaaaaagat ttaaagcaat | 3540 |
| aacaagaagg aaggcgagag gagcagaaca ttttggtcta gggtggtttc tttttaaacc | 3600 |
| attttttctt gttaatttac agttaaacct aggggacaat ccggattggc cctccccctt | 3660 |
| ttgtaaataa cccaggaaat gtaataaatt cattatctta gggtgatctg ccctgccaat | 3720 |
| cagactttgg ggagatggcg atttgattac agacgttcgg gggggtgggg ggcttgcagt | 3780 |
| ttgttttgga gataatacag tttcctgcta tctgccgctc ctatctagag gcaacactta | 3840 |
| agcagtaatt gctgttgctt gttgtcaaaa tttgatcatt gttaaaggat tgctgcaaat | 3900 |
| aaatacactt taatttcagt caaaaaaaaa aaaaaaaaa aaaaa | 3946 |

<210> SEQ ID NO 13
<211> LENGTH: 1659
<212> TYPE: DNA
<213> ORGANISM: Artificial Sequence
<220> FEATURE:
<223> OTHER INFORMATION: FOXC1/FKHL7 gene coding sequence
<300> PUBLICATION INFORMATION:
<308> DATABASE ACCESSION NUMBER: GenBank/AR140210
<309> DATABASE ENTRY DATE: 2001-06-16
<313> RELEVANT RESIDUES IN SEQ ID NO: (1)..(1659)

<400> SEQUENCE: 13

| | |
|---|---|
| atgcaggcgc gctactccgt gtccagcccc aactccctgg gagtggtgcc ctacctcggc | 60 |
| ggcgagcaga gctactaccg cgcggcggcc gcggcggccg ggggcggcta caccgccatg | 120 |
| ccggccccca tgagcgtgta ctcgcaccct gcgcacgccg agcagtaccc gggcggcatg | 180 |
| gcccgcgcct acgggcccta cacgccgcag ccgcagccca aggacatggt gaagccgccc | 240 |
| tatagctaca tcgcgctcat caccatggcc atccagaacg ccccgacaa gaagatcacc | 300 |
| ctgaacggca tctaccagtt catcatggac cgcttcccct tctaccggga caacaagcag | 360 |
| ggctggcaga acagcatccg ccacaacctc tcgctcaacg agtgcttcgt caaggtgccg | 420 |
| cgcgacgaca gaagccgggg caagggcagc tactggacgc tggaccccga ctcctacaac | 480 |
| atgttcgaga acggcagctt cctgcgcgcg cggcggcgct tcaagaagaa ggacgcggtg | 540 |
| aaggacaagg aggagaagga caggctgcac ctcaaggagc cgccccgcc cggccgccag | 600 |
| ccccccgccg cgccgccgga gcaggccgac ggcaacgcgc ccggtccgca gccgccgccc | 660 |

```
gtgcgcatcc aggacatcaa gaccgagaac ggtacgtgcc cctcgccgcc ccagcccctg    720
tccccggccg ccgccctggg cagcggcagc gccgccgcgg tgcccaagat cgagagcccc    780
gacagcagca gcagcagcct gtccagcggg agcagccccc cgggcagcct gccgtcggcg    840
cggccgctca gcctggacgg tgcggattcc gcgccgccgc cgcccgcgcc ctccgccccg    900
ccgccgcacc atagccaggg cttcagcgtg acaacatca tgacgtcgct gcggggtcg     960 ccgcagagcg cggccgcgga gctcagctcc ggccttctgg cctcggcggc cgcgtcctcg   1020 cgcgcggga tcgcaccccc gctggcgctc ggcgcctact cgcccggcca gagctccctc    1080
tacagctccc cctgcagcca gacctccagc gcgggcagct cgggcggcgg cggcggcggc   1140 gcggggcc cggggggcgc gggcggcgcc gggacctacc actgcaacct gcaagccatg     1200
agcctgtacg cggccggcga gcgcggggc cacttgcagg gcgcgccgg gggcgcgggc     1260 ggctcggccg tggacaaccc cctgcccgac tactctctgc tccggtcac cagcagcagc    1320 tcgtcgtccc tgagtcacgg cggcggcggc ggcggcggcg gggaggcca ggaggccggc    1380 caccaccctg cggcccacca aggccgcctc acctcgtggt acctgaacca ggcgggcgga   1440
gacctgggcc acttggcaag cgcggcggcg gcggcggcgg ccgcaggcta cccgggccag   1500
cagcagaact tccactcggt gcgggagatg ttcgagtcac agaggatcgg cttgaacaac   1560
tctccagtga acgggaatag tagctgtcaa atggccttcc cttccagcca gtctctgtac   1620
cgcacgtccg gagctttcgt ctacgactgt agcaagttt                          1659
```

<210> SEQ ID NO 14
<211> LENGTH: 553
<212> TYPE: PRT
<213> ORGANISM: Artificial Sequence
<220> FEATURE:
<223> OTHER INFORMATION: FOXC1/FKHL7 protein sequence
<300> PUBLICATION INFORMATION:
<308> DATABASE ACCESSION NUMBER: GenBank/AAE63616
<309> DATABASE ENTRY DATE: 2001-06-16
<313> RELEVANT RESIDUES IN SEQ ID NO: (1)..(553)

<400> SEQUENCE: 14

```
Met Gln Ala Arg Tyr Ser Val Ser Ser Pro Asn Ser Leu Gly Val Val
1               5                   10                  15

Pro Tyr Leu Gly Gly Glu Gln Ser Tyr Tyr Arg Ala Ala Ala Ala Ala
            20                  25                  30

Ala Gly Gly Gly Tyr Thr Ala Met Pro Ala Pro Met Ser Val Tyr Ser
        35                  40                  45

His Pro Ala His Ala Glu Gln Tyr Pro Gly Gly Met Ala Arg Ala Tyr
    50                  55                  60

Gly Pro Tyr Thr Pro Gln Pro Gln Pro Lys Asp Met Val Lys Pro Pro
65                  70                  75                  80

Tyr Ser Tyr Ile Ala Leu Ile Thr Met Ala Ile Gln Asn Ala Pro Asp
                85                  90                  95

Lys Lys Ile Thr Leu Asn Gly Ile Tyr Gln Phe Ile Met Asp Arg Phe
            100                 105                 110

Pro Phe Tyr Arg Asp Asn Lys Gln Gly Trp Gln Asn Ser Ile Arg His
        115                 120                 125

Asn Leu Ser Leu Asn Glu Cys Phe Val Lys Val Pro Arg Asp Asp Lys
    130                 135                 140

Lys Pro Gly Lys Gly Ser Tyr Trp Thr Leu Asp Pro Asp Ser Tyr Asn
145                 150                 155                 160

Met Phe Glu Asn Gly Ser Phe Leu Arg Arg Arg Arg Arg Phe Lys Lys
```

```
                    165                 170                 175
Lys Asp Ala Val Lys Asp Lys Glu Glu Lys Asp Arg Leu His Leu Lys
                180                 185                 190

Glu Pro Pro Pro Gly Arg Gln Pro Pro Ala Pro Pro Glu Gln
                195                 200                 205

Ala Asp Gly Asn Ala Pro Gly Pro Gln Pro Pro Val Arg Ile Gln
                210                 215                 220

Asp Ile Lys Thr Glu Asn Gly Thr Cys Pro Ser Pro Gln Pro Leu
225                 230                 235                 240

Ser Pro Ala Ala Ala Leu Gly Ser Gly Ser Ala Ala Val Pro Lys
                245                 250                 255

Ile Glu Ser Pro Asp Ser Ser Ser Ser Leu Ser Ser Gly Ser Ser
                260                 265                 270

Pro Pro Gly Ser Leu Pro Ser Ala Arg Pro Leu Ser Leu Asp Gly Ala
                275                 280                 285

Asp Ser Ala Pro Pro Pro Ala Pro Ser Ala Pro Pro His His
                290                 295                 300

Ser Gln Gly Phe Ser Val Asp Asn Ile Met Thr Ser Leu Arg Gly Ser
305                 310                 315                 320

Pro Gln Ser Ala Ala Ala Glu Leu Ser Ser Gly Leu Leu Ala Ser Ala
                325                 330                 335

Ala Ala Ser Ser Arg Ala Gly Ile Ala Pro Leu Ala Leu Gly Ala
                340                 345                 350

Tyr Ser Pro Gly Gln Ser Ser Leu Tyr Ser Ser Pro Cys Ser Gln Thr
                355                 360                 365

Ser Ser Ala Gly Ser Ser Gly Gly Gly Gly Gly Ala Gly Ala Ala
                370                 375                 380

Gly Gly Ala Gly Gly Ala Gly Thr Tyr His Cys Asn Leu Gln Ala Met
385                 390                 395                 400

Ser Leu Tyr Ala Ala Gly Glu Arg Gly Gly His Leu Gln Gly Ala Pro
                405                 410                 415

Gly Gly Ala Gly Gly Ser Ala Val Asp Asn Pro Leu Pro Asp Tyr Ser
                420                 425                 430

Leu Pro Pro Val Thr Ser Ser Ser Ser Ser Leu Ser His Gly Gly
                435                 440                 445

Gly Gly Gly Gly Gly Gly Gly Gln Glu Ala Gly His His Pro Ala
                450                 455                 460

Ala His Gln Gly Arg Leu Thr Ser Trp Tyr Leu Asn Gln Ala Gly Gly
465                 470                 475                 480

Asp Leu Gly His Leu Ala Ser Ala Ala Ala Ala Ala Ala Gly
                485                 490                 495

Tyr Pro Gly Gln Gln Gln Asn Phe His Ser Val Arg Glu Met Phe Glu
                500                 505                 510

Ser Gln Arg Ile Gly Leu Asn Asn Ser Pro Val Asn Gly Asn Ser Ser
                515                 520                 525

Cys Gln Met Ala Phe Pro Ser Ser Gln Ser Leu Tyr Arg Thr Ser Gly
                530                 535                 540

Ala Phe Val Tyr Asp Cys Ser Lys Phe
545                 550
```

METHODS FOR DIAGNOSIS, PROGNOSIS AND TREATMENT OF PRIMARY AND METASTATIC BASAL-LIKE BREAST CANCER AND OTHER CANCER TYPES

PRIORITY CLAIM

This application is a continuation of U.S. patent application Ser. No. 12/852,453, filed Aug. 7, 2010 and now pending, which is a continuation of International Application No. PCT/US10/44817, filed Aug. 6, 2010 and now expired, which claims priority to U.S. Provisional Patent Application No. 61/231,984, filed on Aug. 6, 2009, all of which are incorporated by reference as if fully set forth herein.

BACKGROUND

Diversity of molecular alterations, cellular compositions and clinical outcomes in cancer creates a major challenge in cancer treatment with respect to providing accurate diagnostic, prognostic, and predictive information. Tumors are typically described histopathologically using the tumor-node-metastasis (TNM) system. This system, which uses the size of the tumor, the presence or absence of tumor in regional lymph nodes, and the presence or absence of distant metastases, assigns a stage to the tumor as described by the American Joint Committee on Cancer (AJCC). The assigned stage is used as the basis for prognostication and for selection of appropriate therapy. However, this approach has many limitations. Tumors with similar TNM stage and histopathologic appearance can exhibit significant variability in terms of clinical course and response to therapy. For example, some tumors are very aggressive while others are not. Some tumors respond readily to hormonal therapy or chemotherapy while others are resistant.

The use of tumor biomarkers has provided an additional approach for dividing certain tumor types into subclasses. For example, one factor considered in prognosis and in treatment decisions for breast cancer is the presence or absence of the estrogen receptor (ER) in tumor samples. ER-positive breast cancers typically respond much more readily to hormonal therapies such as tamoxifen than ER-negative tumors. Though useful, this biomarker provides information for only a specific subset of breast cancers, leaving other subsets unaddressed.

Gene expression profiling has been successful in delineating specific breast cancer intrinsic molecular subtypes (Perou et al. 2000). This represents a significant advance in the understanding of breast cancer, the most commonly diagnosed cancer in women worldwide (Landis et al., 1999) and a disease that has proven to be quite heterogeneous in terms of its clinical presentation and features. Groups of breast cancer patients with distinct differences in their prognostic profiles have now been found to have equally distinct biologic and/or molecular profiles to help explain their associated clinical outcomes. This offers a tremendous opportunity to develop personalized therapeutics targeting the specific tumor biology associated with a specific molecular subtype of breast cancer. One particular molecular subtype that has garnered considerable interest is basal-like breast cancer (BLBC).

Although first reported more than 20 years ago on the basis of immunohistochemical (IHC) detection of basal cytokeratins (CK), this subtype again became notable after transcriptomic analysis of breast cancer confirmed its existence as a distinct molecular entity within breast cancer. While it differs substantially from the other delineated molecular subtypes in terms of its molecular makeup, the reason it has captured the attention of cancer biologists and clinicians alike is on account of its uniformly poor prognosis and lack of targeted therapy options. BLBC displays significant overlap with "triple-negative" breast cancer—a pathologic entity defined based on the absence of well-known breast cancer biomarkers estrogen receptor (ER), progesterone receptor (PR) and human epidermal growth factor receptor-2 (HER2). It is estimated that 60% to 90% of triple-negative breast cancers are BLBC. However BLBC is not synonymous with triple-negative breast cancer. Patients with BLBC are often younger, are more likely to be of African-American descent (Carey et al. 2006; Ihemelandu et al. 2007; Ihemelandu et al. 2008), are more likely to be BRCA1 mutation positive (Rakha et al. 2009), frequently develop distant metastatic disease to the brain and/or lung within 3-5 years of initial presentation (Wang et al. 2005) and have poor overall survival (Carey et al. 2006). In fact, the development of distant metastatic disease and subsequent death appears to be independent of initial presenting nodal status, as the majority of patients are lymph node negative at the time of initial diagnosis (Dent et al. 2007).

Currently the most effective biomarkers in routine clinical practice are theranostic biomarkers. Theranostic biomarkers provide information with respect to diagnosis (determination of the cancer biologic subtype), prognosis (determination of the clinical outcome) and therapeutic prediction (determination of therapeutic efficacy). Theranostic biomarkers are functionally most central and pivotal in the network of biomolecules that control the biology of their specific biologic subtype. Hence, targeted therapy directed towards a theranostic biomarker has a profound effect on clinical outcomes.

In breast cancer an example of a theranostic biomarker is ER. It accurately diagnoses "luminal" breast cancer patients (ER-positive), accurately prognosticates their outcome, and predicts their favorable response to tamoxifen, a drug that specifically targets ER. Prior to the introduction of tamoxifen therapy, ER-positive breast cancer patients had a poor prognosis. Their prognosis dramatically improved after therapy with tamoxifen became standard of care for such patients. Therefore, the most important component of a theranostic biomarker is the diagnosis it offers. Because with diagnosis comes prediction of therapeutic efficacy, which ultimately determines patient prognosis. While prognosis may change depending on advancements in therapy, the diagnosis of a biologic subtype, and therefore its target(s) for therapy will remain immutable. Moreover, the prognosis offered by a theranostic biomarker is more accurate than that offered by a non-theranostic biomarker. This is because theranostic biomarkers predict clinical outcomes that are very specific to the biology of the cancer subtype. For example, ER-positive status very specifically reflects the current favorable prognosis associated only with the luminal subtype because it takes into account subtype-specific treatment with anti-ER therapy (e.g. tamoxifen). Therefore, theranostic biomarkers offer superior prognosis.

Whole genome profiling technologies such as gene expression profiling (transcriptomics) have greatly expanded our knowledge of the genes and genetic pathways associated with the development and progression of cancer. Based on this knowledge, several commercialized multigene prognostic tests have entered the complex and expanding landscape of the cancer in vitro diagnostics (IVD) market. These tests contain many genes, only some of which indeed have critical functional importance to the survival and maintenance of the malignant phenotype. Such tests are unable to offer a refined understanding of the underlying biology of a specific subtype. In other words, the main drawback of such multigene prognostic tests is that they are not theranostic. They do not provide a diagnosis of a specific biologic subtype, and therefore they do not offer insight with regard to subtype-specific treatment. As a result, the prognostic value they offer is only an approximation across multiple subtypes. This is in contrast to a theranostic biomarker whose prognostic value is derived from a single subtype, and is therefore more precise and accurate.

Therefore the discovery and elucidation of theranostic biomarkers for BLBC and other cancers is important for the improvement of the classification of tumors and the treatment of cancer patients.

SUMMARY

In one embodiment, a method of theranostic classification of a breast cancer tumor is provided, the method comprising obtaining a breast cancer tumor sample from a subject, detecting an expression level of FOXC1, comparing the expression level of FOXC1 to a predetermined cutoff level, and classifying the breast cancer tumor sample as belonging to a theranostic basal-like breast cancer tumor subtype or a theranostic hybrid basal-like breast cancer tumor subtype when the expression level of FOXC1 is higher than the predetermined cutoff level.

In one embodiment, the method of theranostic classification of a breast cancer tumor may further comprise determining an expression status for estrogen receptor (ER), progesterone receptor (PR) and human epidermal growth factor receptor 2 (HER2) and classifying the breast cancer tumor sample as belonging to a theranostic hybrid basal-like/HER2+ breast cancer tumor subtype when the expression status of ER is negative (ER−), the expression status of PR is negative (PR−), the expression status of HER2 is positive (HER2+) and the expression level of FOXC1 is higher than the predetermined cutoff level.

In another embodiment, the method of theranostic classification of a breast cancer tumor may further comprise determining an expression status of ER, PR, and HER2 of the breast cancer tumor sample and classifying the breast cancer tumor sample as belonging to a theranostic hybrid basal-like/triple-negative breast cancer tumor subtype when the expression status of ER is negative (ER−), the expression status of PR is negative (PR−), the expression status of HER2 is negative (HER2−) and the expression level of FOXC1 is higher than the predetermined cutoff level.

In another embodiment, the method of theranostic classification of a breast cancer tumor may further comprise determining an expression status of ER, PR, and HER2 of the breast cancer tumor sample and classifying the breast cancer tumor sample as belonging to a theranostic hybrid basal-like/luminal breast cancer tumor subtype when the expression status of ER is positive (ER+), the expression status of PR is negative or positive (PR−/PR+), the expression status of HER2 is negative or positive (HER2−/HER2+) and the expression level of FOXC1 is higher than the predetermined cutoff level.

In one embodiment, a method for predicting a prognosis of a basal-like breast cancer is provided, the method comprising obtaining a breast cancer tumor sample from a subject, detecting an expression level of FOXC1, comparing the expression level of FOXC1 to a predetermined cutoff level, and predicting a poor prognosis of the basal-like breast cancer when the expression level of FOXC1 is higher than the predetermined cutoff level.

In some embodiments, the basal-like breast cancer is a hybrid basal-like/HER2+ breast cancer and the predetermined cutoff level is determined by a 50th percentile level of FOXC1 expression levels for a dataset of breast cancer tumors, the dataset comprising tumors having a HER2+ status.

In other embodiments, the basal-like breast cancer is a hybrid basal-like/luminal breast cancer and the predetermined cutoff level is determined by a 50th percentile level of FOXC1 expression levels for a dataset of breast cancer tumors, the dataset comprising tumors having an ER+ status.

In other embodiments, the basal-like breast cancer is a hybrid basal-like/triple-negative breast cancer and the predetermined cutoff level is determined by a 50th percentile level of FOXC1 expression levels for a dataset of breast cancer tumors, the dataset comprising tumors having an ER−/PR−/HER2− status.

In some embodiments, the prognosis is overall survival, recurrence free survival, a propensity of developing a distant metastasis, a time to a distant metastasis such as brain metastasis, a propensity for resistance to a targeted cancer therapy (e.g., trastuzumab (Herceptin®, tamoxifen or an aromatase inhibitor), wherein a propensity for resistance to a targeted cancer therapy may be a predictor of resistance or decreased efficacy.

In one embodiment, a method of treating a basal-like breast cancer is provided, the method comprising administering to a subject having a basal-like breast cancer a pharmaceutical composition, the composition comprising a pharmaceutically acceptable carrier and a therapeutically effective amount of a substance that inhibits FOXC1 expression and/or activity. In one embodiment, the basal-like breast cancer being treated is a hybrid basal-like/triple-negative breast cancer tumor subtype such as a hybrid basal-like/HER2+ breast cancer tumor subtype or hybrid basal-like/luminal breast cancer tumor subtype.

In one embodiment, the pharmaceutically acceptable carrier is a PEGylated immunoliposome that encapsulates the substance. In another embodiment, the substance is selected from the group consisting of an anti-FOXC1 antibody or functional fragment thereof, a small molecule or an anti-FOXC1 shRNA, siRNA or RNAi.

In some embodiments, the pharmaceutical composition further comprises a therapeutically effective amount of a substance that inhibits HER2 expression and/or activity such as trastuzumab (Herceptin®). In other embodiments, the pharmaceutical composition further comprises a therapeutically effective amount of a substance that inhibits ER expression and/or activity such as tamoxifen or an aromatase inhibitor.

DETAILED DESCRIPTION

Figure 1:
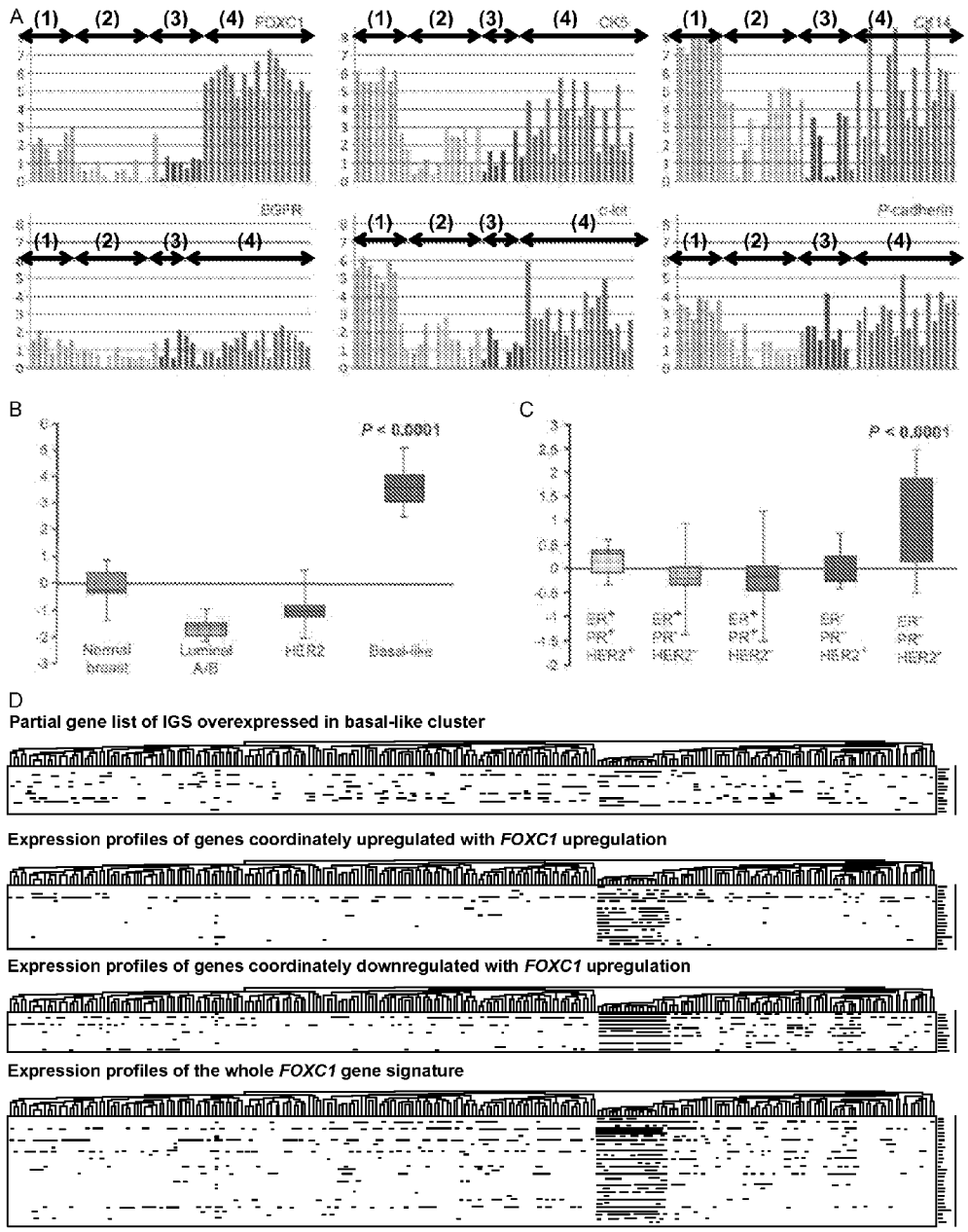
FIG. 1 shows differential expression of FOXC1 in human breast cancer subtypes. A, values of normalized signal intensity (baseline-to-zero-transformed) for basal-like subtype—associated genes from the Richardson et al. data set (Richardson et al. 2006). Numbers represent different subgroups: (1), normal; (2), luminal NB; (3), HER2; (4), basal-like. B, boxplot of FOXC1 values (normalized signal intensity) in normal breast tissue and luminal, HER2, and basal-like tumors of the same data set. Statistical significance was determined using ANOVA. C, boxplot of FOXC1 values from the Hess et al. data set with known ER, PR, and HER2 status (Hess et al. 2006). See FIG. 3 legends for description of boxplots. Statistical significance was determined using ANOVA. D, gene expression heat maps of the Ivshina et al. data set (Ivshina et al. 2006) hierarchically clustered by IGS display the expression profile of the FOXC1 signature.
Figure 2:
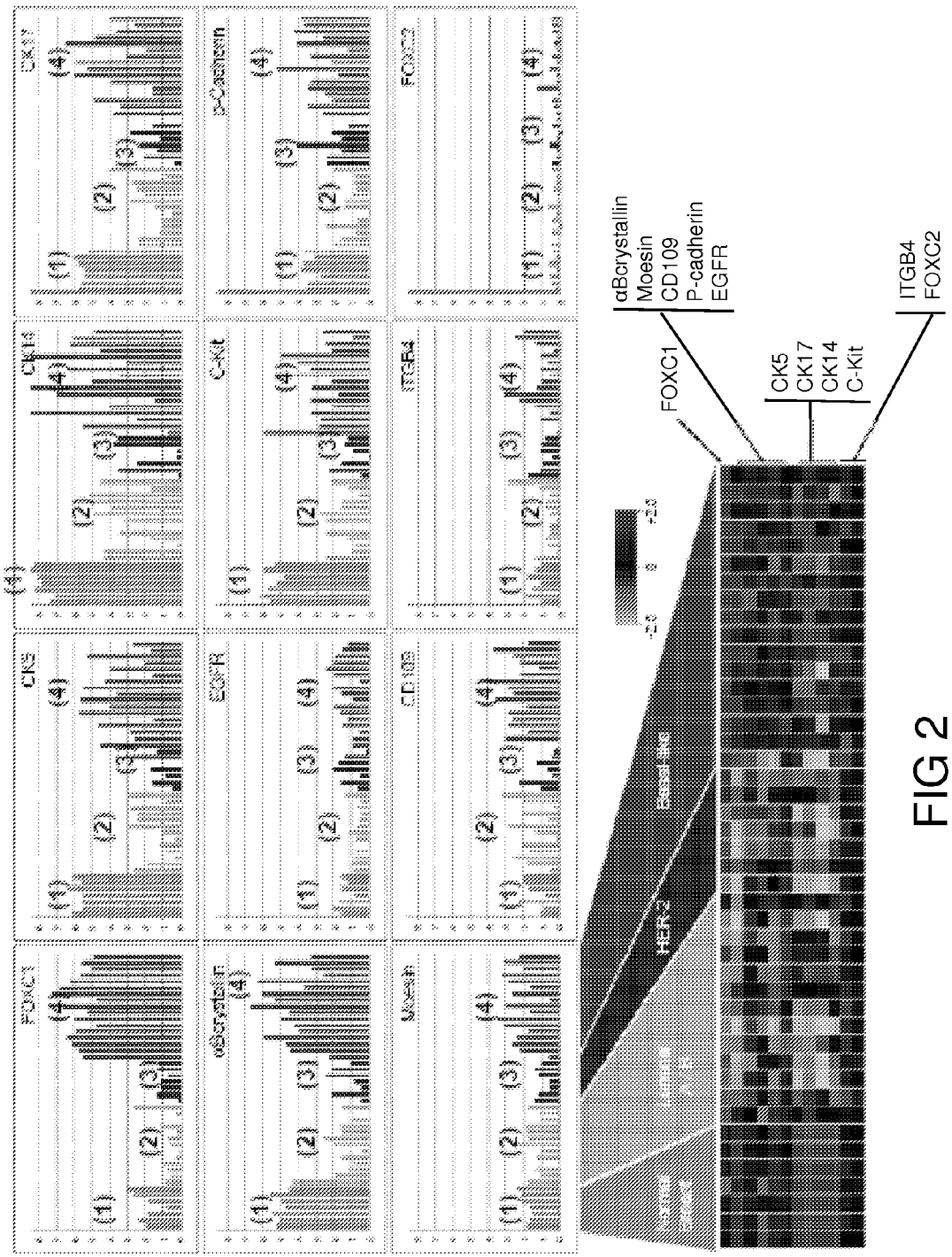
FIG. 2 shows differential expression of FOXC1 in human breast cancer subtypes. Values of normalized signal intensity for 12 reported basal-like markers from a representative dataset (Richardson et al. 2006) are presented. Numbers represent different subgroups: (1), normal; (2), luminal NB; (3), HER2; (4), Basal-like. The corresponding heat map is shown below.
Figure 3:
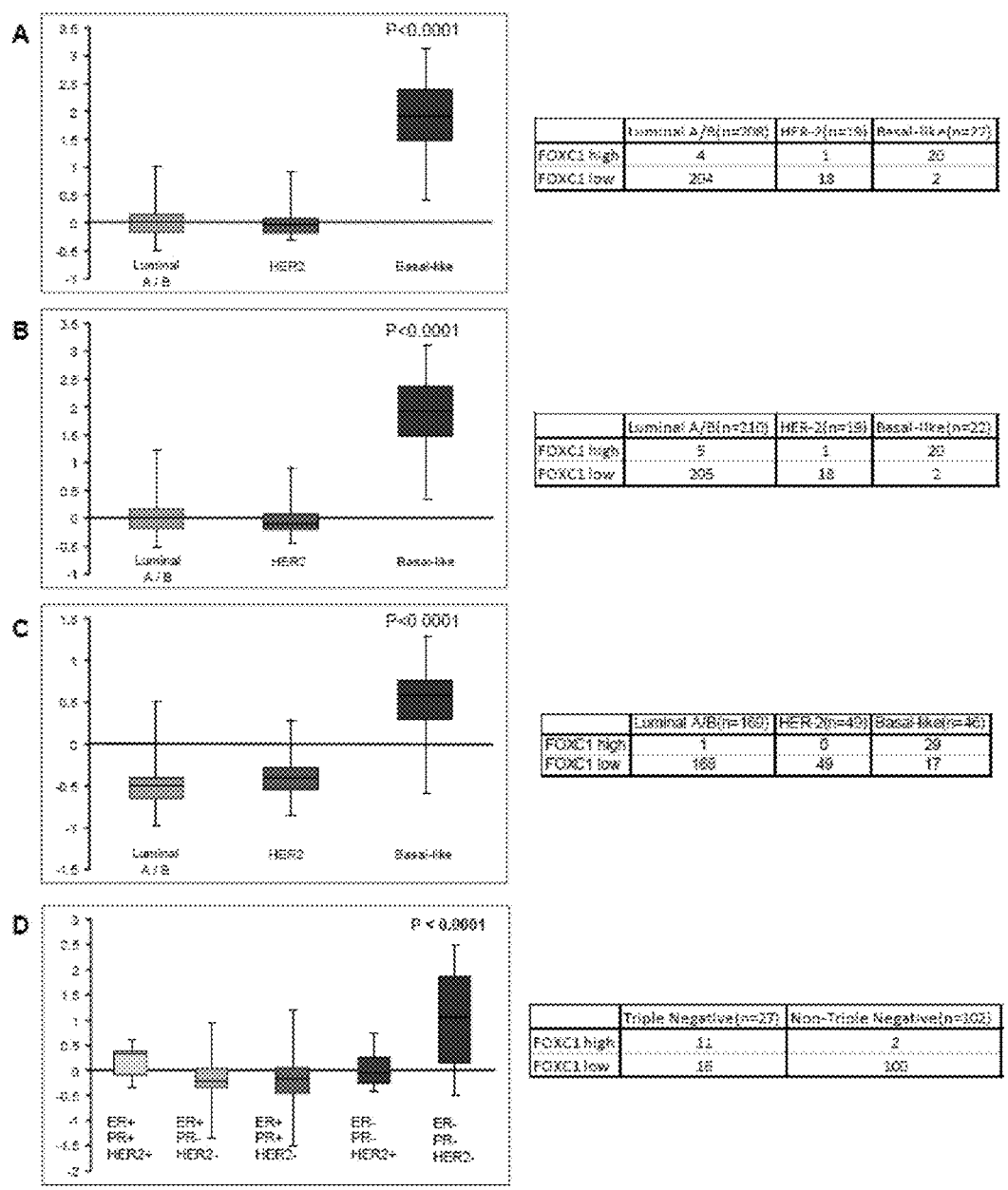
FIG. 3 shows differential expression of FOXC1 according to molecular subtypes or triple negative status. A. Boxplot of FOXC1 values (normalized signal intensity) in luminal NB, HER2, and basal-like tumors of the Ivshina et al. dataset (Ivshina et al. 2006). The line in the center of each box represents the median value of the distribution, and the upper and lower ends of the box are the upper ($75_{th}$) and lower ($25_{th}$) quartiles, respectively. The whiskers extend to the most extreme data point that is less than 1.5 times the interquartile range from the box. Statistical significance was determined using ANOVA. Table of FOXC1 high (>$90_{th}$ percentile) and FOXC1 low (<$90_{th}$ percentile) status versus molecular subtypes. Chi square P<0.0001. B. Boxplot of FOXC1 values (normalized signal intensity) in luminal A/B, HER2, and basal-like tumors of the Miller et al. dataset (Miller et al. 2005). Statistical significance was determined using ANOVA. Table of FOXC1 high (>$90_{th}$ percentile) and FOXC1 low (<$90_{th}$ percentile) status versus molecular subtypes. Chi square P<0.0001. C. Boxplot of FOXC1 values (normalized signal intensity) in luminal A/B, HER2, and basal-like tumors of the van de Vijver et al. dataset (van de Vijver et al. 2002). Statistical significance was determined using ANOVA. Table of FOXC1 high (>$90_{th}$ percentile) and FOXC1 low (<$90_{th}$ percentile) status versus molecular subtypes. Chi square P<0.0001. D. Boxplot of FOXC1 values (normalized signal intensity) in triple-negative and non-triple-negative tumors of the Hess et al. dataset (Hess et al. 2006). Statistical significance was determined using ANOVA. Table of FOXC1 high (>$90_{th}$ percentile) and FOXC1 low (<$90_{th}$ percentile) status versus triple-negative status. Chi square P<0.0001.

A method for classifying a tumor using a theranostic biomarker with independent prognostic significance is provided herein. A theranostic biomarker provides information relevant to diagnosis, prognosis and treatment of cancer in a subject. Although the present disclosure focuses on methods related to breast cancer in humans, the methods described herein may be applied to any cancer having one or more biomarkers with independent prognostic significance in any subject susceptible to developing breast cancer.

The term "theranostic biomarker" or a "theranostic classification" as used herein means a particular biomarker or classification that, in addition to providing significant diagnostic and prognostic information, also provides information useful in optimizing treatment of a subject having a disease such as cancer. The embodiments described herein provide a theranostic approach to classifying, diagnosing, prognosing and treating cancer. In practical terms, this means that a theranostic biomarker or theranostic classification can identify which subjects and which tumors are most suited to a particular therapy, and also provides feedback on the efficacy of a drug in order to demonstrate or determine how well a drug should work or does work to optimize therapy or therapy regimens. It can also identify which subjects are resistant to particular therapy or therapy regimens.

In one embodiment, the theranostic biomarker may be specific to a disease, such as breast cancer, or may be a general disease biomarker. In one embodiment, the theranostic biomarker is FOXC1. FOXC1 may be used as an independent theranostic biomarker, or may be used in conjunction with other molecular biomarkers that are relevant to a particular type of tumor or cancer. In one embodiment, FOXC1 may be used alone or in conjunction with estrogen receptor (ER), progesterone receptor (PR) and human epidermal growth factor receptor 2 (HER2; also known as ErBb2 mer-2/Neu) status for use in a method for theranostic classification, diagnosis, prognosis and treatment breast cancer and its subtypes. In some embodiments, such methods are useful in distinguishing between basal-like breast cancer subtypes, including hybrid basal-like breast cancer subtypes that exhibit both basal-like breast cancer characteristics and one or more characteristics of another subtype such as luminal or HER2-enriched.

In one embodiment, the methods described herein include providing or obtaining a tumor tissue sample. The tumor tissue sample may be a fresh frozen tumor sample, a formalin-fixed paraffin-embedded (FFPE) sample, a primary cell culture, or any other suitable tissue for determining an expression level of a biomaker. In one embodiment, the tumor tissue sample is a breast cancer tumor tissue sample.

In some embodiments, an expression level of a theranostic biomarker such as FOXC1 in a tumor tissue sample may be determined by qualitative or quantitative methods such as immunohistochemistry (IHC) or immunocytochemistry (ICC), non-quantitative or quantitative reverse transcription polymerase chain reaction (RT-PCR or qRT-PCR), protein or cDNA microarray or by a QuantiGene® assay (Panomics). The expression level may be a measurement of mRNA expression or protein expression. Data thus derived may be used to develop a cutoff expression level or a numerical prognostic index FOXC1 Score™ to aid in the clinical prognostic stratification of specific subsets of patients with breast cancer (and/or other cancers including but not limited to, melanoma, neuroendocrine tumors, brain tumors such as glioblastoma multiforme, astrocytoma and other brain cancers, renal cell cancer, sarcomas (such as synovial sarcoma) and leukemia. The numerical prognostic index FOXC1 Score™ may be calculated from a standard curve as generated by plotting qRT-PCR values of FOXC1 mRNA expression against a specific clinical outcome measure such as overall survival (OS), breast-cancer specific survival, recurrence free survival, matastasis-free survival, other suitable prognostic or outcome measures. The numerical prognostic index FOXC1 Score™ may be used for determining a subject's prognosis and may also be used for clinical management purposes for tracking the efficacy or optimizing the efficacy of one or more therapy regimens.

Breast Cancer Subtype Molecular Classification

Molecular classification of breast cancer has identified specific subtypes, often called "intrinsic" subtypes, with clinical and biological implications, including an intrinsic luminal subtype, an intrinsic HER2-enriched subtype (also referred to as the HER2$^+$ or ER$^-$/HER2$^+$ subtype) and an intrinsic basal-like breast cancer (BLBC) subtype. (Perou et al. 2000). Identification of the intrinsic subtypes has typically been accomplished by a combination of methods, including (1) histopathological detection, (2) ER, PR and HER2 expression status and (3) detection of characteristic cellular markers.

Basal-like breast cancer, which expresses genes characteristic of basal epithelial cells in the normal mammary gland, comprises up to 15%-25% of all breast cancers (Kreike et al. 2007) and is associated with the worst prognosis of all breast cancer types. BLBCs underexpress estrogen receptor (ER$^-$), progesterone receptor (PR$^-$), and human epidermal growth factor receptor 2 (HER2$^-$) and encompass 60% to 90% of so-called "triple-negative" (ER$^-$/PR$^-$/HER2$^-$) breast cancers. Although most basal-like breast cancers are often referred to as triple-negative based on the expression status of ER, PR and HER2, not all basal-like breast cancers are triple negative. Thus, the intrinsic basal-like breast cancer subtype may be further subdivided into at least three distinct subtypes described herein as "hybrid" basal-like breast cancer subtypes. In addition to a hybrid triple-negative subtype, the hybrid basal-like breast cancer subtypes have profiles that resemble both basal-like breast cancer and at least one other breast cancer molecular subtype. For example, hybrid basal-like subtypes can include a hybrid basal-like/HER2$^+$ subtype that has a receptor profile of ER$^-$/PR$^-$/HER$^+$, a hybrid basal-like/luminal subtype that has a receptor profile of ER$^+$/PR$^{-or+}$/HER$^{-or+}$, and a hybrid basal-like/triple negative subtype that has a receptor profile of ER⁻/PR⁻/HER⁻. The existence and significance of these hybrid basal-like subtypes has not previously been recognized, but because they represent some of the most aggressive and resistant to treatment subtypes of breast cancer, the methods described herein are important to improving the diagnosis, prognosis and treatment of this disease. The term "basal-like breast cancers," "basal-like subtypes," "basal-like tumors," "BLBCs" or the like as used herein is meant to encompass all cancers and tumors that exhibit characteristics of the BLBC subtype, including the intrinsic BLBC subtype, the hybrid triple-negative BLBC subtype, and any other hybrid basal-like subtypes described herein that may display markers that are associated with the luminal, HER+ or other previously classified subtype.

The intrinsic HER2-enriched subtype (also described as the HER2⁺ or ER⁻/HER2⁺ subtype) is characterized by underexpression of the hormone receptors ER and PR and overexpression of HER2 (ER⁻/PR⁻/HER2⁺). The HER2-enriched subtype is associated with a poor prognosis.

The intrinsic luminal breast cancer subtype is characterized by expression or overexpression of ER and/or PR (ER⁺ and/or PR⁺). The luminal subtype can be further subdivided based on HER2 status into the luminal A subtype, which is additionally characterized by underexpression of HER2 (ER⁺/PR⁺$^{or-}$/HER⁻), and luminal B subtype, which is additionally characterized by overexpression of HER2 (ER⁺/PR⁺$^{or-}$/HER⁺). Intrinsic luminal subtypes are often considered to be the most treatable breast cancer subtype and are associated with the best prognosis.

Whereas ER and HER2 guide treatment of luminal and HER2 breast cancers, respectively, chemotherapy remains the only modality of systemic therapy for BLBC. Preferentially affecting younger women, particularly African American women, BLBCs are associated with high histologic grade, aggressive clinical behavior, and a high rate of metastasis to the brain and lung (Carey et al. 2006). Unlike other breast cancer subtypes, there seems to be no correlation between tumor size and lymph node metastasis in BLBCs (Dent et al. 2007). Better understanding of the signaling pathways, biologic basis, and molecular mechanisms of basal-like, triple-negative breast cancer and other hybrid basal-like subtypes described above allows identification of accurate biomarkers for early diagnosis, prognosis, and targeted therapy.

BLBCs are associated with expression of basal cytokeratins (CK5/6, CK14, and CK17), epidermal growth factor receptor (EGFR), c-kit, and p53 and associated with the absence of ER, PR, and HER2 expression. With a large variety of associated genes, BLBCs have been defined differently in different studies using a set of diagnostic markers. For example, Nielsen et al. defined BLBC on the basis of negative ER and negative HER2 expression in addition to positive basal cytokeratin, EGFR, and/or c-kit expression (Nielsen et al. 2004). On the other hand, other groups have defined BLBC on the basis of on a combination of negative ER, and negative HER2 expression and positive CK5, P-cadherin, and p63 expression (Elsheikh et al. 2008) or positive vimentin, EGFR, and CK5/6 expression (Livasy et al. 2006). These different technical approaches in combination with widely varying patient cohorts may explain the inconsistent experimental results for these markers.

Identification of the basal-like subtype using immunohistochemistry (IHC) for detecting hormone receptors alone is less desirable than detecting a theranostic biomarker, because identification is based on the absence of IHC staining for estrogen receptor (ER), progesterone receptor (PR), and human epidermal growth factor receptor 2 (HER2) rather than the presence of a specific tumor marker or markers. Its diagnosis is more one of exclusion rather than inclusion. Basal-like breast cancer is often synonymously referred to as "triple negative" (i.e., ER⁻/PR⁻/HER2⁻), however, not all triple negative breast cancers are basal-like, and not all basal-like breast cancers are triple negative. Although other molecular markers have been associated with basal-like breast cancer as described above, such markers are not exclusive to this basal-like breast cancer and are therefore are not suitable for use as stand-alone markers. The best hope for a realistic, potentially objective, and convenient method to identify basal-like cancers in clinical practices would be through the positive detection of a definitive molecular marker or markers. Identification of FOXC1 as a dominant regulator of the basal-like phenotype may provide a pragmatic approach to distinguish this subgroup of breast cancer in clinical diagnosis, ultimately resulting in improved survival.

FOXC1 as a Biomarker for Basal-Like Breast Cancer

As described in the examples below, specific biomarkers for BLBC were identified and systemically analyzed using a 306-member intrinsic gene set (IGS) (Hu et al. 2006) in addition to other reported individual markers for BLBC using multiple microarray data sets. Degree of correlation of each individual gene with the basal-like subtype based on mRNA expression was used to identify genes highly specific to BLBC. The FOXC1 transcription factor emerged as a top-ranking gene. Therefore, diagnostic and prognostic significance of FOXC1 was assessed and the role of FOXC1 in regulating cellular functions in breast cancer was further characterized.

Forkhead box transcription factors, including Forkhead box C1 (FOXC1, also known as forkhead-like 7 (FKHL7)), are transcription factors characterized by a common 100-amino acid winged-helix DNA-binding domain termed the forkhead box domain, and play important roles in regulating the expression of genes involved in cell growth, survival, differentiation embryonic mesoderm development, migration, and longevity (Nishimura et al., 1998). The FOXC1/FKHL7 gene and protein sequences are known, and can be found in GenBank (Accession Nos. AR140209 (complete sequence; SEQ ID NO:12), AR140210 (coding sequence; SEQ ID NO:13) and AAE63616 (amino acid sequence; SEQ ID NO14), the sequences of which are incorporated by reference in their entirety as if fully set forth herein). As a result of the studies described herein, it has been determined that FOXC1 expression in human breast cancer, both at the mRNA and at the protein level, occurs consistently and exclusively in basal-like breast cancers. Furthermore, in a head-to-head comparison with other suggested biomarkers of basal-like breast cancer and as shown by statistically significant in both univariate as well as multivariate analyses described in the examples below, FOXC1 has emerged as the most indicative and the most characteristic biomarker of BLBCs, in its ability to diagnose, prognose and treat BLBC.

One important feature of the above results was the exclusive nature of the association between FOXC1 and basal-like breast cancers: its expression is elevated only in basal-like molecular subtypes of breast cancers.

As mentioned above, while many genes are described to be characteristic biomarkers of certain cancer types, and many others are described to be of functional importance to the survival and maintenance of the malignant phenotype, very few are demonstrated to have robust prognostic significance. This is because very few are critical by themselves and instead are part of extremely large and complex networks of biomolecules whose overall function cannot be determined unless the molecules which are most central and pivotal in the network are identified. FOXC1 has been demonstrated to be of extremely high prognostic significance, being predictive of the high mortality and metastasis rate specifically associated with basal-like breast cancers.

Both basal-like triple-negative breast cancers as well as hybrid basal-like breast cancers (HER2 and luminal) have a high rate of metastasis to the brain, a devastating complication of this dreaded disease. The studies described herein show that a 30-member gene signature associated with FOXC1 is predictive of the brain specific metastases observed in the above two subtypes of breast cancer.

The clinical significance of FOXC1 expression is not restricted to breast cancer but may extend to other cancers, including but not limited to, melanoma, neuroendocrine tumors, brain tumors (such as glioblastoma multiforme, or astrocytoma), renal cell cancer, sarcomas (such as synovial sarcoma), and leukemia. FOXC1 expression has been shown to characteristically and exclusively define biologically and clinically aggressive subsets in such cancers and can be used both as a diagnostic as well as prognostic biomarker for these specific cancer types. Furthermore, similar to basal-like breast cancer, FOXC1 is a suitable therapeutic target for these specific cancer types.

The above described findings have clear and important implications for personalized medicine and personalized cancer care as detection of FOXC1 status of the described specific subsets of patients with breast cancer (and/or other cancers like gastric cancer and colon cancer) enables more tailored and specific therapeutic interventions with a greater likelihood of arresting disease progression, extending life expectancy or even achieving a cure.

In some embodiments, a method of use for a theranostic biomarker such as FOXC1 comprises an algorithm for its potential clinical use as a diagnostic tool. While FOXC1 may be used as an independent biomarker, it may also be used alongside other biomarkers such as HER2, ER and PR. For example, in triple-negative breast cancer, the algorithm may include the following steps. First, a patient who has either mammographic or breast MRI—detected abnormality or findings on a clinical examination is designated as suspicious for breast cancer. Next, the patient would undergo a FNNCore biopsy/Excisional biopsy to obtain a tumor tissue. Next, routine pathologic examination of the above-obtained tumor tissue establishes diagnosis of breast cancer. The tumor tissue would then be subjected to immunohistochemical (IHC) staining for ER, PR and HER2. Patients that are found to be triple negative (i.e. ER$^-$/PR$^-$/HER2$^-$) would have their tumor tissue further tested by IHC for FOXC1. Next, patients that are found to be FOXC1 positive can thus be definitively diagnosed to have basal-like triple negative breast cancer.

In another embodiment a theranostic biomarker such as FOXC1 is used as a prognostic tool. FOXC1 may be used to predict the prognosis of factors including, but not limited to, overall survival, recurrence-free survival, the propensity of developing a distant metastasis or the time to develop a distant metastasis (such as brain metastasis), or a propensity for resistance to a targeted cancer therapy regimen. The term "propensity for resistance" to a targeted cancer therapy regimen as used herein may be a predictor of resistance or a predictor of a decreased efficacy (i.e., therapy is less effective from the start of treatment) of a targeted cancer therapy regimen in a cancer patient. A high level of FOXC1 (either protein or RNA) predicts a poor prognosis of such factors, (i.e., decreased overall survival, decreased disease specific survival, decreased recurrence-free survival, increased rate of loco-regional and for distant metastasis) as compared with low FOXC1 levels in specific subsets of patients with breast cancer (and/or other cancers including but not limited to, melanoma, neuroendocrine tumors, brain tumors-such as glioblastoma multiforme, astrocytoma, renal cell cancer, sarcomas—such as synovial sarcoma, and leukemia).

In one embodiment, FOXC1's use as a prognostic tool includes an algorithm. For example, the algorithm may include the following steps, using triple-negative breast cancer as an example. First, a subject whose samples are qualitatively FOXC1 positive based on IHC have samples sent for further quantitative analysis for FOXC1 level using an RT-PCR or other quantitative technique such as a QuantiGene® assay (Panomics). Based on the quantitative value of FOXC1 expression thus obtained, a numerical Prognostic Index FOXC1 Score™ will be calculated for the individual patient which will help determine patient-specific estimates of overall survival, recurrence free survival, time to distant metastasis and type of metastasis associated with basal-like triple-negative breast cancer. This method makes personalized medical care possible for BLBC patients.

FOXC1 Represses Estrogen Receptor-α Expression in Human Breast Cancer Cells by Increasing Nuclear Factor-κB (NF-κB) Signaling The sex steroid hormone estrogen plays important roles in the development of normal mammary glands and breast cancer (Dhasarathy et al., 2007). Most established effects of estrogen are mediated through its direct binding to two nuclear receptors, estrogen receptor (ER)-α and -β (Couse and Korach, 1999; Kuiper et al., 1997). Both receptors are transcription factors that induce the expression of many breast cancer-related genes. Although ERβ is expressed in breast cancer, its role in tumor progression is not clear (Fuqua et al., 2003). On the other hand, the role of ERα in human breast cancer is well-established. More than 60% of human breast cancers are ERα positive (Keen and Davidson, 2003). It is a prognostic factor for breast cancer and correlates with a higher degree of tumor differentiation and increased disease-free survival (Osborne, 1998). Thus ERα expression defines a subgroup of breast cancer patients who, in general, have a more favorable prognosis than patients with ER-α-negative tumors (Zhao et al., 2008). ERα is also a target for antiestrogen therapy and a predictive marker for response to the therapy (Park and Jordan, 2002).

There is tremendous interest in understanding the mechanisms whereby ERα expression and signaling is modulated in breast cancer and in exploiting this knowledge to develop and improve therapeutic interventions targeting ERα. Although several transcription factors or signaling proteins have been identified as ERα regulators, the cellular and molecular events that regulate ERα expression in tumors are not well understood as yet. In addition, the clinical relevance and biological significance of these regulations are still under investigation. It was found that p53 binds to the ERα promoter and positively regulates the transcription of ERα in breast cancer cells (Shirley et al., 2009). In contrast, another study showed that p53 activation decreases the transcriptional activity of ERα by elevating the Kruppel-like factor 4 transcription factor, which can interfere with the DNA-binding function of ERα (Akaogi et al., 2009). Similarly, the BRCA1 tumor suppressor gene has been found to activate or inhibit ERα expression in different studies (Nosey et al., 2007; Rosen et al., 2005). The transcription factor Oct-1 can also be recruited to the ERα promoter to elicit ERα transcription (Nosey et al., 2007).

In breast cancer cell lines, expression of ERα is associated with levels of active forkhead box 0 protein 3a (FOXO3a)

(Guo and Sonenshein, 2004). Increased FOXO3a expression induces ERα transcription and protein levels. FOXO3a can bind to two conserved forkhead binding sites in the ERα promoter. Thus FOXO3a may represent an important intracellular mediator of ERα expression (Guo and Sonenshein, 2004). In support of this study, Belguise et al. showed that PKCq is elevated in ERα-negative breast cancers, activates Akt and thereby inactivates FOXO3a, leading to decreased synthesis of ERα (Belguise and Sonenshein, 2007). It is also well-documented that hyperactivation of MAPK induces loss of ERα expression in breast cancer cells (Oh et al., 2001). Both Akt and MAPK may be implicated in the downregulation of ERα by EGFR/HER-2, which may give rise to an inverse correlation between EGFR/HER-2 and ERα status in breast cancers (Oh et al., 2001; Saceda et al., 1996). Most recently, a G protein-coupled receptor Adenosine A1 receptor has been reported to upregulate ERα expression (Lin et al.). Furthermore, ERα expression can also be regulated through epigenetic modification, e.g. hypermethylation at its promoter, which has been reported to be responsible for the loss of ERα in some breast cancer cells (Yoshida et al., 2000).

As described by the studies herein, forkhead box transcription factor FOXC1 has been identified as an important marker for human basal-like breast cancer, which lacks or underexpresses estrogen receptor-α (ERα). Further, as discussed in detail below, FOXC1 expression was shown to consistently and inversely correlate with ERα expression by analyzing multiple cDNA microarray data sets of human breast cancer. Overexpression of FOXC1 in ERα-positive breast cancer cells downregulated ERα mRNA and protein levels, and reduced cellular responses to estradiol and tamoxifen treatment. FOXC1 overexpression caused an increase in levels of p65 protein, thereby eliciting NF-κB-mediated suppression of ERα. Pharmacologic inhibition of NF-κB in FOXC1-overexpressing MCF-7 breast cancer cells diminished these effects of FOXC1. Taken together, these results reveal a FOXC1-driven mechanism that explains the loss or low expression of ERα in basal-like breast cancer and provide a paradigm for studying the regulation of ERα during breast cancer progression.

FOXC1 as a Therapeutic Target for Basal-Like Breast Cancer

The studies described herein show that FOXC1 plays an important role in initiating and maintaining the aggressive capacity for cellular proliferation, invasion and migration that is typical of basal-like breast cancers. These are well accepted precursor attributes that are necessary for and associated with metastasis to distant organs, a clinical feature which is predicted by a patient's FOXC1 status.

Studies in which FOXC1 expression is targeted and knocked down dramatically reduces the above aggressive features of cancer cells. This demonstrates the utility of FOXC1 as a therapeutic drug target specifically for basal-like breast cancers.

While the clinical significance of the hybrid basal-like subtypes described above has not previously been recognized, these subtypes are typically resistant to targeted receptor therapy, even though they express the target receptor. For example, the hybrid basal-like/HER2$^+$ subtype is typically intrinsically resistant to HER2$^+$ targeted therpies including, but not limited to, anti-HER2 antibodies (e.g., trastuzumab (Herceptin®), pertuzumab and ertumaxomab) and tyrosine kinase inhibitors (e.g., lapatinib)), despite being HER2 positive. Similarly, the hybrid basal-like/luminal subtype is typically intrinsically resistant to hormone receptor targeted therapies including, but not limited to, selective estrogen receptor modulators (SERMS) (e.g., tamoxifen), and other therapies such as aromatase inhibitors (e.g., anastozole (Arimidex®), exemestane (Aromasin®) and letrozole (Femara®)) and anti-estrogens (e.g., toremifene citrate (Fareston®), This resistance to or decrease in efficacy to targeted receptor therapy is indicated by FOXC1. Thus, FOXC1 positive status may be used as a predictive biomarker of resistance to or decrease in efficacy of biologic therapy attempted with trastuzumab (Herceptin®) or tamoxifen in patients with hybrid basal-like breast cancers. Administration of targeted therapy directed against FOXC1 in hybrid basal-like/HER2$^+$ subtype tumors and hybrid basal-like/luminal subtype tumors should restore therapeutic sensitivity to trastuzumab (Herceptin®) and tamoxifen, respectively.

Hybrid basal-like subtype tumors are even more aggressive in their biology and clinical characteristics than either the molecular subtype (HER2$^+$ or luminal) or the basal-like subtype alone. Hence any and all therapeutic efforts in this group should include FOXC1 targeted therapy as well as targeted therapy from the earliest possible time after diagnosis.

Validated as a prognostic biomarker, FOXC1 status can be utilized in clinical decision making with respect to recommendations for offering standard adjuvant chemotherapy, enrollment in adjuvant chemotherapy clinical trials, offering neoadjuvant chemotherapy, and enrollment in neoadjuvant chemotherapy clinical trials, to patients with basal-like breast cancer. FOXC1 status may also be utilized in clinical decision making with respect to treatment recommendations for a triple negative-diagnosed patient based on a determination that the patient has a BLBC subtype that is resistant to targeted or other treatments or treatment regimens. For example, a patient diagnosed as triple negative and FOXC1+ is likely to be resistant to most targeted therapies and/or chemotherapy, and may therefore decide to forego treatments or treatment regimens in favor of living the rest of their life without the negative effects that are often associated with said treatments. Alternatively, a FOXC1 inhibitor or other FOXC1 targeted therapy may be used in conjunction with adjuvant and neoadjuvant chemotherapy regimens.

The pharmaceutical composition may include, but is not limited to, an FKBP52 inhibitor, a CD147 inhibitor, and a pharmaceutically acceptable carrier.

In one embodiment, a method for treating cancer may include administering a pharmaceutical composition that includes a pharmaceutically acceptable carrier and a therapeutically effective amount of a substance that targets and inhibits FOXC1 expression or activity (a FOXC1 inhibitor) for the targeted biologic therapy of basal-like/triple negative breast cancer. In another embodiment, the pharmaceutical composition may also include a therapeutically effective amount of a substance that targets a receptor for the targeted biologic therapy of other hybrid basal-like breast cancers. In one embodiment, the substance that targets a receptor may include, but is not limited to, ER (for targeting the hybrid basal-like/luminal subtype) or HER2 (for targeting the hybrid basal-like/HER2 subtype).

In one embodiment, the FOXC1 inhibitor may include any suitable substance able to target intracellular proteins or nucleic acid molecules alone or in combination with an appropriate carrier or vehicle, including, but not limited to, an antibody or functional fragment thereof, (e.g., Fab', F(ab')$_2$, Fab, Fv, rIgG, and scFv fragments and genetically engineered or otherwise modified forms of immunoglobulins such as intrabodies and chimeric antibodies), small molecule inhibitors of the FOXC1 protein, chimeric proteins or peptides, gene therapy for inhibition of FOXC1 transcription, or an RNA interference (RNAi)-related molecule or morpholino molecule able to inhibit FOXC1 gene expression and/or translation. In one embodiment the FOXC1 inhibitor is an RNAi-related molecule such as an siRNA or an shRNA for inhibition of FOXC1 translation. An RNA interference (RNAi) molecule is a small nucleic acid molecule, such as a short interfering RNA (siRNA), a double-stranded RNA (dsRNA), a micro-RNA (miRNA), or a short hairpin RNA (shRNA) molecule, that complementarily binds to a portion of a target gene or mRNA so as to provide for decreased levels of expression of the target.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. In one embodiment, the pharmaceutically acceptable carrier is a PEGylated immunoliposome for encapsulating the RNAi-related molecule. The PEGylated immunoliposomes or other carrier or delivery vehicle may be specifically targeted to basal-like tumor cells or specific hybrid basal-like subtype tumor cells by conjugating recombinant human and/or chimeric monoclonal antibodies or functional fragments thereof to the liposomal membrane which are specific for cell surface protein and/or carbohydrate and/or glycoprotein markers specific to the basal-like subtype that is targeted. Such markers that may be targteted include, but are not limited to, CD109, HMW-MAA, HER2, ER, CK5/6, EGFR, c-Kit and any other suitable marker for targeting a desired tumor subtype.

Compositions containing pharmaceutically acceptable carriers are described in a number of sources which are well known and readily available to those skilled in the art. For example, Remington: The Science and Practice of Pharmacy (Gerbino, P. P. [2005] Philadelphia, Pa., Lippincott Williams & Wilkins, 21st ed.) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The pharmaceutical composition described above is administered and dosed in accordance with good medical practice, taking into account the clinical condition of the individual patient, the site and method of administration, scheduling of administration, patient age, sex, body weight, and other factors known to medical practitioners. The therapeutically effective amount for purposes herein is thus determined by such considerations as are known in the art. For example, an effective amount of the pharmaceutical composition is that amount necessary to provide a therapeutically effective decrease in FOXC1. The amount of the pharmaceutical composition should be effective to achieve improvement including but not limited to total prevention and to improved survival rate or more rapid recovery, or improvement or elimination of symptoms associated with the chronic inflammatory conditions being treated and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the patient and the route of administration.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references cited above and below in the specification are incorporated by reference in their entirety, as if fully set forth herein.

Example 1

FOXC1 is a Prognostic Biomarker with Functional Significance in Basal-Like Breast Cancer Gene expression signatures for a basal-like breast cancer (BLBC) subtype have been associated with poor clinical outcomes. As described below, overexpression of the transcription factor FOXC1 is shown to be a consistent feature of BLBC compared with other molecular subtypes of breast cancer. Elevated FOXC1 expression predicted poor overall survival in BLBC (P=0.0001), independently of other clinicopathologic prognostic factors including lymph node status, along with a higher incidence of brain metastasis (P=0.02) and a shorter brain metastasis—free survival in lymph node—negative patients (P<0.0001). Ectopic overexpression of FOXC1 in breast cancer cells increased cell proliferation, migration, and invasion, whereas shRNA-mediated FOXC1 knockdown yielded opposite effects. These findings identify FOXC1 as a theranostic biomarker that is specific for BLBC, offering not only a potential prognostic candidate but also a potential molecular therapeutic target in this breast cancer subtype.

Materials and Methods

Microarray Analysis.

Publicly available datasets of human breast cancer gene expression microarrays (Richardson et al. 2006; Farmer et al. 2005; Hess et al. 2006; Ivshina et al. 2006; Miller et al. 2005; van de Vijver et al. 2002; Herschkowitz et al. 2007; Sorlie et al. 2003; Wang et al. 2005; Pawitan et al. 2005) comprising of raw expression level data files and the ExpO Project database of the International Genomics Consortium (IGC) at https://expo.intgen.org were downloaded were analyzed using Genespring GX 10.0 software (Agilent Technologies) (see Table 1 below). A total of 2,073 breast cancer patient samples were analyzed. For cDNA arrays (3 of 11 data sets), the $\log_2$ normalized signal intensity values were directly imported into the Genespring software platform, obtained from the respective public web repository. For microarray raw data obtained from Affymetrix arrays (8 of 11 data sets), signal intensities were obtained using the Robust Multi-chip Averaging (RMA) algorithm to perform background correction, normalization and summarization of probe-level raw data. All values underwent baseline transformation to median of all samples in a particular dataset on a (per gene)/(per probe) set basis.

For identification of the molecular subtypes, we employed the commonly used 306-member Intrinsic Gene Set (IGS) (Hu et al. 2006). Only 293 genes of the original 306-gene panel were represented on the microarray platform of our test dataset that was selected based on its inclusion of normal breast tissue samples (Richardson et al 2006). We subjected all datasets to a hierarchical clustering algorithm employing a Pearson uncentered similarity metric and the average linkage rule based on the 293-gene IGS. Datasets were then clustered into luminal A/B, HER2, and basal-like subtypes based on IGS. In the Richardson et al. dataset, 12 samples were excluded as they were derived from normal organoid prepa-

TABLE 1

Summary of analyzed microarray datasets.

| Reference No. | Array Name | Platform Technology | Sample Size | Complete IHC Data | Survival Analysis |
|---|---|---|---|---|---|
|  | ExpO | Affymetrix U133 plus 2.0 | 250 | − | − |
| 9 | Richardson et al. | Affymetrix U133 plus 2.0 | 47 | − | − |
| 10 | Farmer et al. | Affymetrix U133A | 49 | − | − |
| 11 | Hess et al. | Affymetrix U133A | 133 | + | − |
| 12 | Ivshina et al. | Affymetrix U133A | 249 | − | − |
| 13 | Miller et al. | Affymetrix U133A | 251 | − | − |
| 14 | van de Vijver et al. | cDNA | 295 | − | + |
| 15 | Herschkowitz et al. | cDNA | 232 | − | + |
| 16 | Sorlie et al. | cDNA | 122 | − | + |
| 17 | Wang et al. | Affymetrix U133A | 286 | − | + |
| 18 | Pawitan et al. | Affymetrix U133A | 159 | − | + |

All microarray datasets used in this study are from publicly available databases, and such databases require that the gene expression raw data, deposited by the original investigators, meet stringent quality control criteria prior to acceptance. Furthermore, each dataset has been earlier reported in the literature and individual quality control measures are reported in the original references. As such, in the present study, quality control measures were taken to confirm prior established data quality, rather than as an initial step to document data quality. Array quality control was performed using 3D Principal Component Analysis (PCA) plots, Internal Controls comprising of 3'/5' ratios for a set of specific housekeeping gene probe sets, and Hybridization Controls. A 3'/5' ratio of greater than 3 was considered to be unacceptable (representative of either degraded starting RNA or problem with the cDNA synthesis reaction). The signal intensities of pre-mixed hybridization control transcripts added to the hybridization mix in known staggered concentrations should increase as expected with the known staggered concentrations. Deviation from the expected intensity profile of these controls, as assessed by visual inspection of Hybridization Control plots, was considered to be unacceptable (representative of a problem either with the hybridization or washing process). Based on these criteria, only one array (from the Richardson et al. dataset) among a total of 2,073 examined arrays was removed. The PCA scores of each array were plotted in 3D in order to examine the clustering pattern of samples. Three major clusters were observed in each dataset, consistent with the expected biologic variation in this population resulting in segregation into the three molecular subtypes—luminal, HER2 and basal-like. Probes from the spotted arrays were filtered based on flag values. Otherwise they were filtered based on signal intensity values so that values between 20.0 and 100.0 percentiles in a given dataset were retained.

rations and not normal breast tissue, 4 BRCA positive samples were excluded to reduce bias, 1 sample was excluded for not meeting quality control standards and 1 sample classified by the authors as basal-like clustered with the luminal subtype and was thus excluded from the analysis.

To determine the correlation between FOXC1 and triple-negative status, we searched for publicly available datasets that contained complete ER, PR, and HER2 expression profiles of each breast cancer specimen based on immunohistochemical analysis. Only one such dataset (Hess et al.) was identified (Hess et al. 2006).

Average relative mRNA levels (mean $\log_2$ signal intensity) for each IGS gene and for reported markers of BLBC in the literature (αB-crystallin (Moyano et al. 2006), moesin (Charafe-Jauffret et al. 2007), CD109 (Hasegawa et al. 2008), p-Cadherin, EGFR (Nielsen et al. 2004), CK5 (Nielsen et al. 2004; Korsching et al. 2008), CK14 (Korsching et al. 2008), CK17 (Korsching et al. 2008), c-Kit (Nielsen et al. 2004), ITGB4 (Lu et al. 2008), and FOXC2 (Mani et al. 2007)) were determined according to molecular subtype. Expression values for some genes were not normally distributed for which reason we employed nonparametric analysis (Mann-Whitney Test) in comparing Basal-like group vs. pooled non-Basal-like group expression values ($\log_2$ normalized signal intensity) for each gene. All statistical analyses were performed using SAS software (Version 9.1.3, SAS Institute, Cary, N.C.). A stepwise logistic regression analysis was performed to identify the gene most characteristic of the basal-like group. In view of the small sample size of the Richardson et al. dataset (with highly predictive covariates resulting in non-convergence), Firth's modified logistic regression analysis used to reduce the bias of maximum likelihood estimation in this array. Statistical significance for each of these analyses was defined as $P<0.05$. To maintain statistical power, each dataset was analyzed independently as shown below in Tables 2-5.

TABLE 2

Statistical analysis of biomarker in molecular subgroups classified by IGS in the Richardson et al. breast cancer microarray dataset (2).

| Gene | Normal Mean ± SD (Median) | Luminal Mean ± SD (Median) | HER2 Mean ± SD (Median) | Basal-like Mean ± SD (Median) | Univariate Wilcoxon Rank Sum Test (Basal-like vs. Other) P-value | Multivariate Logistic Regression P-value† |
|---|---|---|---|---|---|---|
| FOXC1 | −0.11 ± 0.73 (−0.23) | −1.63 ± 0.38 (−1.60) | −0.99 ± 0.71 (−1.03) | 3.61 ± 0.75 (3.63) | <0.0001 | 0.0006 |
| CRYAB | −1.87 ± 0.39 (1.87) | −1.61 ± 1.11 (−1.66) | −1.82 ± 0.78 (−1.93) | 1.34 ± 1.30 (1.27) | 0.001 | NS |
| KRT5 | 2.98 ± 0.38 (2.72) | −1.17 ± 0.98 (−1.32) | −1.35 ± 1.02 (−1.31) | 0.81 ± 1.48 (1.14) | NS | NS |
| KIT | 3.08 ± 0.47 (3.07) | −0.93 ± 0.88 (−1.03) | −1.21 ± 0.76 (−1.16) | 0.60 ± 1.22 (0.32) | NS | NS |
| CDH3 | 1.21 ± 0.43 (1.35) | −1.13 ± 0.66 (−1.40) | −0.11 ± 0.92 (−0.20) | 0.64 ± 1.24 (0.97) | 0.036 | NS |
| MSN | 0.18 ± 0.33 (0.15) | −0.32 ± 0.61 (−0.41) | −0.57 ± 0.44 (−0.51) | 0.60 ± 0.88 (0.70) | 0.002 | NS |
| KRT17 | 2.84 ± 0.25 (2.81) | −1.03 ± 0.80 (−1.05) | −0.79 ± 1.13 (−0.95) | 0.92 ± 1.78 (1.05) | NS | NS |
| EGFR | 0.32 ± 0.40 (0.39) | −0.50 ± 0.30 (−0.51) | 0.02 ± 0.67 (0.19) | 0.25 ± 0.55 (0.27) | 0.044 | NS |
| KRT14 | 3.44 ± 0.51 (3.60) | −1.30 ± 1.84 (−0.82) | −2.15 ± 1.82 (−1.49) | 0.69 ± 2.53 (0.59) | NS | NS |
| CD109 | −0.46 ± 0.62 (−0.25) | −0.45 ± 0.91 (−0.19) | −0.77 ± 1.02 (−1.08) | 0.46 ± 0.98 (0.63) | 0.004 | NS |
| ITGB4 | 0.40 ± 0.39 (0.34) | −0.32 ± 0.35 (−0.37) | 0.24 ± 0.74 (0.01) | 0.19 ± 0.87 (0.13) | NS | NS |
| FOXC2 | 0.09 ± 0.13 (0.07) | −0.01 ± 0.20 (−0.03) | −0.01 ± 0.16 (0.03) | 0.04 ± 0.26 (0.01) | NS | NS |

Values in each molecular subtype column are the mean ± SD of the log2 normalized signal intensity for the best representative cDNA probe for that gene. NS, $P > 0.05$.
†Firth's modified logistic regression analysis used to reduce the bias of maximum likelihood estimation in this array (characterized by small sample size with highly predictive covariates resulting in non-convergence). Basal-like (yes = 1, no = 0) was used as a dependent variable.

TABLE 3

Statistical analysis of biomarker in molecular subgroups classified by IGS in the Ivshina et al. breast cancer microarray dataset (14).

| Gene | Luminal Mean ± SD (Median) | HER2 Mean ± SD (Median) | Basal-like Mean ± SD (Median) | Univariate Wilcoxon Rank Sum Test (Basal-like vs. Other) P-value | Multivariate Logistic Regression P-value |
|---|---|---|---|---|---|
| FOXC1 | 0.02 ± 0.27 (−0.01) | 0.00 ± 0.28 (−0.05) | 1.88 ± 0.71 (1.92) | <0.0001 | 0.0033 |
| CDH3 | −0.06 ± 0.76 (−0.18) | 0.90 ± 0.84 (0.73) | 1.94 ± 0.92 (2.07) | <0.0001 | 010199 |
| CRYAB | −0.03 ± 0.79 (−0.06) | −0.30 ± 0.44 (−0.40) | 1.94 ± 1.23 (2.20) | <0.0001 | NS |
| EGFR | −0.05 ± 0.94 (−0.17) | 0.41 ± 0.86 (0.28) | 1.20 ± 0.57 (1.15) | <0.0001 | NS |
| KRT17 | 0.13 ± 0.99 (−0.11) | 0.51 ± 1.10 (0.09) | 2.06 ± 1.54 (1.99) | <0.0001 | NS |
| KRT5 | 0.09 ± 1.08 (−0.21) | 0.12 ± 0.85 (0.00) | 2.20 ± 1.34 (2.20) | <0.0001 | NS |
| MSN | −0.10 ± 0.48 (−0.04) − | 0.06 ± 0.35 (−0.12) | 0.74 ± 0.42 (0.82) | <0.0001 | NS |
| ITGB4 | −0.03 ± 0.44 (−0.07) | 0.28 ± 0.46 (0.35) | 0.45 ± 0.65 (0.26) | 0.0016 | NS |
| KIT | 0.11 ± 1.00 (0.00) | −0.27 ± 0.87 (−0.46) | 1.07 ± 1.45 (1.25) | 0.0011 | NS |
| KRT14 | −0.24 ± 1.96 (−0.15) | −0.30 ± 1.47 (−0.57) | 1.99 ± 2.08 (1.55) | 0.0001 | NS |
| FOXC2 | 0.00 ± 0.17 (0.00) | 0.05 ± 0.16 (0.05) | 0.07 ± 0.26 (0.02) | NS | NS |

Values in each molecular subtype column are the mean ± SD of the log2 normalized signal intensity for the best representative cDNA probe for that gene.
NS, $P > 0.05$.
* CD109 does not have any representative probes on this microarray platform. In the multivariate logistic regression analysis, dependent variable is basal-like.

TABLE 4

Statistical analysis of biomarker in molecular subgroups classified by IGS in the Miller et al. breast cancer microarray dataset (15).

| Gene | Luminal Mean ± SD (Median) | HER2 Mean ± SD (Median) | Basal-like Mean ± SD (Median) | Univariate Wilcoxon Rank Sum Test (Basal-like vs. Other) P-value | Multivariate Logistic Regression P-value |
|---|---|---|---|---|---|
| FOXC1 | 0.02 ± 0.28 (−0.01) | −0.04 ± 0.29 (−0.12) | 1.86 ± 0.71 (1.90) | <0.0001 | 0.0003 |
| CDH3 | −0.05 ± 0.76 (−0.16) | 0.87 ± 0.94 (0.75) | 1.95 ± 0.91 (2.09) | <0.0001 | 0.0153 |
| KRT17 | 0.13 ± 1.01 (−0.09) | 0.48 ± 1.11 (0.08) | 2.05 ± 1.54 (1.99) | <0.0001 | NS |
| EGFR | −0.04 ± 0.94 (−0.17) | 0.39 ± 0.88 (0.08) | 1.21 ± 0.57 (1.16) | <0.0001 | NS |
| MSN | −0.09 ± 0.47 (−0.03) | −0.13 ± 0.42 (−0.19) | 0.74 ± 0.42 (0.82) | <0.0001 | NS |

TABLE 4-continued

Statistical analysis of biomarker in molecular subgroups classified by IGS in the Miller et al. breast cancer microarray dataset (15).

| Gene | Luminal Mean ± SD (Median) | HER2 Mean ± SD (Median) | Basal-like Mean ± SD (Median) | Univariate Wilcoxon Rank Sum Test (Basal-like vs. Other) P-value | Multivariate Logistic Regression P-value |
|---|---|---|---|---|---|
| CRYAB | −0.01 ± 0.78 (−0.05) | −0.38 ± 0.48 (−0.41) | 1.94 ± 1.24 (2.20) | <0.0001 | NS |
| KRT5 | 0.10 ± 1.08 (−0.16) | 0.07 ± 0.88 (0.00) | 2.19 ± 1.33 (2.18) | <0.0001 | NS |
| KRT14 | −0.26 ± 1.96 (−0.14) | −0.40 ± 1.50 (−0.61) | 1.94 ± 2.07 (1.50) | <0.0001 | NS |
| ITGB4 | −0.02 ± 0.45 (−0.07) | 0.21 ± 0.46 (0.27) | 0.45 ± 0.65 (0.26) | 0.002 | NS |
| KIT | 0.12 ± 1.01 (0.01) | −0.27 ± 0.86 (−0.43) | 1.07 ± 1.45 (1.25) | 0.001 | NS |
| FOXC2 | 0.00 ± 0.17 (0.00) | 0.03 ± 0.18 (0.05) | 0.06 ± 0.26 (0.02) | NS | NS |

Values in each molecular subtype column are the mean ± SD of the log2 normalized signal intensity for the best representative cDNA probe for that gene.
NS, P > 0.05.
* CD109 does not have any representative probes on this microarray platform. In the multivariate logistic regression analysis, dependent variable is basal-like.

TABLE 5

Statistical analysis of biomarker in molecular subgroups classified by IGS in the van de Vijver et al. breast cancer microarray dataset (16).

| Gene | Luminal Mean ± SD (Median) | HER2 Mean ± SD (Median) | Basal-like Mean ± SD (Median) | Univariate Wilcoxon Rank Sum Test (Basal-like vs. Other) P-value | Multivariate Logistic Regression P-value |
|---|---|---|---|---|---|
| FOXC1 | −0.51 ± 0.21 (−0.50) | −0.41 ± 0.21 (−0.41) | 0.49 ± 0.42 (0.58) | <.0001 | 0.0028 |
| CRYAB | −0.36 ± 0.24 (−0.36) | −0.29 ± 0.19 (−0.29) | 0.27 ± 0.47 (0.28) | <.0001 | NS |
| KRT5 | −0.56 ± 0.40 (−0.50) | −0.45 ± 0.42 (−0.28) | 0.16 ± 0.56 (0.10) | <.0001 | 0.0084 |
| KIT | −0.17 ± 0.24 (−0.16) | −0.22 ± 0.25 (−0.19) | 0.05 ± 0.34 (0.05) | <.0001 | NS |
| CDH3 | −0.49 ± 0.29 (−0.49) | −0.14 ± 0.38 (−0.15) | 0.32 ± 0.31 (0.37) | <.0001 | NS |
| MSN | −0.14 ± 0.17 (−0.13) | −0.05 ± 0.16 (−0.06) | 0.21 ± 0.14 (0.24) | <.0001 | NS |
| KRT17 | −0.33 ± 0.28 (−0.35) | −0.22 ± 0.39 (−0.14) | 0.21 ± 0.46 (0.17) | <.0001 | NS |
| EGFR | −0.05 ± 0.14 (−0.05) | −0.01 ± 0.15 (−0.03) | 0.07 ± 0.21 (0.06) | <.0001 | NS |
| KRT14 | −0.10 ± 0.12 (−0.11) | −0.08 ± 0.13 (−0.11) | 0.08 ± 0.30 (0.02) | 0.0001 | NS |
| ITGB4 | −0.03 ± 0.12 (−0.03) | 0.10 ± 0.14 (0.08) | 0.12 ± 0.19 (0.12) | <.0001 | NS |

Values in each molecular subtype column are the mean ± SD of the log2 normalized signal intensity for the best representative cDNA probe for that gene.
NS, P > 0.05.
* FOXC2 and CD109 do not have any representative probes on this microarray platform. In the multivariate logistic regression analysis, dependent variable is basal-like.

For simplicity of data interpretation, normal breast-like group was not included in the analysis. The normal breast-like group resembles normal breast tissue samples with relatively high expression of genes characteristic of adipose cells and other non-epithelial cell types and low expression of luminal epithelial cell genes. Because the normal-like classification was developed by training on normal breast tissue, it has been speculated that the normal-like subgroup may be mainly an artifact of having a high percentage of normal "contamination" in tumor specimens (Parker et al. 2009). Other explanations include a group of slow-growing basal-like tumors that lack the expression of proliferation genes or a potential new subtype called claudin-low tumors (Herschkowitz et al. 2007). In addition, only some of the datasets used in our analysis contain normal-like samples. FOXC1 was not found to be overexpressed in these samples (data not shown).

Gene Signature Analysis.

With the intent of developing a gene signature associated with FOXC1 gene expression capable of accurately detecting the basal-like subtype independent of IGS, the test dataset that included normal breast tissue samples was first analyzed (2). Genes that shared coordinate upregulation and genes that shared coordinate downregulation with FOXC1 upregulation were both included. Supervised stringent inclusion criteria were used based on degree of Pearson correlation coefficients (1.0>r>0.5 for genes with coordinate upregulation and −1.0<r<−0.5 for genes with coordinate downregulation, respectively). Only those genes that maintained their high degree of correlation with FOXC1, independent of their individual correlations with breast cancer subtypes, were included in the final panel and validated in a total of 5 individually analysed microarray datasets (Richardson et al. 2006; Farmer et al. 2005; Ivshina et al. 2006; Miller et al. 2005-2, 13-15) and the ExpO Project Database of the International Genomics Consortium (IGC) at https://expo.intgen.org). The 30 genes that met the inclusion criteria while still allowing for maximal applicability across earlier generation microarray platforms (i.e. ranking in the top 30 genes associated with FOXC1 expression in 3 or more of the 5 datasets) are collectively referred to as the FOXC1 gene signature (Table 6).

TABLE 6

Pearson correlation coefficients of the 30 genes associated with FOXC1 gene expression in five microarray datasets (2, 13-15).

| No. | Dataset Gene Symbol | Richardson et al. | ExpO | Farmer et al. | Ivshina et al. | Miller et al. | Frequency* |
|---|---|---|---|---|---|---|---|
| 1 | FOXC1 | 1.00 | 1.00 | 1.00 | 1.00 | 1.00 | 5 |
| 2 | OGFRL1 | 0.86 | 0.50 | 0.49 | 0.65 | 0.66 | 4 |
| 3 | ROPN1B | 0.83 | 0.75 | 0.80 | 0.73 | 0.73 | 5 |
| 4 | ART3 | 0.83 | 0.65 | 0.59 | 0.63 | 0.64 | 5 |
| 5 | FABP7 | 0.82 | 0.39 | 0.40 | 0.57 | 0.60 | 3 |
| 6 | C10orf38 | 0.82 | 0.65 | 0.70 | 0.72 | 0.72 | 5 |
| 7 | EN1 | 0.81 | 0.74 | 0.80 | 0.74 | 0.73 | 5 |
| 8 | KCNK5 | 0.80 | 0.63 | 0.64 | 0.65 | 0.64 | 5 |
| 9 | CHODL | 0.80 | 0.60 | 0.54 | 0.56 | 0.57 | 5 |
| 10 | PRKX | 0.80 | 0.55 | 0.73 | 0.66 | 0.66 | 5 |
| 11 | C21orf91 | 0.79 | 0.56 | 0.39 | 0.52 | 0.53 | 4 |
| 12 | GABRP | 0.78 | 0.70 | 0.77 | 0.74 | 0.74 | 5 |
| 13 | ELF5 | 0.77 | 0.65 | 0.63 | 0.61 | 0.61 | 5 |
| 14 | PAPSS1 | 0.77 | 0.48 | 0.47 | 0.54 | 0.54 | 3 |
| 15 | ACTR3B | 0.77 | 0.64 | 0.63 | 0.55 | 0.55 | 5 |
| 16 | LMO4 | 0.76 | 0.41 | 0.59 | 0.65 | 0.64 | 4 |
| 17 | ZIC1 | 0.75 | 0.53 | 0.61 | 0.39 | 0.39 | 3 |
| 18 | UGT8 | 0.75 | 0.64 | 0.46 | 0.60 | 0.60 | 4 |
| 19 | MICALL1 | 0.75 | 0.70 | 0.78 | 0.64 | 0.64 | 5 |
| 20 | FOXA1 | −0.87 | −0.75 | −0.81 | −0.82 | −0.82 | 5 |
| 21 | MLPH | −0.86 | −0.70 | −0.78 | −0.69 | −0.69 | 5 |
| 22 | SIDT1 | −0.84 | −0.58 | −0.73 | −0.56 | −0.55 | 5 |
| 23 | AGR2 | −0.83 | −0.67 | −0.71 | −0.59 | −0.59 | 5 |
| 24 | SPDEF | −0.81 | −0.64 | −0.72 | −0.79 | −0.78 | 5 |
| 25 | TFF3 | −0.80 | −0.53 | −0.67 | −0.46 | −0.45 | 3 |
| 26 | AR | −0.80 | −0.50 | −0.56 | −0.58 | −0.59 | 5 |
| 27 | TBC1D9 | −0.79 | −0.62 | −0.66 | −0.66 | −0.66 | 5 |
| 28 | CA12 | −0.78 | −0.60 | −0.66 | −0.66 | −0.66 | 5 |
| 29 | GATA3 | −0.77 | −0.56 | −0.71 | −0.70 | −0.70 | 5 |
| 30 | GALNT6 | −0.75 | −0.53 | −0.66 | −0.52 | −0.51 | 5 |

*Frequency denotes the number of datasets in which the correlation of individual genes with FOXC1 expression is present (>0.50 for coordinately upregulated genes, and <−0.50 for coordinately downregulated genes, respectively).

To validate the ability of this gene signature to identify basal-like breast cancer, in addition to the aforementioned 5 datasets used to refine the gene signature, another 6 publicly available human breast cancer Affymetrix and cDNA microarray datasets were individually tested (Hess et al. 2006; Herschkowitz et al. 2007; van de Vijver et al. 2002; Sorlie et al. 2003; Wang et al. 2005; Pawitan et al. 2005) representing analysis in a total of 2,073 breast cancer patients. All datasets were subjected to a hierarchical clustering algorithm employing a Pearson uncentered similarity metric and the average linkage rule based on the 30-member FOXC1 gene signature. Extent of correct classification of breast cancer samples as belonging to the basal-like subtype was compared to those classified based on IGS.

Survival Analysis.

Next, the potential prognostic importance of FOXC1 mRNA expression in breast cancer was determined, with particular reference to assessing its ability to correctly predict the survival of patients with basal-like breast cancer. This analysis was performed with the intent to determine whether FOXC1 mRNA expression could be used as a stand alone, individual prognostic biomarker for basal-like breast cancer instead of pathologic, immunohistochemical and/or molecular classifiers such as IGS. A 295-sample breast cancer oligonucleotide microarray dataset (van de Vijver et al. 2002) with follow-up data extending over a 20 year period was subjected to analysis. The prognostic significance of FOXC1 was also examined in three additional human breast cancer cDNA datasets: A 232-sample dataset (Herschkowitz et al. 2007), a 122-sample dataset (Sorlie et. al. 2003), and a 159-sample dataset (Pawitan et al. 2005). Survival distributions were estimated using Kaplan-Meier methods and compared using the log-rank test. In multivariate survival analyses, Cox proportional hazard regression model was used incorporating phenotype status (basal-like versus non-basal-like), FOXC1 level, age, tumor size, tumor grade, and lymph node status as possible predictors of survival. Proportional hazard assumption was validated using residual plots and proportionality tests. The relative prognostic significance of two separate prognostic models was evaluated by comparing the model fit after adjusting for clinicopathologic variables. One model was based on dichotomous expression of FOXC1 mRNA levels. The other model was based on the IGS-derived basal-like cluster following hierarchical clustering. The relative prognostic significance of each model was measured using Akaike's Information Criterion (AIC) to assess the fit of the two regression models (Akaike 1974).

Association with metastasis to the brain or bone was examined in lymph node—negative breast cancer patients in the Wang et al. data set (Wang et al. 2005). The Wilcoxon rank sum test was used to assess statistical significance for this comparison. Brain specific and bone-specific metastasis-free survival was also examined in the same data set. Univariate and multivariate analyses were done using log-rank test and Cox regression model, respectively. Variables included in the multivariate analysis were selected based on statistical significance in initial univariate analysis and included age, tumor size, and lymph node status. Survival plots were created using Kaplan-Meier methods.

Immunohistochemistry and Immunoblotting

Immunohistochemistry was performed using a peroxidase detection system with human breast cancer tissue microarrays BRC961 and BR962 (US Biomax) and a polyclonal FOXC1 antibody that does not recognize FOXC2 (Lifespan Biosciences). Antibody concentration (1:100) was determined by serial titration and optimisation of the antibody on test arrays. Briefly, after antigen retrieval, primary antibodies were added, followed by a biotinylated secondary antibody incubation, which then binds to peroxidase-conjugated streptavidin. The signal was developed with diaminobenzidine as the chromogen with hematoxylin as counterstain. The immunostained slides were evaluated microscopically by estimating the proportion and average intensity of positive tumor cells with nuclear and/or cytoplasmic staining. Immunohistochemical analysis was also performed on 42 triple-negative human breast cancer specimens obtained from the Saint John's Health Center Department of Pathology and John Wayne Cancer Institute tissue bank in accordance with Institutional Review Board approval. Immunoblotting was performed using an antibody from Santa Cruz Biotechnology. Whole cell lysates for western blotting were generated by cell lysis buffer (50 mM Tris-HCl, pH 7.4, 150 mM NaCl, 2 mM EDTA, 1% NP-40, 10% glycerol) supplemented with a protease inhibitor cocktail (Sigma, St Louis, Mo.). Equal amounts of protein were separated by 10% SDS-PAGE and then transferred onto a nitrocellulose membrane. The remaining steps were conducted according to a standard immunoblotting protocol.

Results and Discussion

Figure 4:
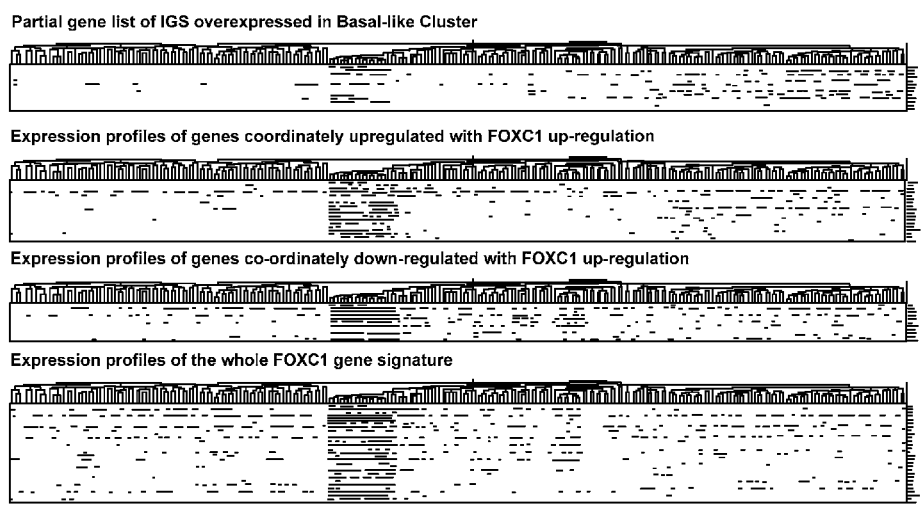
FIG. 4 shows an association of the FOXC1 gene signature with basal-like breast cancer. Gene expression heat maps of a 251-sample human breast cancer cDNA microarray dataset (Miller et al. 2005) hierarchically clustered by IGS demonstrate the overall expression profile of the FOXC1-associated 30 genes.
Figure 5:
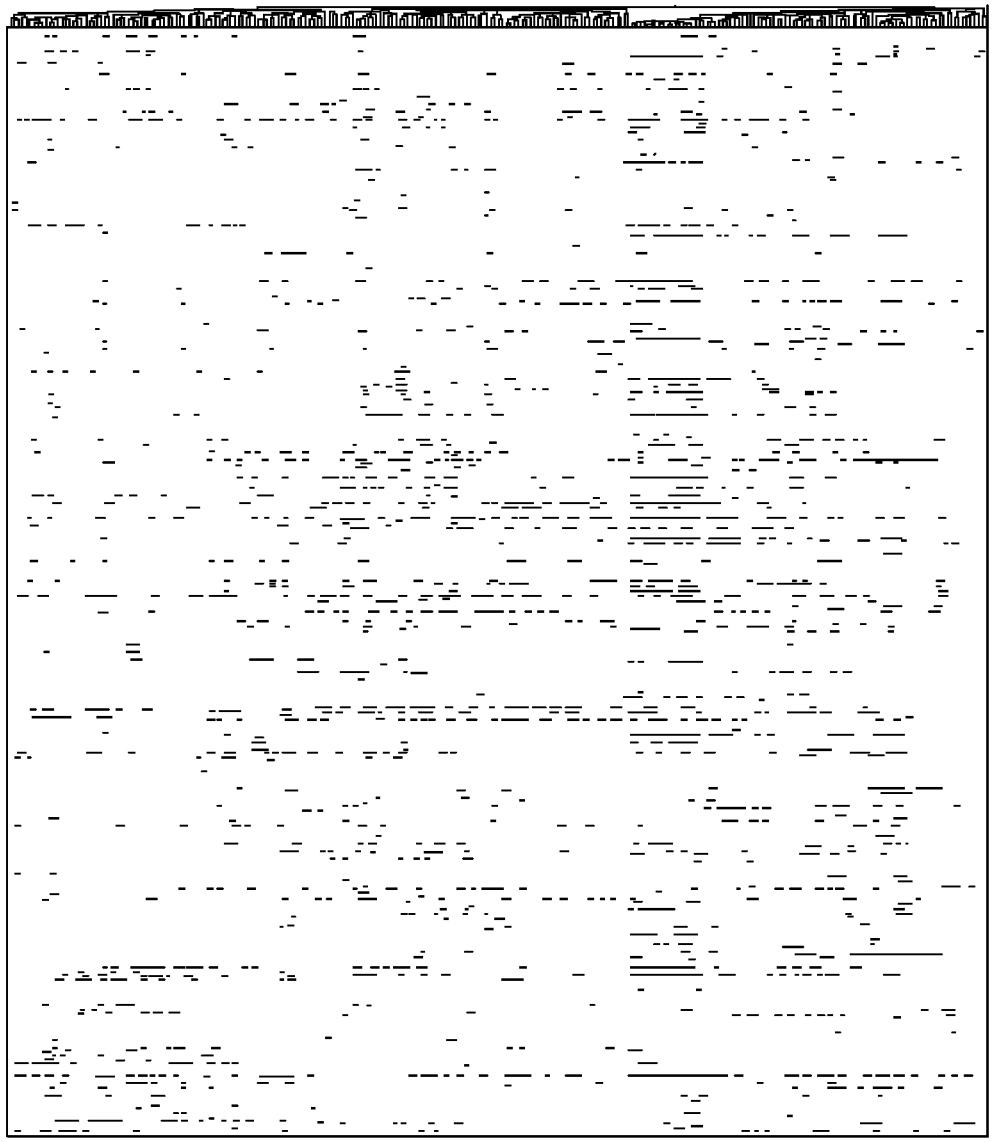
FIG. 5 shows unsupervised clustering by the FOXC1 gene signature identifies the basal-like subgroup. A 249-sample human breast cancer cDNA microarray dataset (Ivshina et al. 2006) was clustered by IGS and the FOXC1 gene signature respectively. The basal-like subtype clusters are indicated with red bars.
Figure 5:

Gene expression analysis of publicly available human breast cancer microarray data sets revealed that the Forkhead-box transcription factor FOXC1, essential for mesoderm tissue development, had significantly higher expression in the basal-like subgroup than in other subtypes (FIGS. 1A, 1B, 2 and 3A-C). High FOXC1 expression correlated positively and significantly with the basal-like subgroup, as shown in Tables 2-5 above. Elevated FOXC1 mRNA expression was also associated with triple-negative breast cancer, consistent with the notion that 60% to 90% of triple-negative breast cancers are basal-like (FIGS. 1C and 3D). A 30-gene FOXC1 signature was derived from correlation with FOXC1 expression in six data sets (Table 6, above) and validated in five separate data sets. These genes displayed an overall expression profile that coincided with the basal-like subgroup clustered by IGS (FIGS. 1D and 4). Conversely, hierarchical clustering using the FOXC1 gene signature identified the same basal-like subgroup determined by IGS (FIG. 5). Whereas pathway analysis of this gene signature did not yield a dominant pathway (data not shown), some members such as FABP7, GABRP, EN1, KCNK5, ZIC1, ACTR3B, and FOXC1 are notably involved in brain development and brain tumorigenesis, which explains why BLBC preferentially metastasizes to the brain.

Figure 6:
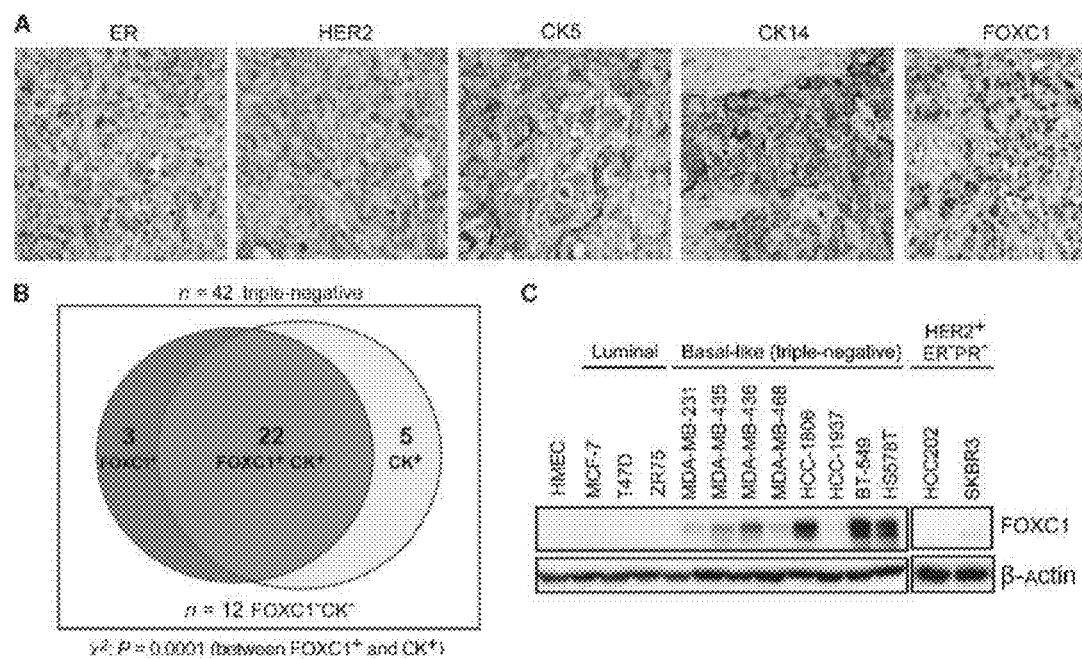
FIG. 6 illustrates FOXC1 protein expression in BLBC. A, representative immunohistochemical images of a basal-like sample from breast cancer tissue microarrays stained for ER, HER2, CK5/6, CK14, and FOXC1. FOXC1 protein was not detected in non-triple-negative specimens. B, Venn diagram showing the association between FOXC1 and cytokeratin (CK5/6 and/or CK14) immunohistochemistry status in triple-negative tumors. C, immunoblotting of FOXC1 in normal HMECs and luminal (MCF-7, T47D, and ZR75), HER2-overexpressing (SKBR3 and HCC202), or BLBC cell lines.
Figure 7:
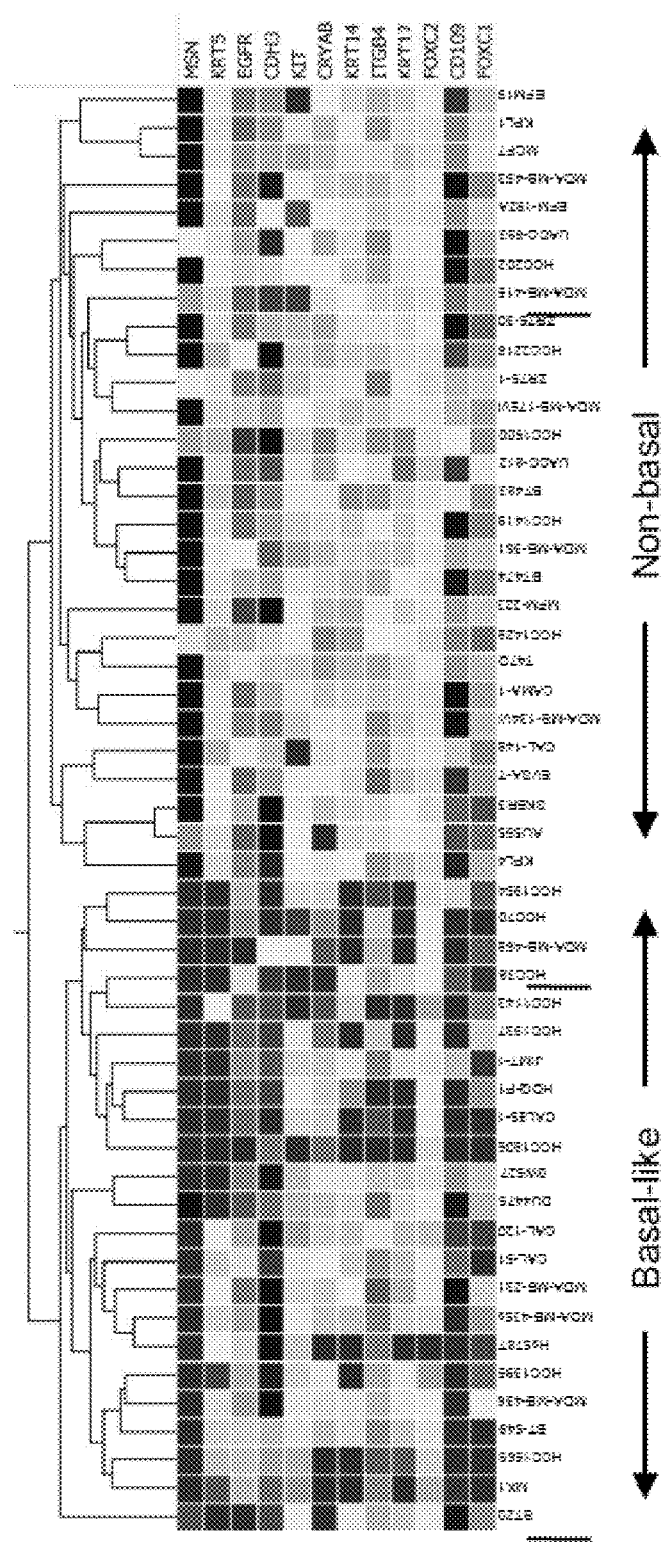
FIG. 7 illustrates that FOXC1 is overexpressed in basal-like breast cancer cell lines. Gene expression heat map from cDNA microarray analysis of 51 human breast cancer cell lines. Displayed is the same panel of 12 genes as in FIG. 2. MSN-Moesin, KRT5-Cytokeratin 5/CK5/6, CDH3-P-cadherin, CRYAB-αB-crystallin, KRT14-cytokeratin 14/CK14, KRT17-cytokeratin 17/CK17.

FOXC1 protein expression was then evaluated using immunohistochemistry on breast cancer tissue microarrays (TMA). Strong nuclear FOXC1 staining was found in triple-negative TMA samples expressing basal cytokeratins (CK5/6+ and/or CK14+; FIG. 6A) but not in non-triple-negative tumors (data not shown). Cytoplasmic staining of FOXC1 was rare, and it was normally concomitant with nuclear staining of FOXC1. This pattern of subcellular localization was confirmed in an independent cohort of 42 archived triple-negative breast cancer specimens. Positive expression of FOXC1 (FOXC1+) was associated significantly with expression of basal cytokeratins (FIG. 6B) and displayed a sensitivity of 0.81 and a specificity of 0.80 in detecting the basal-like phenotype identified by positive staining of CK5/6 and/or CK14. Absence of CK staining in some FOXC1+/ER−/PR−/HER2− samples in this cohort may reflect inconsistent expression of these cytokeratins in BLBCs defined by expression arrays (Nielsen et al. 2004). The finding that nuclear FOXC1 was consistently detected by immunohistochemistry despite its short protein half-life (<30 minutes; Berry et al. 2006) suggest a robust constitutive expression of FOXC1 in BLBC. Analysis of a microarray data set for a human breast cancer cell line panel revealed higher FOXC1 expression in BLBC cell lines (FIG. 7), which was confirmed by immunoblotting (FIG. 6C).

Figure 8:
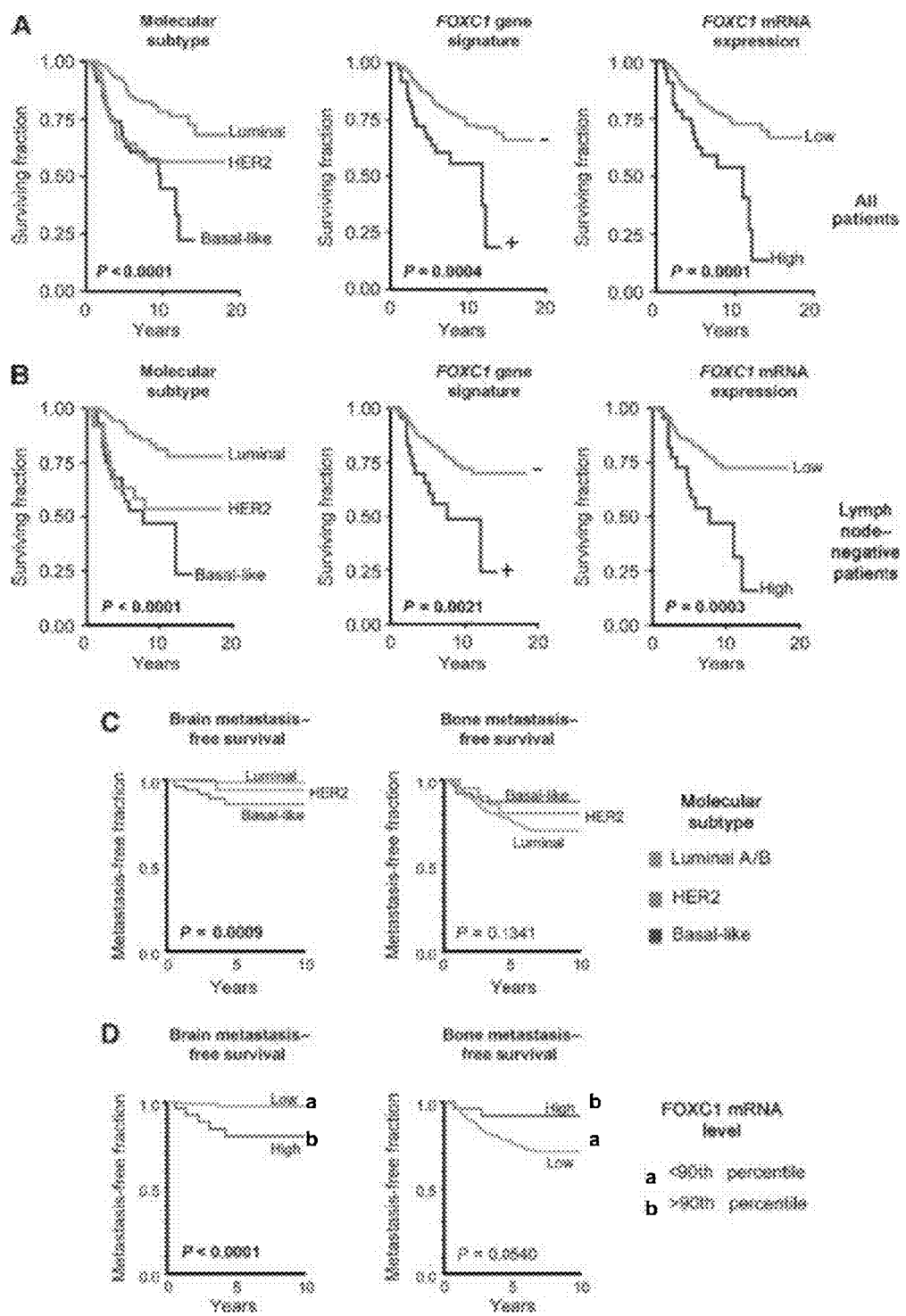
FIG. 8 illustrates prognostic significance of FOXC1 in human breast cancer. A, Kaplan-Meier curves of overall survival using data from the van de Vijver et al. data set (van de Vijver et al. 2002). Overall survival was stratified by molecular subtypes (left), the FOXC1 gene signature (middle), and FOXC1 mRNA levels (right). B, Kaplan-Meier curves of overall survival in lymph node—negative patients from the same data set. C, Kaplan-Meier curves of brain (left) and bone (right) metastasis—free survival using data from the Wang et al. data set (Wang et al. 2005) stratified by molecular subtypes. D, Kaplan-Meier curves of brain and bone metastasis—free survival stratified by FOXC1 mRNA levels from the same data set.
Figure 9:
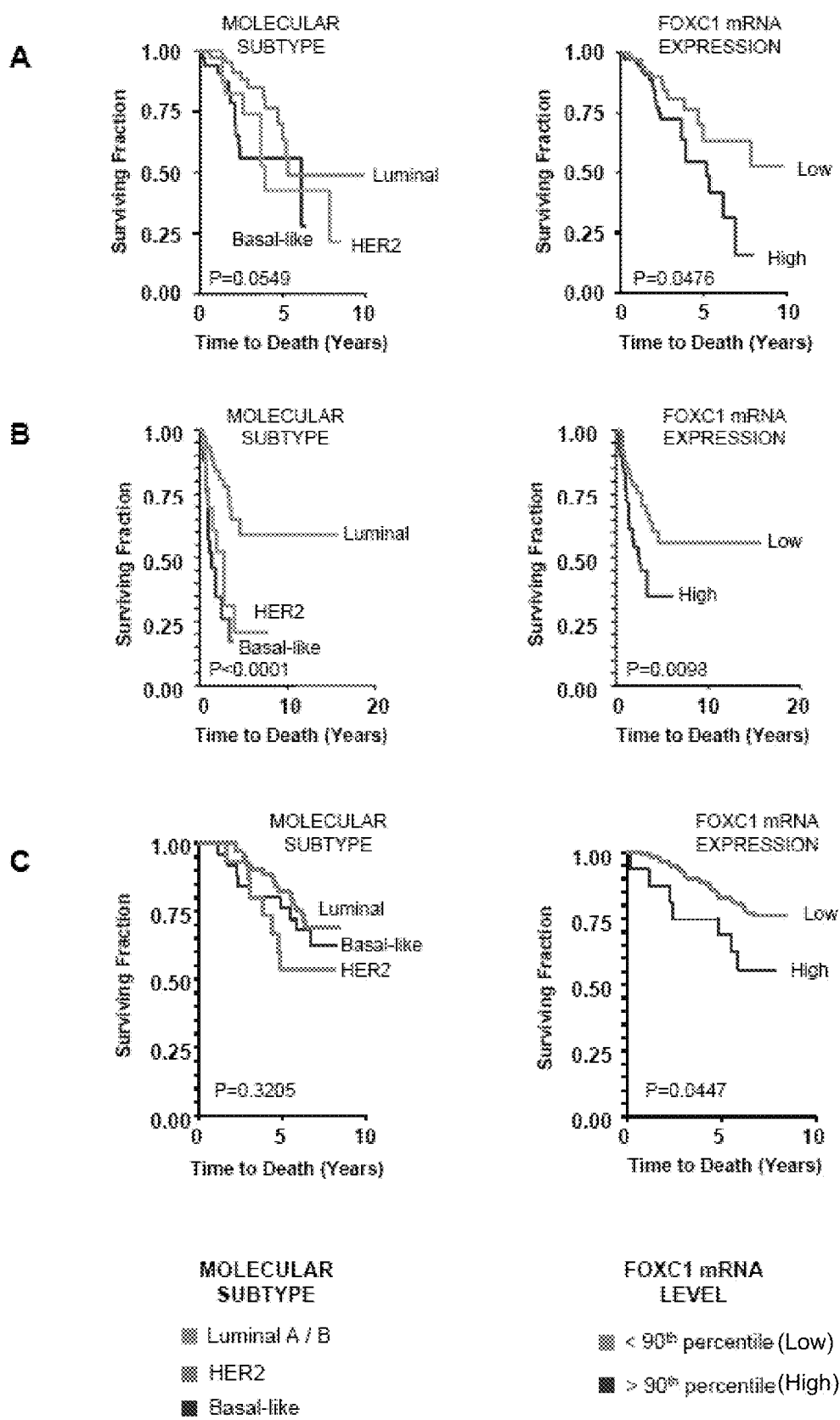
FIG. 9 illustrates prognostic power of FOXC1 expression in human breast cancers. A, Kaplan-Meier curves of overall survival using data from a 232-sample microarray dataset (Herschkowitz et al. 2007) with linked clinical information. B, Kaplan-Meier curves of overall survival using data from a 122-sample microarray dataset (Sorlie et al. 2003) with linked clinical information. C, Kaplan-Meier curves of overall survival using data from a 159-sample microarray dataset (Pawitan et al. 2005) with linked clinical information. Overall survival is displayed according to molecular subtypes (left) and FOXC1 mRNA levels (right).

The prognostic significance of FOXC1 in breast cancer was next examined in the 295-sample van de Vijver et al. data set (van de Vijver et al. 2002). In univariate analysis, overall survival was significantly worse in tumors identified using the 30-gene FOXC1 signature (P=0.0004) or using elevated FOXC1 mRNA levels alone (P=0.0001; FIG. 8A). Overall survival decreased by 35% for each unit increase of relative FOXC1 mRNA levels. In multivariate analysis, FOXC1 was an independent prognostic indicator of overall survival after adjusting for clinicopathologic variables such as age, tumor size, and lymph node status (hazard ratio, 1.25; 95% confidence interval, 1.02-1.52; P=0.02). Akaike information criteria (AIC; Akaike 1974) were used in comparing the fit of the two separate prognostic models after adjusting for clinicopathologic variables. The model based on FOXC1 mRNA expression (AIC, 820.0) was similar to the model based on the IGS-derived basal-like cluster (AIC, 815) in terms of the model fit predicting survival. The association of FOXC1 with overall survival was also shown in the 232-sample Herschkowitz et al. (Herschkowitz et al. 2007), 122-sample Sorlie et al. (Sorlie et al. 2003), and 159-sample Pawitan et al. (Pawitan et al. 2005) data sets (FIG. 9). Furthermore, the FOXC1 gene signature and mRNA levels, like the basal-like phenotype, allowed prognostic stratification of lymph node—negative breast cancers (P=0.0003) in the van de Vijver et al. data set (an de Vijver et al. 2002; FIG. 8B). In addition, elevated FOXC1 expression, which was positively associated with brain metastasis (P=0.02) and inversely associated with bone metastasis (P=0.0002) in the 286-sample Wang et al. data set (Wang et al. 2005), significantly correlated with shorter brain metastasis—free survival (P<0.0001; FIGS. 8C and D).

Example 2

Quantitative Measurement of FOXC1 Expression Using RT-PCR can be Used to Accurately Diagnose Basal-Like Breast Cancer Gene expression analysis has classified breast cancer into five molecular subtypes. Basal-like breast cancer comprises up to 15%-25% of all breast cancers and is associated with the worst overall survival. As described in the example above, FOXC1 is a theranostic biomarker specific for basal-like breast cancer. Semi-quantitative measurement of FOXC1 expression (microarray and immunohistochemistry) has been shown as a reliable method to diagnose basal-like breast cancer. These findings may be extended and further refined by assessing FOXC1 expression using qRT-PCR to provide a more quantitatively accurate assay for diagnosing basal-like breast cancer.

Quantitative RT-PCR gene expression data from 279 formalin-fixed paraffin embedded (FFPE) breast tumors were obtained from a publicly available database (J Clin Oncol. 2009 Mar. 10; 27(8):1160). The receiver operating curve-area under the curve (ROC-AUC) was determined for FOXC1. A cut-off level was determined to optimize sensitivity and specificity.

Figure 10:
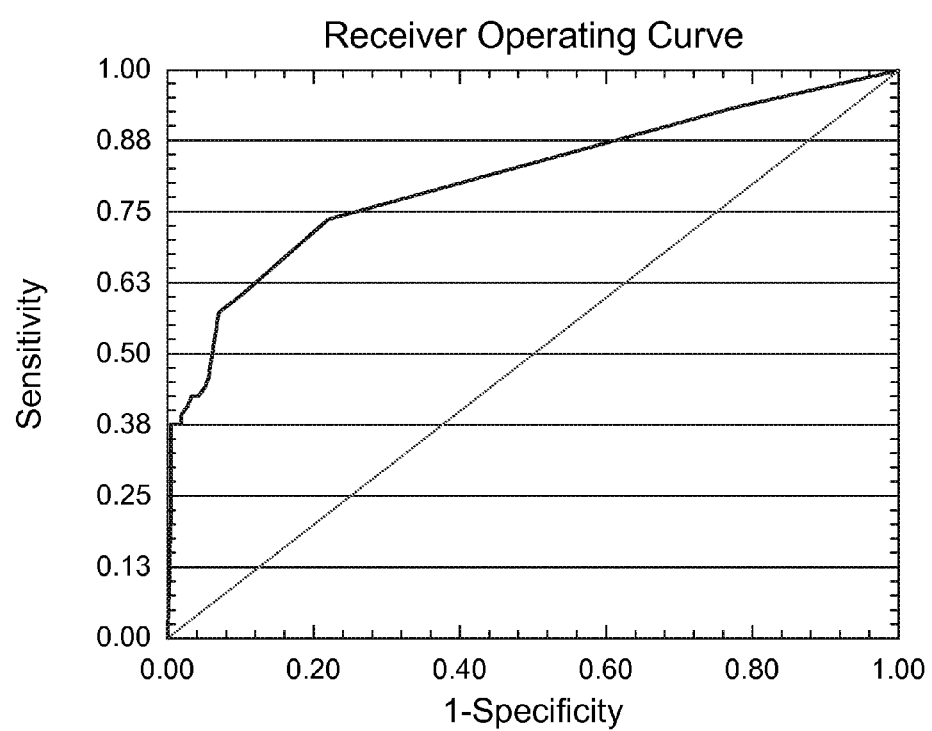
FIG. 10 is a receiver operator curve (ROC)-area under curve (AUC) for FOXC1 expression in predicting basal-like breast cancer. (Parker et al. 2009)

The ROC-AUC for FOXC1 expression (FIG. 10) in predicting basal-like breast cancer was 0.807. A 74% sensitivity and 78% specificity for identifying basal-like breast cancer was shown when using the 0.437 ($49^{th}$ percentile) cut-off level for FOXC1 expression using qRT-PCR.

Quantitative RT-PCR assessment of FOXC1 is thus proven to be a reliable assay to accurately diagnose basal-like breast cancer. Quantitative RT-PCR assessment of FOXC1 from FFPE breast tumors is proposed to be a useful adjunct to semi-quantitative assays (microarray and immunohistochemistry) for the diagnosis of basal-like breast cancer in routine clinical practice.

Example 3

Prognostic Significance of FOXC1 in Breast Cancer Molecular Subtype Models Utilizing Immunohistochemical Biomarkers In the studies described herein, the Forkhead-box transcription factor FOXC1, essential for mesoderm tissue development, was been shown to be consistently overexpressed at both the mRNA and protein levels in BLBC. Elevated FOXC1 mRNA expression was associated with poor overall survival, independent of other clinicopathologic prognostic variables, including lymph node status. True to a predilection for brain metastasis displayed by patients with BLBC, high FOXC1 mRNA levels were also found to correlate with the incidence of brain metastasis and with significantly shortened brain-metastasis free survival in lymph node negative patients. Furthermore, engineered, ectopic overexpression of FOXC1 in breast cancer cells induced aggressive phenotypic changes such as increased cellular proliferation, migration and invasion. Knockdown of FOXC1 using shRNA in breast cancer cells with high endogenous levels of FOXC1 demonstrated loss of aggressive phenotypic features. These results suggest that FOXC1 is a specific prognostic biomarker for BLBC and plays an important role in regulating aggressive cellular traits associated with this molecular subtype. It may also serve as a suitable target for personalized therapy of patients diagnosed with BLBC. These findings utilizing gene expression profiling strongly support the prognostic significance of FOXC1 mRNA expression in breast cancer. According to the study described below, this finding is translated or corroborated using assays of protein expression, such as immunohistochemistry (IHC). Such an assay would be practical and relevant for implementation into routine clinical practice.

Currently, breast cancer receptor status (ER, PR and HER2) is widely used to perform prognostic stratification. Recent reports have suggested using additional surrogate IHC markers of BLBC in combination to improve prognostic stratification (Rakha et al. 2009; Nielsen et al. 2004; Cheang et al. 2008; Elsheikh et al. 2008). Therefore, three biomarker-based models of prognostic stratification in breast cancer were compared: 1) the classic 3-biomarker panel comprising of ER, PR and HER2, 2) a 5-biomarker panel comprising of the above receptors in combination with traditional basal-like biomarkers, basal CK5/6 and CK14, and 3) a 4-biomarker panel comprising of ER, PR, and HER2, in combination with FOXC1.

The primary objective of this study was to establish whether the FOXC1 IHC assay has prognostic value in breast cancer. The secondary objective was to compare the prognostic value of molecular subtype models using surrogate IHC biomarkers in breast cancer.

Methods
Patients.

Review of a prospectively acquired institutional database identified 904 patients with primary infiltrating ductal breast cancer diagnosed between Jan. 1, 1995 and Dec. 31, 2004. Patients who were diagnosed with stage IV breast cancer at initial presentation and who did not undergo primary surgical therapy at John Wayne Cancer Center institution were excluded from the analysis.

Translational Study Design.

This translational study was performed with institutional review board approval and is reported according to the Reporting Recommendations for Tumor Marker Prognostic Studies (REMARK) (McShane et al. 2005). Laboratory personnel, who remained blinded to patient clinical data and outcomes, performed all IHC assays. Assay results were interpreted and scored by a single pathologist (JMS) who remained blinded to the clinical and pathologic data. The design and statistical plan were finalized before merging the above generated assay results with the clinical data, prior to performance of data analysis.

Immunohistochemistry Protocols.

A board-certified pathologist fellowship trained in breast pathology (JMS), who remained blinded to the clinical and pathologic data reviewed IHC (ER, PR, HER2) slides selected randomly from each pre-designated group of patients based on receptor status. Approximately 20% of the study cohort had such verification of receptor status performed. This was done as an internal quality control measure to ensure that the ER, PR and HER2 status of patients at the time of performance of this study was in agreement with that initially rendered at the time of initial diagnosis. No significant difference was encountered in the course of this quality control exercise. Biomarker expression status based on IHC assays was scored using criteria from published guidelines. ER and PR status were considered positive if immunostaining was seen in >10% of tumor nuclei. HER2 status was considered positive if immunostaining was scored as 3+ according to HercepTest criteria. For an equivocal result (2+), HER2 status was considered positive if the fluorescent in situ hybridization (FISH) assay revealed a HER2:chromosome 17 amplification ratio $\geq 2.2$ (Yaziji et al. 2004).

Archival formalin-fixed paraffin embedded (FFPE) tissue blocks for patients designated to be triple-negative with respect to hormone receptor status, i.e., for those who were $ER^-/PR^-/HER2^-$ were then obtained. Tissue blocks were sectioned into serial 5 μm thick tissue sections and subjected to IHC analysis for CK5/6 (D5 and 16B4, Cell Marque Corp, Rocklin, Calif.; no dilution), CK 14 (VP-C410, Vector Laboratories, Burlingame, Calif.; dilution 1:20) and FOXC1 (Ray et al. 2010). Semiquantitative analysis was performed by one pathologist (JMS) blinded to clinical and pathological data who scored the intensity of immunoreactivity on a scale of 0 (no staining) to 3 (strong staining). CK5/6 and CK14 stains were considered positive if any cytoplasmic and/or membranous invasive carcinoma cellular staining was observed (Nielsen et al 2004). FOXC1 protein expression status was considered positive only if any nuclear staining of tumor cells was observed (Ray et al. 2010).

Immunohistochemcial Definition of Breast Cancer Molecular Subtypes.

For purposes of this study, breast cancer molecular subtypes were defined utilizing surrogate IHC biomarker panels as has been earlier reported (Nielsen et al. 2004). ER and HER2 status were used to define luminal ($ER^+/HER2^-$), luminal/$HER2^+$ ($ER^+/HER2^+$), $HER2^+$ ($ER^-/HER2^+$) and basal-like ($ER^-/IHER2^-$) molecular subtypes. In addition to assessing the prognostic significance of FOXC1 protein expression in breast cancer, the prognostic significance of three separate surrogate IHC biomarker panels was also compared and used to define BLBC: 1) the triple negative phenotype or TNP, defining BLBC as being negative for the routinely tested receptor biomarkers ER, PR and HER2, 2) a 5-biomarker panel comprising of TNP combined with CK5/6 and CK14, defining BLBC as being negative for ER, PR and HER2 and positive for either CK5/6 and/or CK14 expression, and 3) a 4-biomarker panel comprising of TNP and FOXC1, defining BLBC as being negative for ER, PR and HER2 and positive for FOXC1 protein expression. In the 5-biomarker and 4-biomarker models, the subset of TNP patients negative for all biomarkers are referred to as 5NP and 4NP, respectively.

Statistical Analysis.

All statistical analyses were performed using SAS (version 9.1.3, SAS, Cary, N.C.). Criteria used to determine positive or negative status of a specific biomarker were determined prior to performing any statistical analysis. Analysis of categorical variables was performed using $\chi^2$ test and Fisher's exact test. The Mann-Whitney U test was employed to compare non-normal continous variables. For survival analysis, overall survival (OS) was the outcome measure used. Survival time was calculated as the date of diagnosis until the date of death. Survival times were censored if the patient was still alive on Oct. 15, 2009 (the last date of update of the database).

Univariate survival curves were generated by the Kaplan-Meier method (Bland et al. 1998) and significance determined using the log-rank test (Bland J M, Altman D G. The logrank test. BMJ 2004; 328:1073). Multivariate analysis was performed using Cox's proportional hazards analysis. For purposes of evaluating the prognostic significance of each of the above IHC biomarker panel definitions of BLBC, three separate models were constructed for the 3-biomarker, 5-biomarker and 4-biomarker definitions of BLBC. The three different multivariate models were compared using the likelihood ratio test and Akaike's Information Criterion (AIC) (Akaike 1974). In addition, we all hypotheses were tested using the Wald test (Cox 1974) and associated P value. All tests were two-sided and P values <0.05 were considered statistically significant.

Results and Discussion

Figure 15:
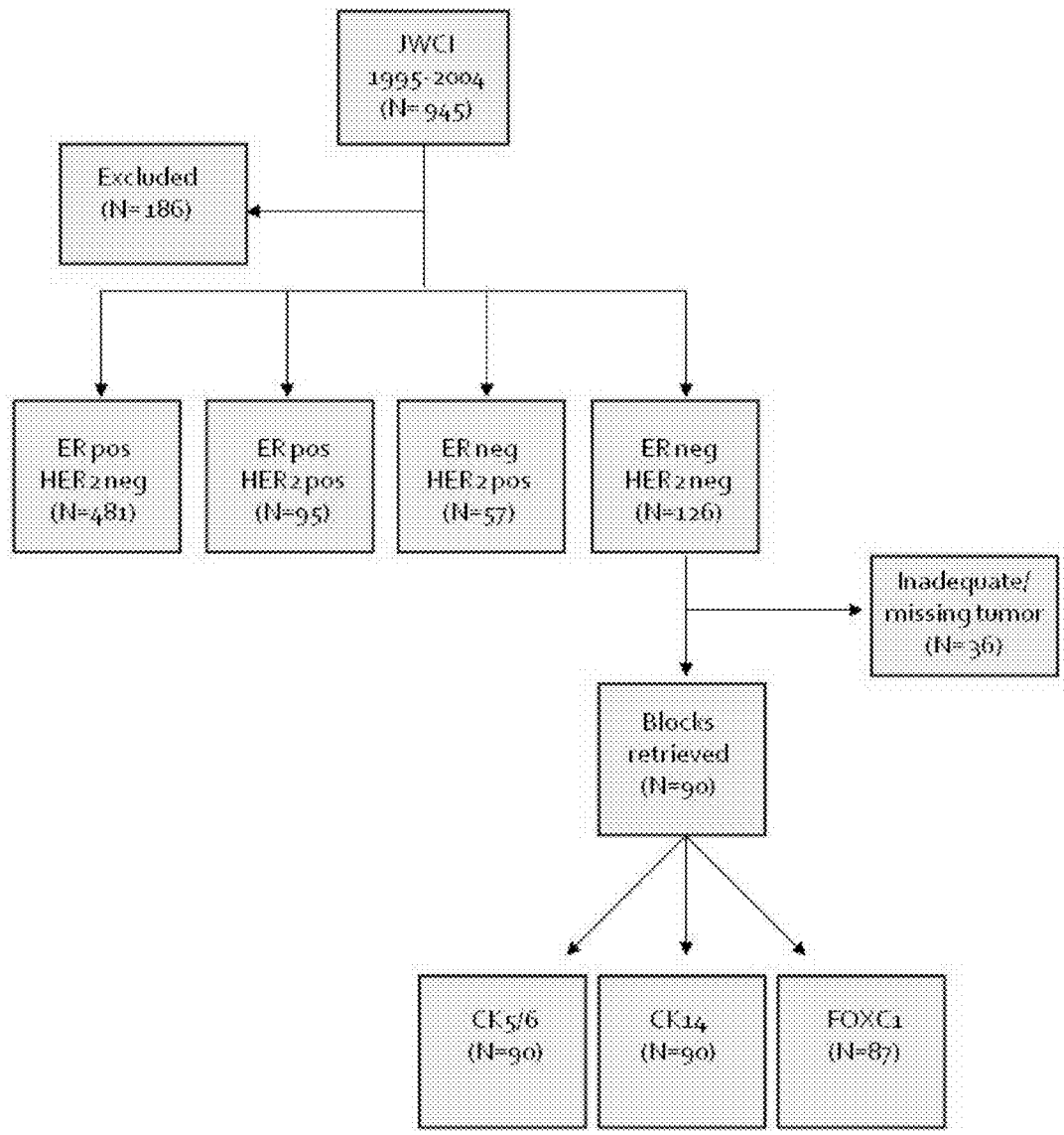
FIG. 15 is a flow diagram of patient identification, sample collection and tissue processing for immunohistochemical assessment of ER, PR, HER2, CK5/6, CK14 and FOXC1.

In this series of 904 patients diagnosed with primary invasive ductal adenocarcinoma of the breast (FIG. 15), all patients had pre-existing data with regard to IHC detection of ER, PR and HER2 receptor status. Patients who were diagnosed with stage IV breast cancer at initial presentation (n=19), who did not undergo primary surgical therapy at John Wayne Cancer Institue (n=125), were excluded from the analysis. The final sample size of the study cohort was 759.

Clinicopathologic Features of Study Cohort.

Clinicopathologic features of the 759 patients included in this study appear in Table 7 (below) classified according to ER and HER2 status, approximating the molecular subtypes.

TABLE 7

Clinical and histopathologic characteristics of the patient cohort - T stage and nodal status are based on final pathologic assessment.

| Subtype | Luminal (ER$^+$/HER2$^-$) n = 481 (63.3%) | Luminal/HER2 (ER$^+$/HER2$^+$) n = 95 (12.5%) | HER2 (ER$^-$/HER2$^+$) n = 57 (7.5%) | Basal-like (ER$^-$/HER2$^-$)n = 126 (16.7%) |
|---|---|---|---|---|
| Age (mean ± SD) | 58.3 ± 13.5 | 52.0 ± 11.7 | 53.5 ± 10.4 | 56.1 ± 15.2 |
| Tumor size | | | | |
| 0-2 cm | 356 (74.0) | 56 (59.0) | 31 (54.4) | 68 (54.0) |
| 2-5 cm | 102 (21.2) | 27 (28.4) | 17 (29.8) | 40 (31.7) |
| >5 cm | 13 (2.7) | 10 (10.5) | 4 (7.0) | 15 (11.9) |
| Unknown | 10 (2.1) | 2 (2.1) | 5 (8.8) | 3 (2.4) |
| Nodal status | | | | |
| Negative | 322 (66.9) | 56 (58.9) | 30 (52.6) | 70 (55.6) |
| Positive | 140 (29.1) | 38 (40.0) | 26 (45.6) | 48 (38.1) |
| Unknown | 19 (4.0) | 1 (1.1) | 1 (1.8) | 8 (6.3) |
| Tumor grade | | | | |
| 1 | 149 (31.0) | 1 (1.0) | 0 (0) | 1 (0.8) |
| 2 | 225 (46.8) | 30 (31.6) | 8 (14.0) | 11 (8.7) |
| 3 | 101 (21.0) | 62 (65.3) | 47 (82.5) | 109 (86.5) |
| Unknown | 6 (1.2) | 2 (2.1) | 2 (3.5) | 5 (4.0) |
| Hormonal therapy | | | | |
| No | 96 (20.0) | 16 (16.8) | 48 (84.2) | 85 (67.5) |
| Yes | 328 (68.2) | 67 (70.5) | 3 (5.3) | 9 (7.1) |
| Unknown | 57 (11.9) | 12 (12.5) | 6 (10.5) | 32 (25.4) |
| Chemotherapy | | | | |
| No | 238 (49.5) | 21 (22.1) | 8 (14.0) | 24 (19.1) |
| Yes | 174 (36.2) | 69 (72.6) | 43 (75.5) | 67 (53.2) |
| Unknown | 69 (14.4) | 5 (5.3) | 6 (10.5) | 35 (27.8) |
| Herceptin therapy | | | | |
| No | — | 65 (68.4) | 34 (59.7) | — |
| Yes | — | 21 (22.1) | 14 (24.6) | — |
| Unknown | — | 9 (9.5) | 9 (15.8) | — |

Figure 16:
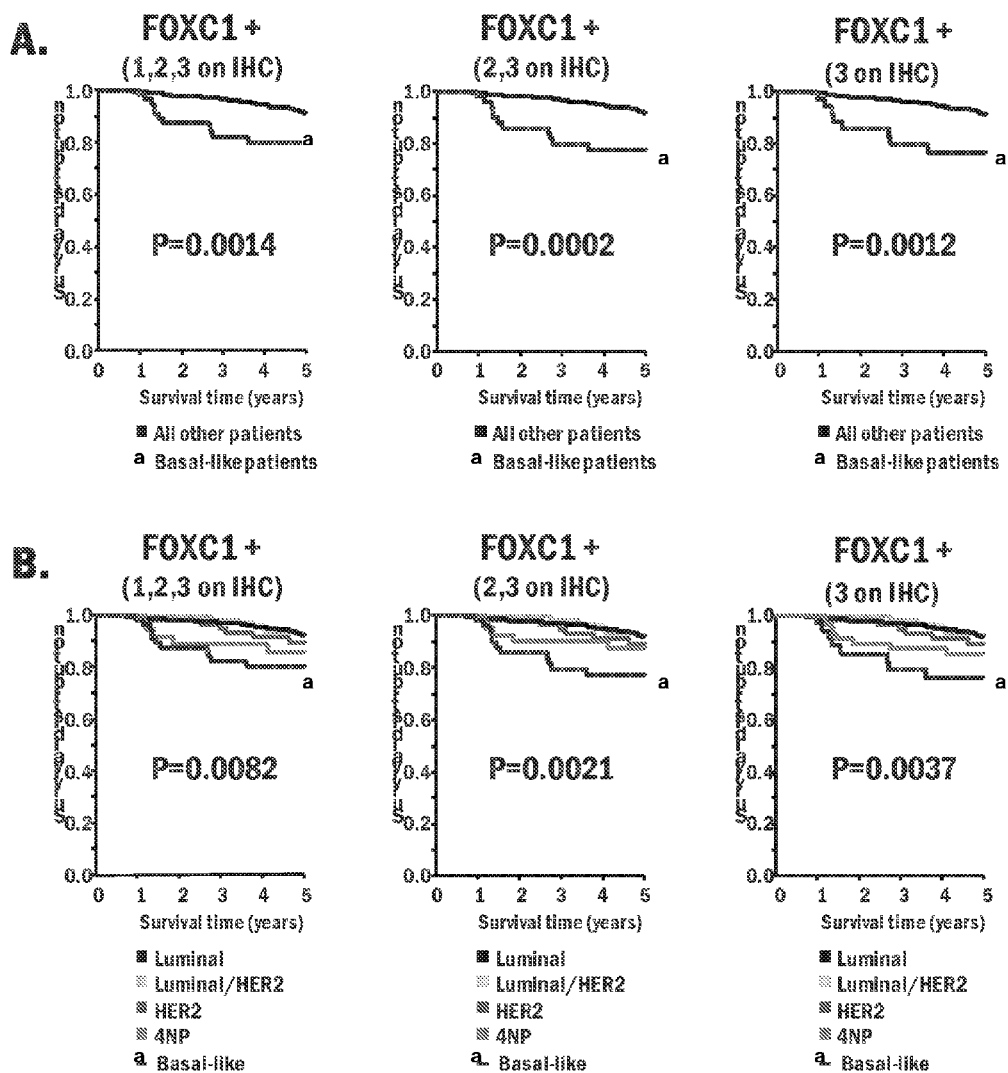
FIG. 16 shows Kaplan Meier curves of 5-year overall survival of breast cancer patients grouped according to (A) FOXC1 protein expression status as assessed on standard immunohistochemistry, wherein positive expression of FOXC1 was shown to be a significant predictor of overall survival, independent of the cutoff value employed; and (B) surrogate immunohistochemical biomarker models of molecular subtype utilizing 3 different cutoff values to define positive expression of FOXC1. Level of protein expression as assessed by IHC was given a score of 0 (negligible or no expression) to 3 (high expression). The three cutoff values were: 0 vs. 1, 2, 3; 0, 1 vs. 2, 3; or 1, 2, 3 vs. 3.
Figure 26:
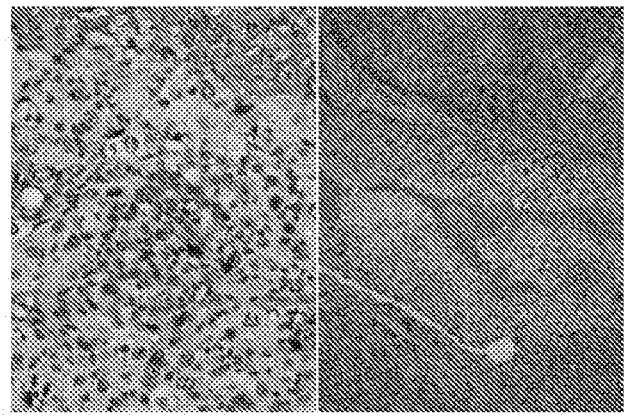
FIG. 26 shows representative immunostaining profiles of CK5/6, CK14 and FOXC1 in FFPE breast cancer specimens according to molecular subtype.
Figure 26:
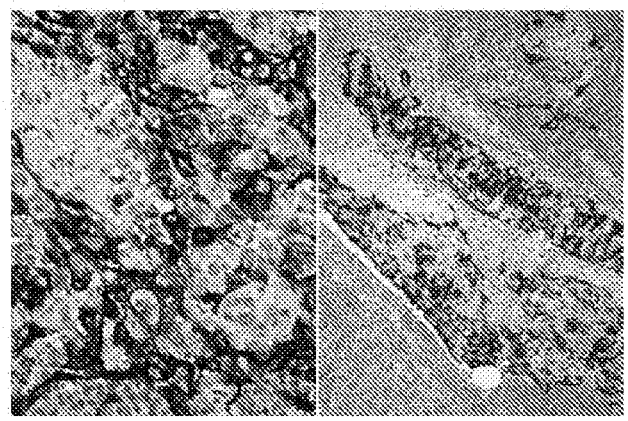
Figure 26:
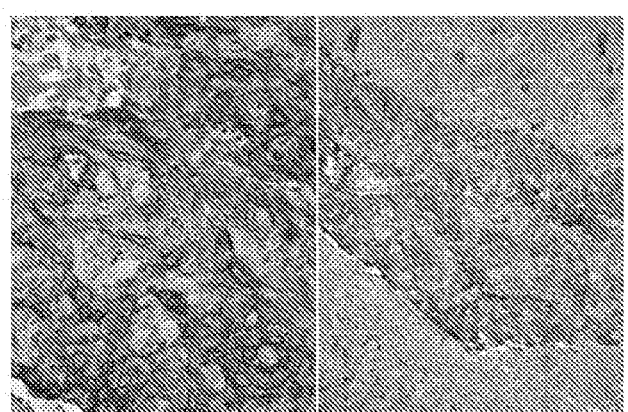

As illustrated in Table 7, 63.3% (481 of 759) were defined as having Luminal (ER+/HER2−) subtype, 12.5% (95 of 759) as having Luminal/HER2 (ER+/HER2+) subtype, 7.5% (57 of 759) as having HER2 (ER−/HER2+) subtype and 16.7% (126 of 759) were defined as being BLBC by the TNP definition (3-biomarker panel). 90 of these 126 specimens underwent additional IHC assays performed for assessment of CK5/6, CK14 and FOXC1. Analyses were not performed for the 36 remaining specimens because of exhaustion of invasive tumor tissue, inadequate remaining invasive tumor in the tissue block or technical issues. 60 of 90 TNP patients were BLBC by the basal cytokeratin definition (5-biomarker panel), and 55 of 87 TNP patients were basal-like by the FOXC1 definition (4-biomarker panel). Clinicopathologic features of the TNP patients classified according to either the 5-biomarker panel or the 4-biomarker panel appear in Table 8 below. Representative IHC images of FFPE sections stained with CK5/6, CK14 or FOXC1 are shown in FIG. 26.

was retained regardless of the cutoff point used to segregate patients into FOXC1 positive and FOXC1 negative subsets (Table 9, FIG. 16). The prognostic significance of FOXC1 protein expression as an independent predictor of OS persisted on multivariate analysis, whereas both the triple negative phenotype as well as the basal cytokeratin positive phenotypes no longer remained significant on multivariate analysis (Table 10). Again, the prognostic significance of FOXC1 as an independent predictor of OS on multivariate analysis was also retained regardless of the cutoff point used to segregate patients into FOXC1 positive and FOXC1 negative subsets. The optimal cutoff point for FOXC1 protein expression scored on IHC in this study was 0-1 (n=42) versus 2-3 (n=49), although FOXC1 protein expression remained a highly significant prognostic marker at all cutoff points tested (0 versus 1-3, 0-1 versus 2-3 and 0-2 versus 3).

TABLE 8

Clinicopathologic characteristics of patient subset with triple negative breast cancer.

|  | Basal CK− n = 38 (5.6%) | Basal CK+ n = 60 (8.9%) | p-value | FOXC1− n = 42 (6.3%) | FOXC1+ n = 49 (8.2%) | p-value |
|---|---|---|---|---|---|---|
| Age (mean ± SD) | 59.7 ± 14.4 | 55.9 ± 16.6 | 0.2429 | 63.2 ± 15.2 | 51.5 ± 14.4 | 0.0003 |
| Tumor size |  |  |  |  |  |  |
| 0-2 cm | 24(63.2) | 25(41.7) |  | 19(45.2) | 23(46.9) |  |
| 2-5 cm | 7(18.4) | 26(43.3) |  | 14(33.3) | 19(38.8) |  |
| >5 cm | 7(18.4) | 7(11.7) |  | 8(19.1) | 6(12.3) |  |
| Unknown |  | 2(3.3) |  | 1(2.4) | 1(2.0) |  |
| Nodal status |  |  |  |  |  |  |
| Negative | 21(55.3) | 32(53.4) |  | 23(54.7) | 26(53.1) |  |
| Positive | 15(39.5) | 23(38.3) |  | 13(31.0) | 22(44.9) |  |
| Unknown | 2(5.3) | 5(8.3) |  | 6(14.3) | 1(2.0) |  |
| Tumor grade |  |  |  |  |  |  |
| 1 | 1(2.6) | 0(0) |  | 0(0) | 0(0) |  |
| 2 | 4(10.5) | 4(6.7) |  | 6(14.3) | 2(4.1) |  |
| 3 | 32(84.2) | 54(90.0) |  | 35(83.3) | 45(91.8) |  |
| Unknown | 1(2.6) | 2(3.3) |  | 1(2.4) | 2(4.1) |  |
| Hormonal therapy |  |  |  |  |  |  |
| No | 23(60.5) | 39(65.0) |  | 25(59.6) | 32(65.3) |  |
| Yes | 4(10.5) | 1(1.7) |  | 3(7.1) | 1(2.0) |  |
| Unknown | 11(29.0) | 23(33.3) |  | 14(33.3) | 16(32.7) |  |
| Chemotherapy |  |  |  |  |  |  |
| No | 9(23.7) | 9(15.0) |  | 9(21.4) | 5(10.2) |  |
| Yes | 17(44.7) | 30(50.0) |  | 17(40.5) | 28(57.1) |  |
| Unknown | 12(31.6) | 21(35.0) |  | 16(38.1) | 16(32.7) |  |

**p value

Prognostic Value of FOXC1 Protein Expression in Breast Cancer.

In the present study, FOXC1 status was considered positive only if any nuclear staining was observed (Ray et al. 2010). Positive expression of FOXC1 protein was found to be a significant predictor of overall survival (FIG. 16) amongst breast cancer patients on univariate analysis (HR 3.364 95% CI 1.758-6.438, P=0.0002) (Table 9-10). Other standard clinicopathologic factors such as age, tumor size, nodal status and tumor grade were also found to be significant predictors of overall survival. Adjuvant treatment variables such as hormonal therapy, chemotherapy or trastuzumab (herceptin) therapy were not significant predictors of overall survival, indicating equivalent effects across all groups. Furthermore, the prognostic significance of FOXC1 on univariate analysis

TABLE 9

Univariate cox regression analysis of the prognostic significance of individual clinicopathologic and treatment variables on 5 year overall survival.

|  | N | P-value | Hazard ratio (95% CI) |
|---|---|---|---|
| Age | 759 | <0.0001 | 1.046 (1.028 1.064) |
| Tumor Size (>=5, 2-4.99, 0-2) | 739 | 0.0006 | 1.826 (1.293 2.580) |
| Nodal Status (Positive vs. Negative) | 730 | 0.0113 | 1.913 (1.158 3.164) |
| Tumor Grade (1, 2, 3) | 744 | 0.0313 | 1.468 (1.035 2.082) |
| ER−/HER2− vs. others | 759 | 0.0104 | 2.027 (1.181 3.480) |
| Basal+ vs. others | 731 | 0.0043 | 2.572 (1.344 4.919) |
| FOXC1+ (1, 2, 3) vs. others | 724 | 0.0014 | 2.880 (1.505 5.510) |

TABLE 9-continued

Univariate cox regression analysis of the prognostic significance of individual clinicopathologic and treatment variables on 5 year overall survival.

|  | N | P-value | Hazard ratio (95% CI) |
|---|---|---|---|
| FOXC1+ (2, 3) vs. others | 724 | 0.0002 | 3.364 (1.758 6.438) |
| FOXC1+ (3) vs. others | 724 | 0.0012 | 3.392 (1.618 7.112) |
| Hormone Therapy (yes vs. no) | 652 | 0.1213 | 0.660 (0.390 1.116) |
| Chemotherapy (yes vs. no) | 644 | 0.2512 | 0.733 (0.432 1.245) |
| Herceptin Therapy (yes vs. no) | 688 | 0.6389 | 1.275 (0.462 3.524) |

TABLE 10

Multivariate cox regression analysis of the prognostic significance of individual clinicopathologic and treatment variables on 5 year overall survival.

|  | N | P-value | Hazard ratio (95% CI) |
|---|---|---|---|
| Age | 670 | <0.0001 | 1.049 (1.028 1.069) |
| Tumor Size (>=5, 2-4.99, 0-2) |  | 0.0022 | 1.797 (1.234 2.618) |
| Nodal Status (Positive vs. Negative) |  |  |  |
| Tumor Grade (1, 2, 3) |  |  |  |
| ER−/HER2− vs. others |  |  |  |
| Basal+ vs. others |  |  |  |
| FOXC1+ (1, 2, 3) vs. others |  | *0.0005 | 3.406 (1.713 6.775) |
| FOXC1+ (2, 3) vs. others |  | *0.0001 | 3.839 (1.928 7.645) |
| FOXC1+ (3) vs. others |  | *0.0019 | 3.755 (1.632 8.636) |
| Hormone Therapy (yes vs. no) |  |  |  |
| Chemotherapy (yes vs. no) |  |  |  |
| Herceptin Therapy (yes vs. no) |  |  |  |

Overall Survival According to IHC Models of Breast Cancer Molecular Subtype.

Figure 17:
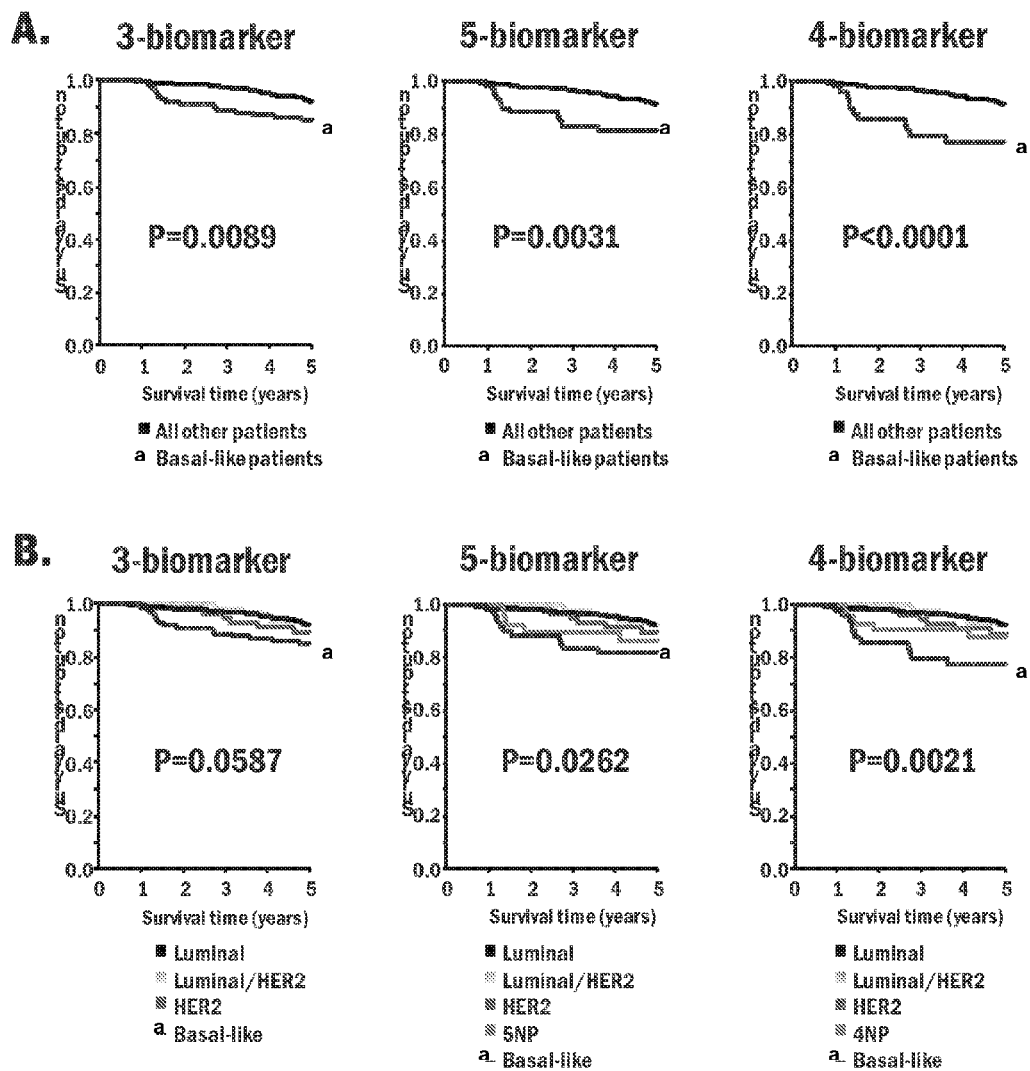
FIG. 17 shows Kaplan Meier curves of 5-year overall survival of breast cancer patients grouped according to (A) Triple negative phenotype (TNP) status, Basal cytokeratin (CK) expression status and FOXC1 protein expression status as assessed on standard immunohistochemistry; and (B) 3 surrogate immunohistochemical biomarker panel models of breast cancer molecular subtype—1) the classic 3-biomarker panel comprising of ER, PR and HER2, 2) a 5-biomarker panel comprising of the above receptors in combination with traditional basal-like biomarkers, basal CK5/6 and CK14, and 3) a 4-biomarker panel comprising of ER, PR and HER2, in combination with FOXC1.

The breast cancer subtypes as defined by the surrogate IHC biomarker panels differed significantly in predicting OS (FIG. 17). The model utilizing FOXC1 achieved the most significant degree of prognostic stratification (p<0.0001). In the 3-biomarker panel, the 5-year and 10-year OS for BLBC patients (defined using TNP) was 85% and 77%, respectively. In the 5-biomarker panel, the 5-year and 10-year OS for BLBC patients (defined using TNP+CK5/6 and CK14_was 82% and 66%, respectively. In the 4-biomarker panel, the 5-year and 10-year OS for BLBC patients (defined using TNP+FOXC1) was 77% and 69%, respectively.

On univariate Cox regression analysis, in addition to standard clinicopathologic factors such as age, tumor size, lymph node status and tumor grade, BLBC defined according to the 3-biomarker, 5-biomarker and 4-biomarker panels were all significant predictors of breast cancer OS (Table 9, above). On multivariate Cox regression analysis, only age, tumor size and BLBC defined according to the 4-biomarker panel based on FOXC1 protein expression retained significance and were independent predictors of OS. The 3-biomarker panel utilizing TNP as well as the 5-biomarker panel based on basal CK expression lost significance on multivariate analysis.

For purposes of evaluating the prognostic significance of each of the above IHC biomarker panel definitions of BLBC, three separate multivariate models of breast cancer molecular subtypes were constructed for the 3-biomarker (based on the triple negative phenotype (TNP)), 5-biomarker (based on expression of basal cytokeratins) and 4-biomarker (based on protein expression of FOXC1) definitions of BLBC, each including the standard clinicopathologic factors age, tumor size, nodal status and tumor grade. The three multivariate models were compared using the likelihood ration test and Akaike's Information Criterion (AIC). The 4-biomarker model based on FOXC1 protein expression had the lowest AIC score indicating it to be the model with the greatest prognostic value (Table 11).

TABLE 11

Comparison of the three different multivariate models of breast cancer molecular subtype utilizing surrogate immunohistochemical biomarker panels.

| 3-biomarker (TNP) prognostic model | N = 702 | P-value | AIC = 748.576 Hazard Ratio (95% CI) |
|---|---|---|---|
| Age |  | <0.0001 | 1.049 1.029 1.069 |
| Tumor Size (>5, 2-4.99, 0-2) |  | 0.0153 | 1.600 1.094 2.338 |
| Nodal Status (positive vs. negative) |  |  |  |
| Tumor Grade (High-3, Intermediate-2, Low-1) |  | 0.0123 | 1.628 1.111 2.385 |
| ER−/HER2− vs. others |  |  |  |
| 5-biomarker (Basal cytokeratin) prognostic model | N = 677 | P-value | AIC = 719.774 Hazard Ratio (95% CI) |
| Age |  | <0.0001 | 1.042 1.022 1.063 |
| Tumor Size (>5, 2-4.99, 0-2) |  | 0.0034 | 1.765 (1207 2.581) |
| Nodal Status (positive vs. negative) |  |  |  |
| Tumor Grade (High-3, Intermediate-2, Low-1) |  |  |  |
| Basal+ vs. others |  | 0.01 | 2.499 1.245 5.016 |
| 4-biomarker (FOXC1) prognostic model | N = 670 | P-value | AIC = 712.989 Hazard Ratio (95% CI) |
| Age |  | <0.0001 | 1.045 1.028 1.069 |
| Tumor Size (>5, 2-4.99, 0-2) |  | 0.0022 | 1.797 1.234 2.618 |
| Nodal Status (positive vs. negative) |  |  |  |
| Tumor Grade (High-3, Intermediate-2, Low-1) |  |  |  |
| FOXC1+ (2, 3) vs. others |  | <0.0001 | 3.839 1.928 7.645 |

In the current study cohort of patients with invasive ductal breast cancer, the basal-like phenotype defined on the basis of positive FOXC1 protein expression was superior to the traditionally employed triple negative phenotype, for purposes of prognostic stratification. This demostrates that being "basal-like" is not synonymous with being "triple-negative." The IHC definition of the basal-like phenotype based on the positive expression of FOXC1 protein was also superior to basal-like phenotype defined by the positive expression of basal CK, for purposes of prognostic stratification. This represents a significant advance as, unlike basal CKs, FOXC1 represents a potential candidate for the targeted personalized therapy of patients with BLBC (Ray et al. 2010). FOXC1 not only promises to be a prognostic biomarker, but a predictive biomarker as well—predictive of the therapeutic efficacy of any future anti-FOXC1 directed drug or biologic for the treatment of patients with basal-like breast cancer.

The tissue microarray platform relies on representative core needle sampling of specimens and is an excellent method for exploratory research projects that considerably minimizes resource allocation. It is ideal for assessing the presence of biomarkers that are expressed homogeneously throughout a specimen such as ER and HER2. However, it is not ideal for assessing the presence of potential biomarkers, such as basal CKs, that are expressed heterogeneously throughout the tissue section (refer Laakso et al.). Therefore, entire tissue sections were used instead of tissue microarrays for the analysis.

The analysis discussed above was restricted to the invasive ductal breast cancer histologic type. This was done to minimize potential confounding effects (prognostic, biologic or both) of histologic subtype on molecular subtype in breast cancer. However, the above findings with regard to FOXC1 protein expression may be extrapolated to other histologic types of breast cancer such as lobular breast cancer.

FOXC1 mRNA expression, is found to have a prognostic impact on OS in breast cancer that is likely independent of lymph node status, and is at least in part attributable to a significantly higher rate of association with the early occurrence of brain metastasis, often as the first site of distant metastasis, even in lymph node negative patients. In the present study, when FOXC1 protein expression status as assessed by IHC was included in the multivariate model, nodal status failed to retain significance. This lends further support to the prognostic impact of FOXC1 being independent of nodal involvement.

The 4-biomarker panel utilizing FOXC1 protein expression showed superior prognostication compared to the 5-biomarker panel utilizing basal CK 5/6 and/or CK14 in the current patient cohort (when considered in combination with ER, PR and HER2 status of breast cancer specimens). This suggests that FOXC1 protein expression, when present, is successful in diagnosing patients possessing the true basal-like molecular subtype from amongst patients with the triple-negative phenotype. A subset analysis of only triple-negative patients in this study cohort displayed a trend towards supporting this conclusion (data not included).

Example 4

FOXC1 Responsible for Aggressive and Invasive Phenotype, Making it a Viable Therapeutic Target Materials and Methods FOXC1-Knockdown Cells.

FOXC1 shRNAs and a control shRNA that does not match any known cDNA were from Sigma. Cells were stably transfected with the FOXC1 or the control shRNA construct and selected with 5 μg/mL puromycin. Pooled knockdown cells were used for experiments.

FOXC1 shRNAs.

The following shRNAs were purchased from Sigma:

```
Mouse FOXC1 shRNA sequences:
                            (shRNA1; SEQ ID NO: 1)
CCGGGAGCAGAGCTACTATCGCGCTCTCGAGAGCGCGATAGTAGCTCTG CTCTTTTG;
and
                            (shRNA2; SEQ ID NO: 2)
CCGGTGGGAATAGTAGCTGTCAGATCTCGAGATCTGACAGCTACTATTC

CCATTTTG.

Human FOXC1 shRNA sequences:
                            (shRNA1; SEQ ID NO: 3)
CCGGCAAGAAGAAGGACGCGGTGAACTCGAGTTCACCGCGTCCTTCTT CTTGTTTTG;
and
                            (shRNA2; SEQ ID NO: 4)
CCGGCCCGGACAAGAAGATCACCCTCTCGAGAGGGTGATCTTCTTGTCC

GGGTTTTT.

Control shRNA (does not target any known human or
mouse gene):
                            (SEQ ID NO: 5)
CCGGCAACAAGATGAAGAGCACCAACTCGAGTTGGTGCTCTTCATCTTG

TTGTTTTT
```

FOXC1-Overexpressing Cells.

A full-length human FOXC1 cDNA was stably transduced into breast cancer cells. Stable cell lines were selected with 800 μg/mL G418. Pooled populations were used for experiments.

Cell Culture.

Cancer cell lines were from American Type Culture Collection. Normal human mammary epithelial cells (HMEC) were from Clonetics. Cell proliferation was assessed by the MTT assay. Three-dimensional cell culture was done using BD Matrigel matrix in 96-well plates.

Cell Migration and Invasion Assay.

Briefly, $10^4$ cells were plated on the top of a Boyden chamber inserts with an 8 μm pore size. The inserts were then transferred into a 24-well plate. Each well contained DMEM with 10% serum as the chemoattractant. To rule out the effect of cell proliferation, 2 μg/ml mitomycin C was added to the cells. After incubation, cells remaining on the upper surface of the chambers were removed with cotton swabs. Cells on the lower surface of the inserts were stained with the HEMA3 kit (Fisher). The membrane was then mounted onto a microscope slide and the migrating cells were counted in 5 different areas using a light microscope. For invasion assays, inserts were coated with a thin layer of Matrigel basement membrane matrix (BD Biosciences) and the same procedures were followed.

Immunohistochemistry and Immunoblotting were performed as described above.

Results and Discussion

Figure 11:
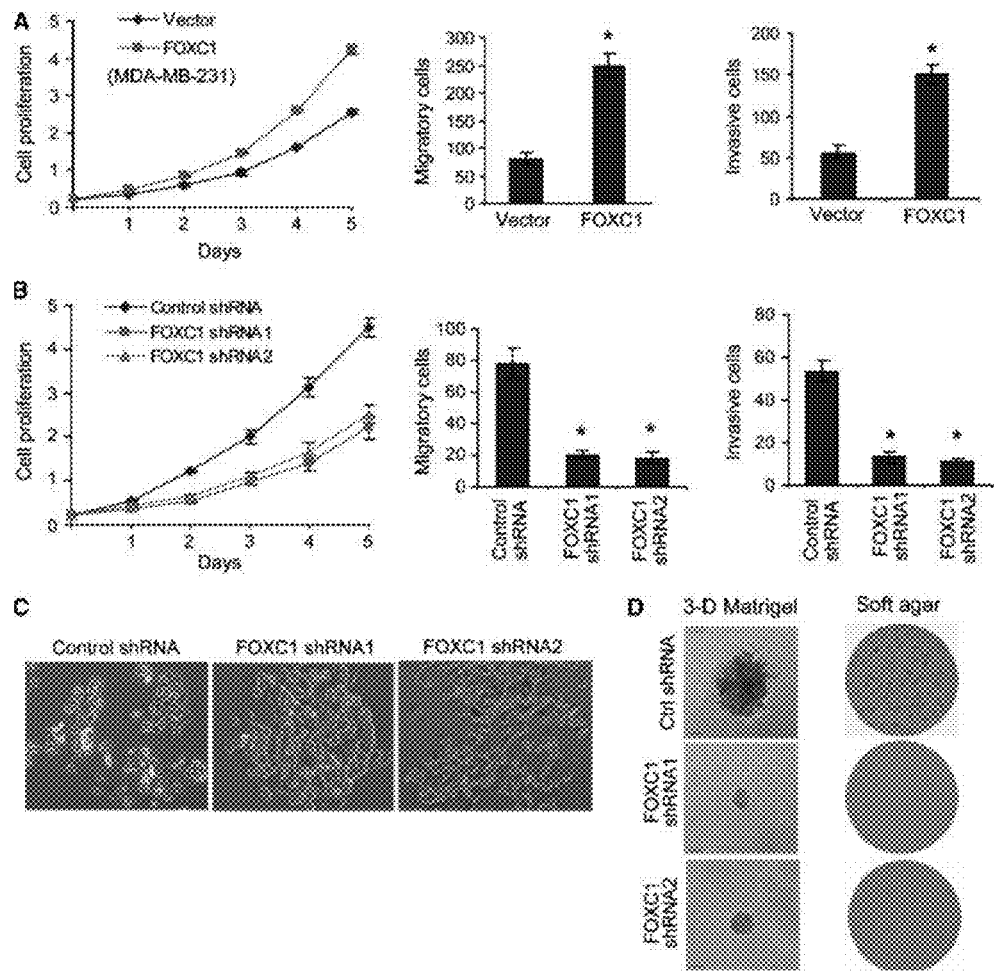
FIG. 11 shows the effects of FOXC1 overexpression and knockdown in breast cancer cells. A, cell proliferation (left), migration (middle), and invasion (right) of FOXC1- or vector-overexpressing MDA-MB-231 cells. Columns, mean (n=3); bars, SD. *, P<0.05, versus the control. B, cell proliferation, migration, and invasion of control or FOXC1 shRNA—expressing 4T1 cells. *, P<0.05, versus the control. C, morphologies of control and FOXC1 shRNA 4T1 cells in monolayer culture. D, representative images of control and FOXC1 shRNA 4T1 cells grown in three-dimensional (3-D) Matrigel (left) and soft agar (right). Bar, 135 µm.
Figure 12:
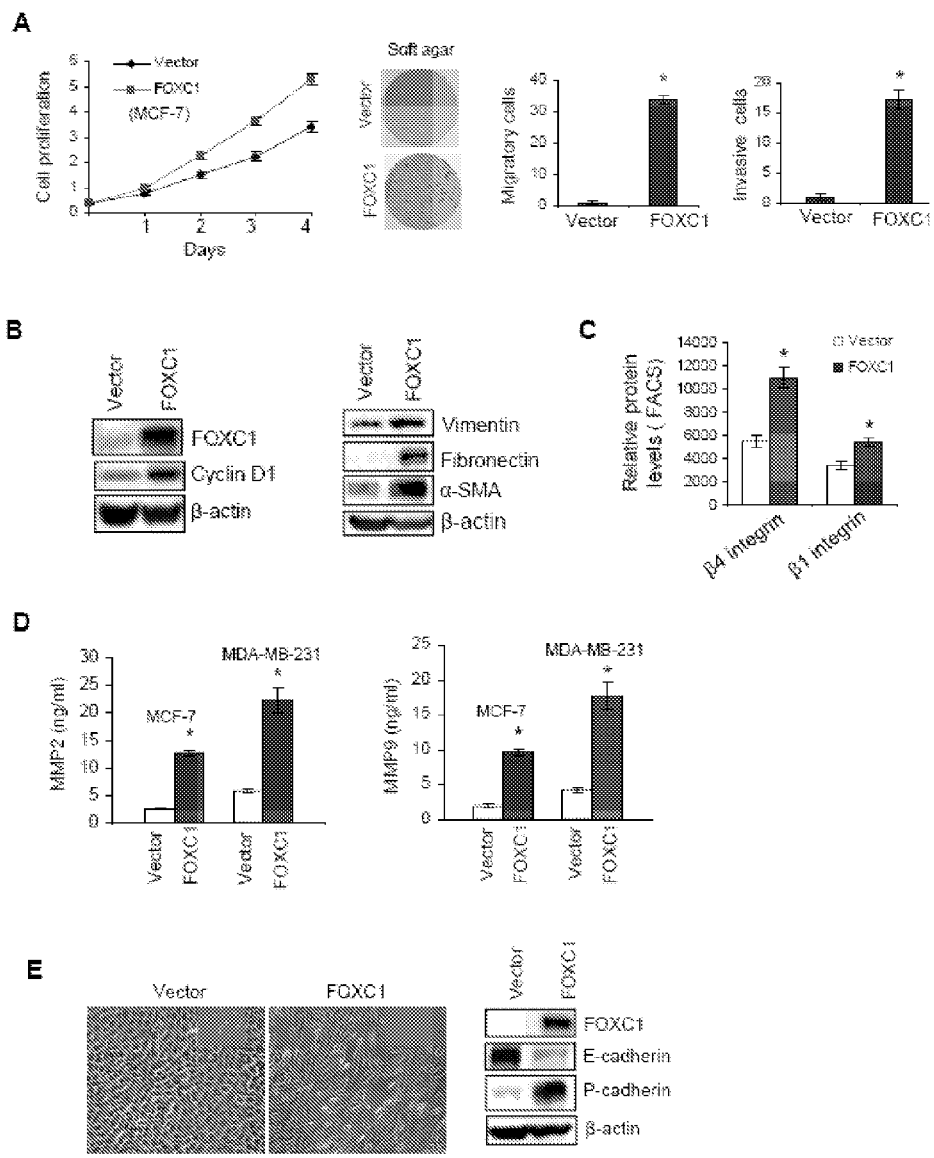
FIG. 12 shows the effects of FOXC1 overexpression in human breast cancer cells and MCF-10A cells. A, FOXC1 was stably transfected into MCF-7 breast cancer cells. Cell proliferation (left), anchorage-independent growth (middle-left), migration (middle-right), and invasion (right) of FOXC1- or vector-expressing cells were measured using MTT, soft agar, and Boyden chamber assays. *, P<0.05 versus the vector control. B, expression of cyclin D1 and fibroblastic markers in MDA-MB-231 cells overexpressing FOXC1 or the control vector was examined by immunoblotting. C, levels of β4 and β1 integrins in MDA-MB-231 cells overexpressing FOXC1 or the control vector were measured by flow cytometry. *, P<0.05 versus the vector control. Of note, same results were obtained with MCF-7 cells. D, expression of MMP2 and MMP9 was measured by ELISA. Each bar represents mean±SD (n=3). *, P<0.05 versus the vector control. E, morphologies of MCF-10A human mammary epithelial cells overexpressing the vector or FOXC1 (left) and immunoblotting of luminal (E-cadherin) and basal (P-cadherin) markers in the same cells.

The function of FOXC1 in breast cancer cells was examined. Overexpression of FOXC1 in MDA-MB-231 BLBC cells (harboring moderate levels of endogenous FOXC1) increased cell proliferation, migration, and invasion (FIG. 11A). Similar results were observed in MCF-7 luminal breast cancer cells (harboring undetectable levels of endogenous FOXC1; FIG. 12A). FOXC1 overexpression also enhanced anchorage-independent growth of MCF-7 cells in soft agar. Immunoblotting indicated that cyclin D1, fibroblast markers (vimentin, fibronectin, and α-smooth muscle actin), integrins β4 and β1, and matrix metalloproteinases MMP2 and MMP9 were upregulated by FOXC1 overexpression (FIG. 12B-D). FOXC1 has been shown to induce epithelial-mesenchymal transition (EMT) in MCF-12A mammary epithelial cells (Bloushtain-Qimron et al. 2008-21). Similarly, FOXC1 overexpression in MCF-10A mammary epithelial cells induced a mesenchymal phenotype accompanied by increased expression of the basal marker P-cadherin and decreased expression of the epithelial marker E-cadherin (FIG. 12E). Regulation of these genes by FOXC1 was also confirmed by quantitative reverse transcription-PCR (data not shown). These data suggest that FOXC1 can elicit an aggressive phenotype associated with BLBC cells.

Figure 13:
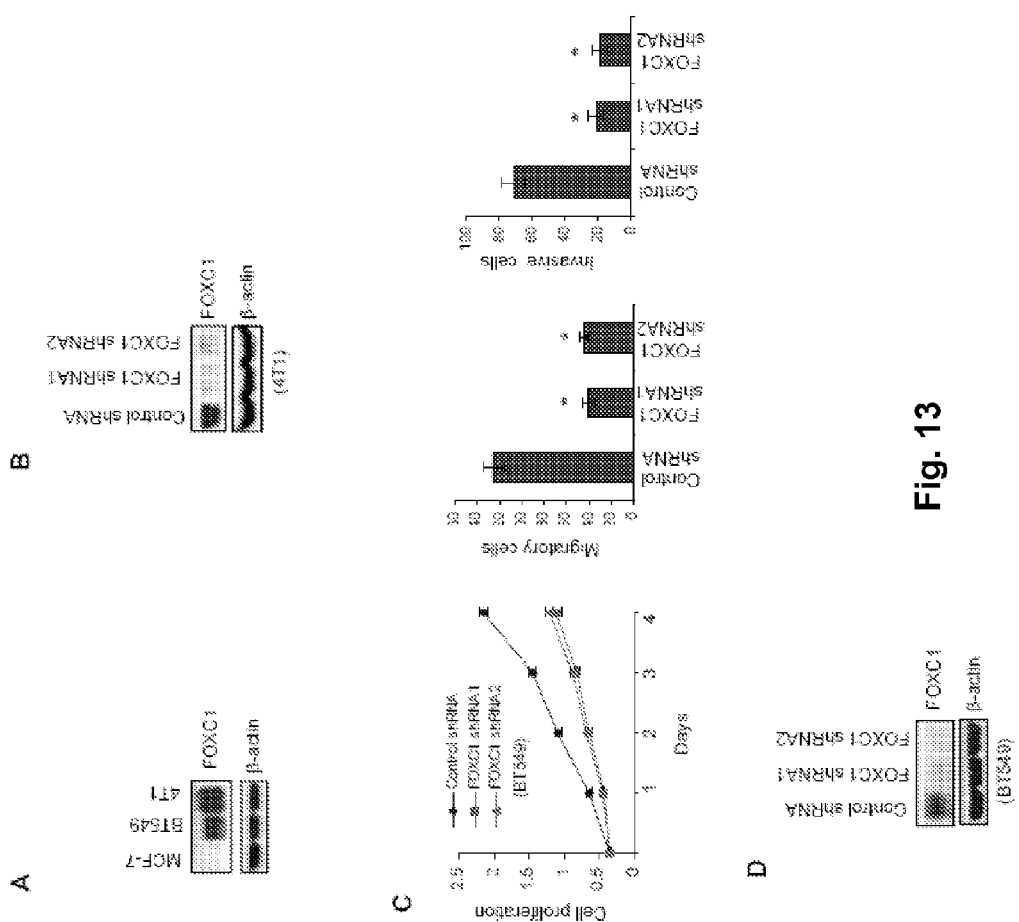
FIG. 13 shows the effects of FOXC1 knockdown in human breast cancer cells. A, FOXC1 protein levels were compared in MCF-7, BT549, and 4T1 breast cancer cells (refer to FIG. 2C). B, immunoblotting of FOXC1 in 4T1 cells expressing control or FOXC1 shRNA. C, cell proliferation (left), migration (middle), and invasion (right) of control or FOXC1 shRNA19 expressing BT549 cells were measured using MTT and Boyden chamber assays. *, P<0.05 versus the control. D, immunoblotting of FOXC1 in BT549 cells expressing control or FOXC1 shRNA.

To assess the effects of FOXC1 depletion, FOXC1 shRNA was stably transduced into 4T1 mouse breast cancer cells, which are a model for stage IV human breast cancer (Aslakson & Miller 1992-22) and possess high levels of endogenous FOXC1 (FIG. 13A). These shRNAs reduced FOXC1 levels by >90% (FIG. 13B) and decreased cell proliferation, migration, and invasion (FIG. 11B). Similar results were obtained with BT549 human breast cancer cells when FOXC1 was reduced by shRNA (FIGS. 13C and D). FOXC1 depletion also converted 4T1 cells from fibroblast-like to epithelial-like and suppressed cell growth in three-dimensional culture and colony formation in soft agar (FIGS. 11C and D). These data further suggest a role of FOXC1 in regulation of cell function. Studies have suggested that BLBC may possess extraordinarily high growth rates (Seewaldt & Scott 2007) and an EMT phenotype (Sarrio et al. 2008) compared with other breast cancer subgroups. FOXC1 may play a role in coordinating these BLBC properties. Further, DNA methylation may play a role in BLBC-associated FOXC1 expression. In summary, these studies support FOXC1 as a theranostic biomarker, i.e., a diagnostic and prognostic biomarker as well as a therapeutic target.

Example 5

FOXC1 Regulation of ERα Expression and Function

Based on the studies below, it was found that FOXC1 induces NF-κB signaling to inhibit ERα expression. This study provides a molecular basis for the ERα-negative phenotype of basal-like breast cancer and also provides implications for the role of FOXC1 in the response of breast cancer cells to antiestrogen treatment.

Materials and Methods

Cell Culture.

MCF-7 and T47D human breast cancer cell lines were obtained from the Breast Center at Baylor College of Medicine. Cells were routinely maintained in Dulbecco's modified Eagle's medium (DMEM) supplemented with 10% fetal bovine serum (FBS), 2 mM glutamine, 50 IU/ml of penicillin, 50 µg/ml of streptomycin, and 10 µg/ml insulin. Cells were kept at 37° C. in a humidified incubator with 5% $CO_2$. Tamoxifen and 17β-estradiol were from Sigma (St Louis, Mo.). The IKK small molecule inhibitor BMS-345541 was purchased from Calbiochem (Gibbstown, N.J.). For experiments involving estradiol and tamoxifen, cells were serum-starved overnight and then stimulated with the ER ligands for different time periods prior to cell proliferation assays.

Microarray Data Analysis.

Raw expression data from publicly available human breast cancer gene expression microarray data sets (Ginestier et al., 2006; Lu et al., 2008; Perou et al., 2000; Pollack et al., 2002; Richardson et al., 2006; Schuetz et al., 2006; Sorlie et al., 2001; Sorlie et al., 2003; Zhao et al., 2004) and the Oncology—Breast Samples Project database (Bittnet et al.) of the International Genomics Consortium (IGC) at https://expo.intgen.ora/expo/public were analyzed using Oncomine 4.0 software.

Stable Transfection.

MCF-7 and T47D cells were stably transfected for 24 h with a FLAG-tagged FOXC1 construct or the empty vector using Lipofectamine 2000 reagent (Invitrogen). Stable clones were then selected using 800 µg/ml G418 (Invitrogen). Expression of FLAG-FOXC1 was verified by western blotting with an anti-FOXC1 antibody (Santa Cruz Biotechnology, Santa Cruz, Calif.) and an anti-FLAG antibody (Origene, Rockville, Md.).

Transient Transfection.

MCF-7 cells were grown for 48 h till 80% confluence before transfection. For cotransfections, 0.1 µg DNA of ERE-tk-luc or NF-κB-luc (Promega, Madison, Wis.) reporter construct and 1 µg of FLAG-FOXC1 or NF-κB p65 vector was added to 60 mm dishes. The transfected cells were cultured for 24 h. The estrogen-responsive reporter plasmid ERE-tk-luc contains a single consensus ERE upstream of a minimal thymidine kinase promoter and the luciferase gene (Cui et al., 2003). At 24 h after transfection, cells were washed twice with PBS and harvested in 200 µl of reporter lysis buffer (Promega). Twenty nanograms of a β-galactosidase expression vector pSV-β-Gal (Promega) were co-transfected as an internal control. Luciferase and β-galactosidase assays were performed using Promega reporter assay reagents and the GloMax Multi-detection system. To test whether p65 overexpression inhibits ERα expression, MCF-7 cells were transfected with a p65 construct or the vector for 48 h, followed by immunoblotting.

Immunoblot Analysis.

Whole cell lysates for western blotting were generated by cell lysis buffer (50 mM Tris-HCl, pH 7.4, 150 mM NaCl, 2 mM EDTA, 1% NP-40, 10% glycerol) supplemented with a protease inhibitor cocktail (Sigma, St Louis, Mo.). Equal amounts of protein were separated by 10% SDS-PAGE and then transferred onto a nitrocellulose membrane. The remaining steps were conducted according to a standard immunoblotting protocol (Qu et al., 2009). Immunoblotting was done with polyclonal antibodies against p65, FOXC1, IRS1 (1:200; Santa Cruz Biotechnology), polyclonal antibodies against phospho-p65, p50, IκBα (1:1000; Cell Signal), or monoclonal antibodies against ERα (1:500; Novocastra Laboratories, Newcastle upon Tyne, UK), PR (1:500; DAKO, Carpinteria, Calif.). Anti-β actin (Sigma) was used at a 1:10000 dilution. After the primary antibody incubation, the membrane was again washed with PBST three times (5 min each) and then incubated with a horseradish peroxidase (HRP)-linked secondary antibody (Amersham, Piscataway, N.J.) at a dilution of 1:4000 in blocking solution. The membrane was washed and bands were visualized using chemiluminescence assays.

Real-Time Reverse Transcription-PCR.

Total RNA was isolated from breast cancer cells using the RNeasy mini kit (Qiagen, Valencia, Calif.). PCR amplification was performed by using Rotor-Gene 3000 Real Time PCR System (CoRbett Research) in a 25-µL reaction volume. The PCR mixture contained SuperScript® III Reverse Transcriptase, TaqMan probe, and forward and reverse primers. Samples were incubated for 1 cycle at 95° C. for 2 min, 40 cycles at 95° C. for 30 s, and 60° C. for 60 s. All samples were run in triplicate. Results were analyzed by using the Rotor-Gene 3000 software package (Corbett Research). Primer information is as follows: FOXC1 forward primer 5'-CGG-TATCC AGCCAGTCTCTGTACCG-3' (SEQ ID NO:6), FOXC1 reverse primer 5'-GTTCGGCTTTGAGGGTGT-GTC-3' (SEQ ID NO:7), ERα forward primer 5'-CGGTTA-GATTCATCATGCGGAACCG-3' (SEQ ID NO:8), and ERα reverse primer 5'-TGTGTAGAGGGCATGGTGGAG-3' (SEQ ID NO:9). ERα and FOXC1 mRNA data were normalized by the β-actin mRNA value.

Immunofluorescence Staining.

MCF-7 cells were transiently transfected with GFP-FOXC1 plasmid for 24 h. Then the cells were digested with trypsin and seeded in chamber slides (BD Biosciences, Franklin Lakes, N.J.). After 12-h incubation, cells were fixed with 4% formaldehyde and then permeabilized with PBS containing 0.1% Triton X-100. Slides were blocked by 5% BSA for 30 minutes and incubated with a primary anti-ERα antibody (1:100) at room temperature for 1 h. Cells were then incubated with an Alexa Fluor 546-conjugated secondary antibody (1:200, Invitrogen) for 30 min. Slides were washed by PBS three times for 5 minutes each, mounted in DAPI, and observed under a high resolution Nikon TI-E microscope.

IPA Signaling Pathway Analysis.

The Richardson et al. data set (Richardson et al., 2006) was subjected to Ingenuity Pathway Analysis (IPA, Ingenuity Systems, Redwood City, Calif.). Briefly, global gene expression profiles of all breast cancer samples were analyzed according to their molecular subgroup (basal-like, HER2 and luminal) with respect to their association with a specific canonical pathway in the Ingenuity Pathways Knowledge Base. The significance of the association between the average global gene expression profile associated with a particular subgroup and the specific canonical pathway was measured in two ways: 1) A ratio of the average number of genes from a particular subgroup that map to the pathway divided by the total number of genes (having probe representation on the microarray platform) assigned to the canonical pathway was calculated. 2) Fischer's exact test was used to calculate a p-value determining the probability that the association between the genes in any particular subgroup and the canonical pathway is explained by chance alone. The negative log of this p-value is the Impact Factor.

NF-κB Transcription Factor TransAM Assay.

NF-κB family activity was measured using the TransAM NF-κB ELISA kit (Active Motif, Carlsbad, Calif.) according to the manufacturer's instructions. Briefly, isolated nuclear pellets were resuspended in extraction buffer (20 mM Hepes pH 7.9, 0.4 M NaCl, 1 mM EDTA). Supernatant (nuclear extract) was retained after a second centrifugation. Samples (10 µg) were added in triplicate to 96-well plates coated with an oligonucleotide that contains a consensus binding sequence for NF-κB components. After 1 h incubation at room temperature, primary antibodies of distinct NF-κB components were added; subsequent addition of HRP-conjugated secondary antibody produced a sensitive colorimetric readout quantified by spectrophotometry at the 450-nm wavelength with a reference wavelength of 655 nm.

Cell Proliferation Assay.

Cell viability was assessed by the 3-(4,5-dimethylthiazol-2-yl)-2,5-diphenyltetrazolium (MTT) assay. Cells were seeded in 24-well plates at 30% confluence and the MTT assay was performed one, two, three and four days after treatment. For each assay, 50 µl of MTT (5 mg/ml) were added to each well and cells were incubated at 37° C. for an additional 4 h. After centrifugation, the supernatant was carefully aspirated and 300 µl of DMSO (Sigma) were added to each well. Immediately after resolubilization, all plates were scanned at 575 nm on a microplate reader. The absorbance (A) value represented the number of live cells.

Chromatin Immunoprecipitation (ChIP) Assay.

ChIP assays were performed by using a CHIP-IT Express Enzymatic kit (Active Motif) according to the manufacturer's protocol. Cells were grown to 80% confluence in DMEM supplemented with 10% FBS and then cross-linked with 1% formaldehyde at room temperature for 10 min. Cells were harvested and digested with trypsin, followed by centrifugation. Supernatants were precleared at 4° C. for 30 min with salmon sperm DNA-protein A-Sepharose and immunoprecipitated with an anti-p65 antibody (Santa Cruz Biotechnology) overnight at 4° C. Immunoprecipitation with normal rabbit IgG was performed to evaluate the presence of non-specific interactions, and aliquots of DNA-protein complexes were analyzed by PCR to normalize for DNA input. Immunocomplexes were incubated with salmon sperm DNA-protein A Sepharose for 1 h at 48° C. Pellets were washed and eluted as per the manufacturer's instructions and then incubated overnight at 65° C. DNA fragments were purified with a QIAquick Spin Kit (Qiagen, Valencia, Calif.). The primers used for the ChIP assays are as follows: ERα forward primer, 5'-AGAAGCTAGACCTCTGCAGG-3' (SEQ ID NO:10), and ERα reverse primer, 5'-AAGCAG GGGCAAG-GAAATATC-3' (SEQ ID NO:11). The amplified 140-bp fragment spans a conserved p65 binding site GGGACTTTCT in the F promoter. For PCR, 2 µl from a 30-µl DNA extraction and 30 cycles of amplification were used.

Statistical Analysis.

The results are presented as mean±standard deviation (SD) of samples measured in triplicate or duplicate. Each experiment was repeated three times, unless otherwise indicated. The Student's t-test was used to calculate differences between the various experimental groups. The difference was considered statistically significant with P<0.05.

Results and Discussion

FOXC1 is Associated with ERα-Negative Human Breast Cancer.

Figure 18:
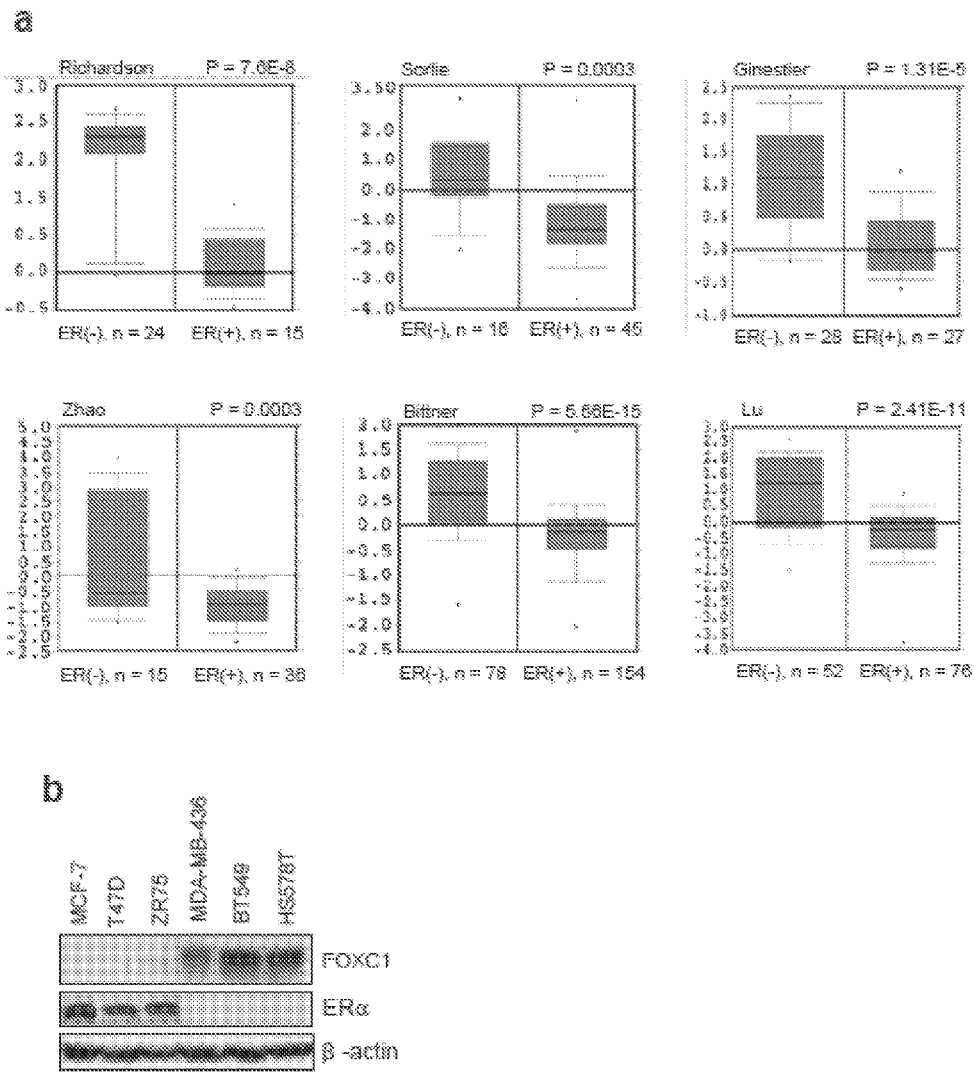
FIG. 18 illustrates that FOXC1 expression is negatively associated with ERα expression in human breast cancer. (A) Microarray data analyses of the association between FOXC1 and ERα expression in human breast cancers. FOXC1 mRNA levels in breast cancer are shown in box plots. The student's t test was conducted using the Oncomine software. Results from six representative data sets [(Ginestier et al., 2006; Lu et al., 2008; Richardson et al., 2006; Sorlie et al., 2001; Zhao et al., 2004) and the Oncology-Breast Samples Project database (Bittnet et al.) of the International Genomics Consortium (IGC) at https://expo.intgen.org/expo/public] are presented. (B) Expression of FOXC1 in ERα-positive or -negative human breast cancer cell lines is shown by immunoblotting.
Figure 19:
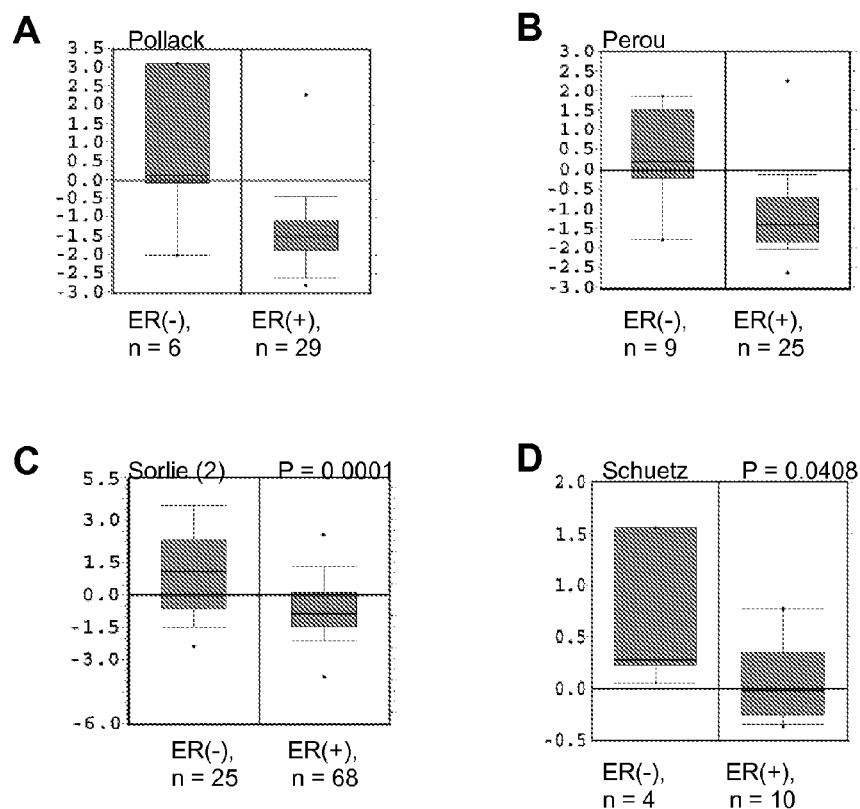
FIG. 19 shows FOXC1 mRNA levels in human breast cancer tissues shown in box plots. Microarray data analyses of the association between FOXC1 and ERα expression in human breast cancers are shown for (A) the Pollock et al. data set; (B) the Perou et al. data set; (C) the Sorlie et al. data set; and (D) the Schuet et al. data set. FOXC1 expression is shown to be negatively associated with ERα expression in breast cancer. The student's t test was conducted using the Oncomine software.

FOXC1 has been identified as a pivotal marker for basal-like breast cancer (Ray et al., 2010), which is characterized by low or absent expression of ER, PR, and HER-2/neu. Analysis of the Oncomine database, which provides publicly available gene expression profiling datasets on human cancers, revealed that FOXC1 mRNA levels inversely correlated with ERα expression in multiple breast cancer cDNA microarray array data sets (Ginestier et al., 2006; Lu et al., 2008; Perou et al., 2000; Pollack et al., 2002; Richardson et al., 2006; Schuetz et al., 2006; Sorlie et al., 2001; Sorlie et al., 2003; Zhao et al., 2004) (FIGS. 18A and 19). Next, FOXC1 levels in well-known ERα-positive or -negative human breast cancer cell lines were examined. Immunoblotting demonstrated that FOXC1 was readily detected in ERα-negative breast cancer cell lines, but not in ERα-positive cells (FIG. 18B).

FOXC1 Downregulates ERα Expression.

Figure 20:
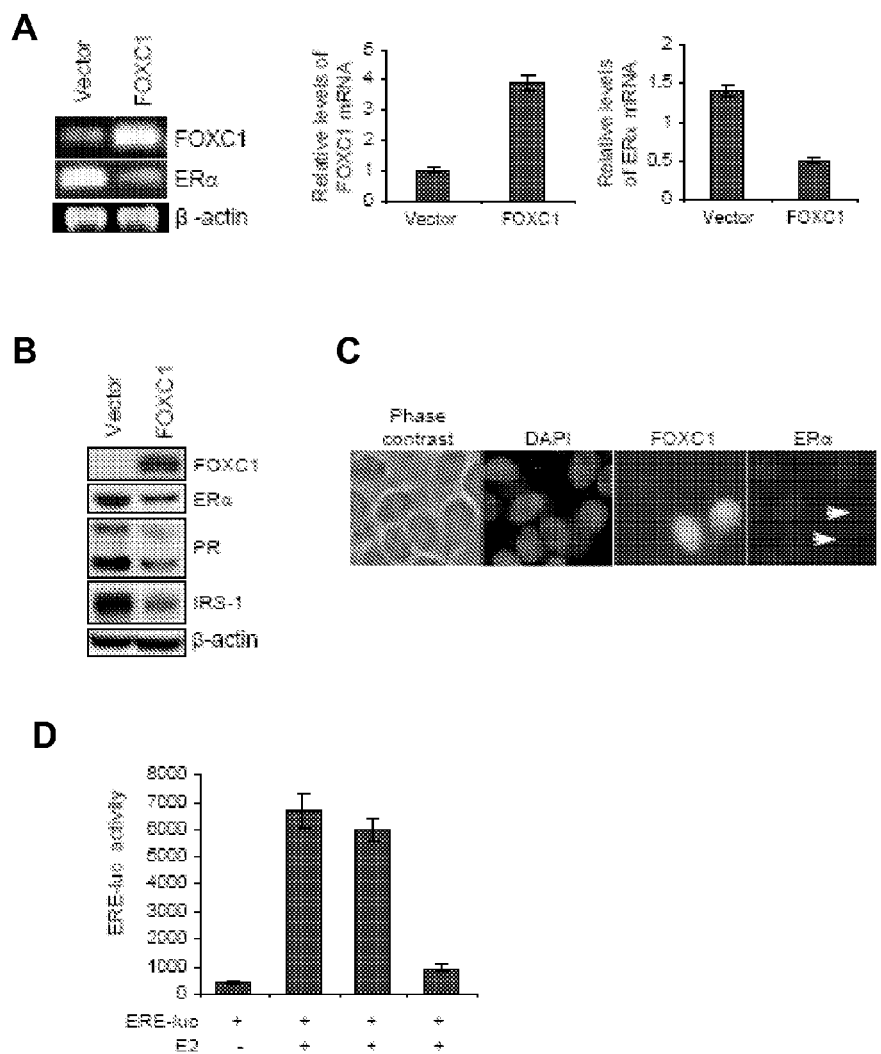
FIG. 20 illustrates that FOXC1 downregulates ERα expression. (A) FOXC1 and ERα mRNA levels in vector or FOXC1 overexpressing MCF-7 cells were measured by RT-PCR (left) and real time RT-PCR (middle and right). (B) Protein levels of FOXC1, ERα, and ERα-regulated genes PR and IRS-1 in vector- or FOXC1-overexpressing MCF-7 cells were measured by immunoblotting. (C) FOXC1 was transiently transfected into MCF-7 cells. Immunofluorescence staining of FOXC1 (green) and ERα (red) was performed. The nuclear DNA (blue) was stained by DAPI. Magnification: ×400. (D) MCF-7 cells were transiently transfected with the ERE-luc reporter construct and the FOXC1 construct or the control vector. Cells were treated with $10^{-8}$ M 17β-estradiol (E2) for 24 h, and were then lysed. Luciferase activity was measured and normalized to β-galactosidase activity. Data represent mean±SD of three independent experiments.
Figure 21:
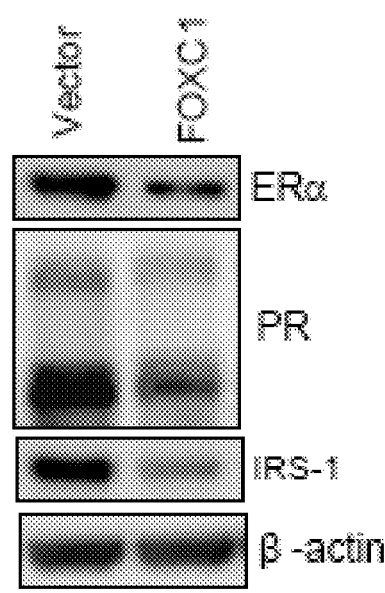
FIG. 21 is an immunoblot illustrating that FOXC1 downregulates ERα expression. FOXC1 was stably transfected into T47D breast cancer cells. Protein levels of FOXC1, ERα, and ERα-regulated genes PR and IRS-1 in vector-or FOXC1-overexpressing T47D cells were measured by immunoblotting.

In light of the strong inverse correlation between FOXC1 and ER levels in breast cancer, it was determined whether FOXC1 affects ERα expression. To address this question, FOXC1 was stably transfected into ERα-positive MCF-7 breast cancer cells. Ectopic overexpression of FOXC1 substantially reduced ERα levels in stable transfectants, as shown by reverse transcription-PCR (RT-PCR) and western blotting (FIGS. 20A and 20B). In accordance, well-established estrogen-regulated genes PR and insulin receptor substrate-1 (IRS-1) were also downregulated in FOXC1-overexpressing MCF-7 cells (FIG. 20B). Similar results were also observed in ERα-positive T47D breast cancer cells (FIG. 21).

To corroborate the above finding, a GFP-FOXC1 fusion gene construct was transiently transfected into MCF-7 cells. Immunofluorescence staining demonstrated that ERα levels were markedly lower in MCF-7 cells expressing GFP-FOXC1 compared with neighboring cells harboring barely detectable GFP signal (FIG. 20C). Next, MCF-7 cells with an estrogen response element (ERE)-luciferase reporter construct were transiently co-transfected as described previously (Cui et al., 2003), and a FOXC1 plasmid, and then stimulated the cells with estradiol. As illustrated in FIG. 20D, FOXC1 suppressed estradiol-induced luciferase activity, suggesting that the transcriptional activity of ERα was inhibited. Taken together, these results indicate that FOXC1 is a repressor of ERα expression and thereby its activity.

FOXC1 Reduces the Sensitivity of Breast Cancer Cells to ERα Ligands.

Figure 22:
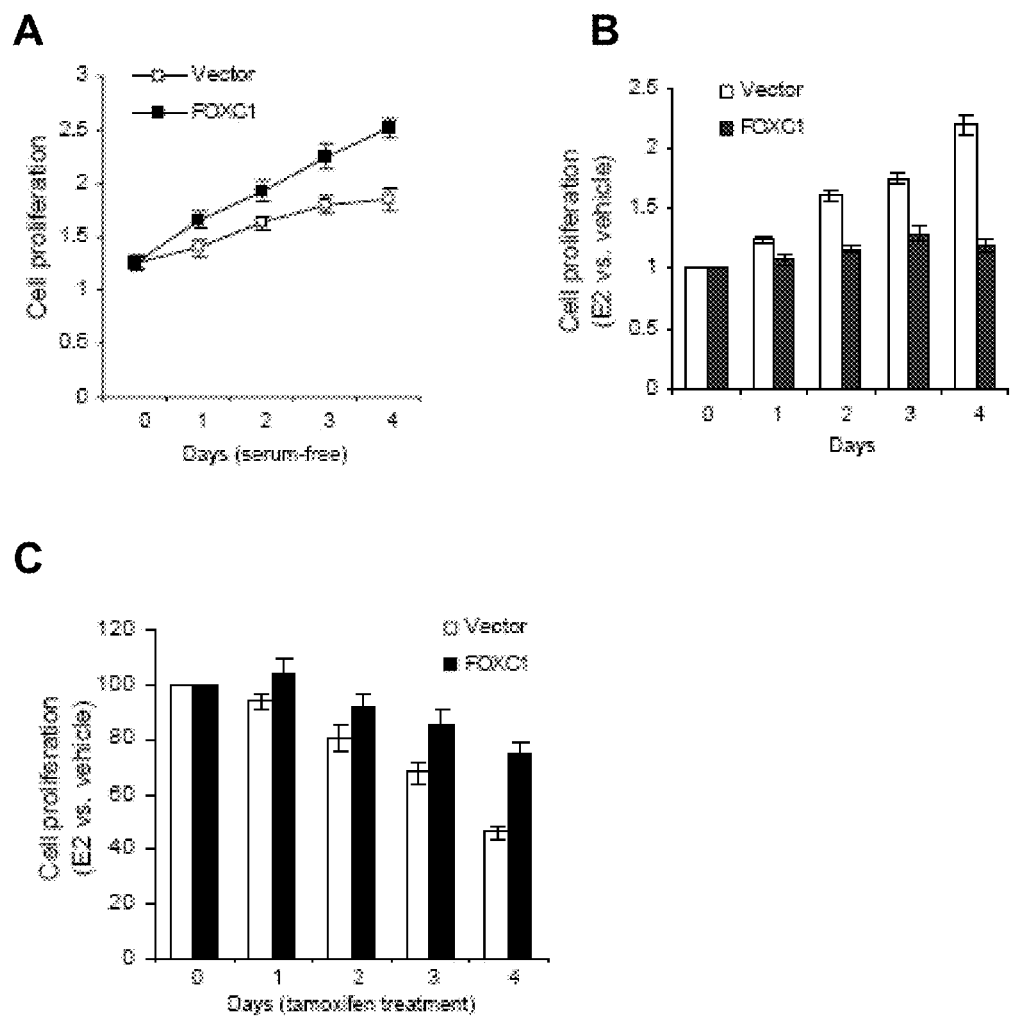
FIG. 22 shows line (A) and bar (B-C) graphs illustrating that FOXC1 reduces the sensitivity to estrogen and antiestrogen in breast cancer cells. (A) Proliferation of FOXC1-overexpressing and control MCF-7 cells in serum-free medium was measured by MTT assays. (B) FOXC1-overexpressing and control MCF-7 cells were serum-starved for 24 h, and then treated with $10^{-8}$ M E2 for the indicated time periods. Cell proliferation was measured by MTT assays and is presented as relative growth rates compared with the vehicle control. (C) FOXC1-overexpressing and control MCF-7 cells in regular medium were treated with $10^{-6}$ M tamoxifen for the indicated time periods. Cell proliferation was measured by MTT assays and is presented as relative growth rates vs. the vehicle control.

Previously, FOXC1 overexpression was shown to enhance cell growth under normal culture conditions (Ray et al., 2010). Thus, it was determined whether FOXC1 affects the growth of MCF-7 cells under other culture conditions. As illustrated in FIGS. 22A and 22B, FOXC1 overexpression potentiated the growth of MCF-7 cells in serum-free medium, but diminished the increase of cell growth induced by estradiol treatment compared with serum-starved conditions. In addition, FOXC1 overexpression rendered MCF-7 cells less sensitive to the treatment of the antiestrogen tamoxifen (FIG. 22C). Collectively, these data suggest that the downregulation of ERα by FOXC1 enables MCF-7 cell growth to be less dependent on E2-induced ERα activation or tamoxifen-induced ERα inactivation.

FOXC1 Upregulates NF-κB Activity.

Figure 23:
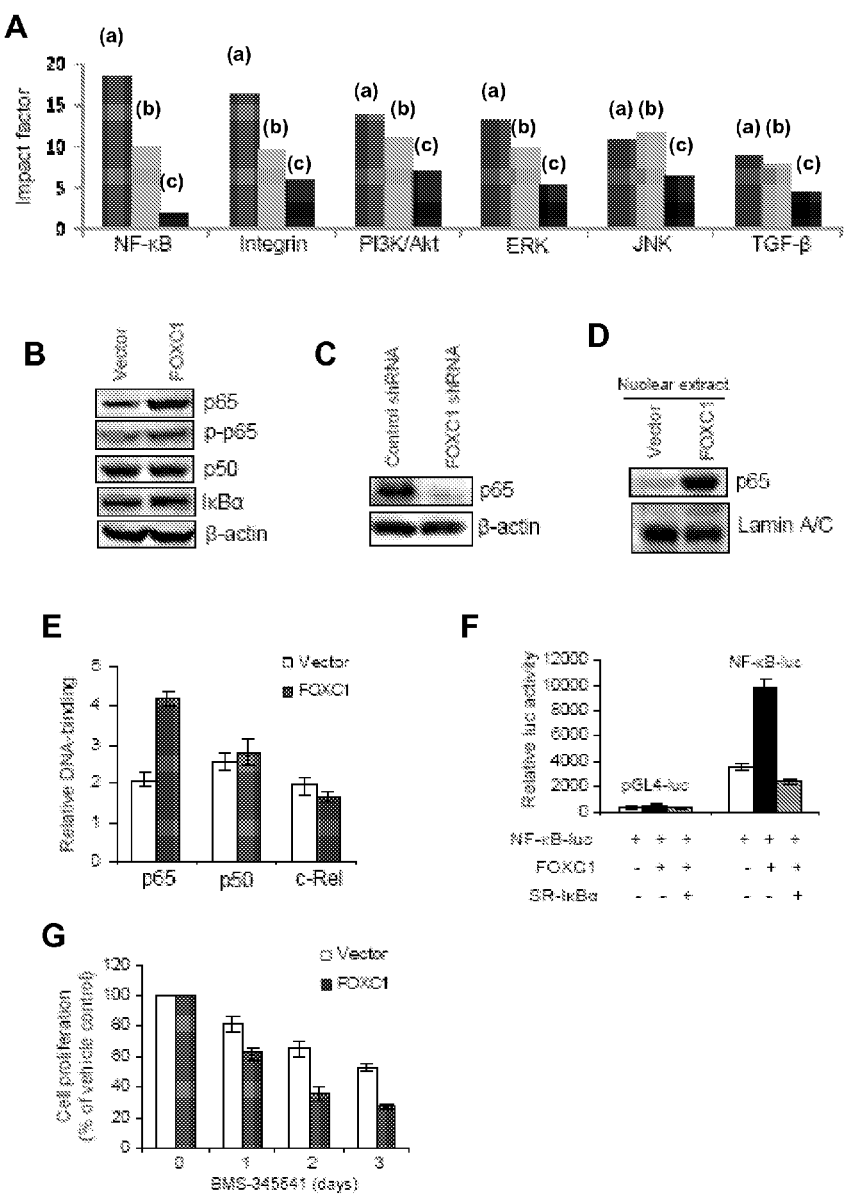
FIG. 23 shows that FOXC1 induces NF-κB activity in breast cancer cells. (A) Most significant canonical signaling pathways identified in the three breast cancer subgroups from the Richardson et al. dataset using Ingenuity Pathway Analysis software is shown (Basal-like-(a), HER2-(b), Luminal-(c)). Genes from the dataset that were associated with a canonical pathway in the Ingenuity Pathways Knowledge Base were considered for the analysis. Fischer's exact test was used to calculate a p-value determining the probability that the association between the genes in a particular subgroup and the canonical pathway is explained by chance alone. Displayed canonical pathways appear in rank order of their Impact Factor, the negative log of the Fischer's exact test p-value. (B) Expression of NF-κB components in MCF-7 cells overexpressing FOXC1 or the vector was examined by immunoblotting. (C) Expression of p65 in 4T1 breast cancer cells stably transduced with control or FOXC1 shRNA was examined by immunoblotting. (D) Nuclear proteins were isolated from MCF-7 cells overexpressing FOXC1 or the control vector, followed by immunoblotting of p65 and the nuclear protein Lamin A/C. (E) Nuclear proteins were isolated from MCF-7 cells overexpressing FOXC1 or the control vector. The binding of p65, p50, and c-Rel to consensus DNA oligonucleotides was assessed by ELISA. Data represent mean±SD of three independent experiments. (F) MCF-7 cells were transiently transfected with NF-κB-luc, FOXC1, and a super-repressor IκBα. NF-κB activity was assessed by luciferase assays. Each bar represents mean±SD of three independent experiments. (G) MCF-7 cells overexpressing FOXC1 or the vector were treated with the IKK inhibitor BMS-345541 (5 μM). Cell proliferation at the indicated time points was measured by MTT assays and is presented as relative growth rates compared with the vehicle control.

Because analysis of the human ERα gene promoter (Kos et al., 2001; Tanimoto et al., 1999) did not find conserved FOXC1-binding sites, it was postulated that the inhibition of ERα by FOXC1 may be mediated by other signaling mechanisms. With this in view, an unbiased screening approach was adopted. As FOXC1 is an important marker for basal-like breast cancer, a systematic signaling network analysis of breast cancer cDNA microarray data sets was conducted using the Ingenuity IPA platform (see Materials and Methods) to identify basal-like breast cancer-associated signaling pathways. As illustrated in FIG. 23A, NF-κB was uncovered as one of the most distinctive pathways in the basal-like subtype, which is consistent with the previous finding that the NF-κB transcription factor is constitutively activated in ER-negative breast cancer and essential for the proliferation of basal-like breast cancer cells (Karin et al., 2002; Nakshatri et al., 1997; Singh et al., 2007).

Given the above finding, it was determined whether FOXC1 regulates NF-κB function. Immunoblotting showed that the p65 subunit and p-p65 (Ser546, an IκB kinase [IKK] phosphorylation site) were markedly induced by FOXC1 overexpression in MCF-7 cells (FIG. 23B). Conversely, knockdown of FOXC1 by its shRNA repressed p65 expression in 4T1 mouse breast cancer cells, which possess high levels of endogenous FOXC1 (FIG. 23C). Previously it was shown that p65 levels are primarily controlled at the protein stability level (Ryo et al., 2003). Using RT-PCR and the protein translation inhibitor cycloheximide, this p65 upregulation by FOXC1 was confirmed to be via an increase in its protein stability (data not shown). Immunoblotting using nuclear extracts indicated that FOXC1 promoted p65 translocation into the nucleus (FIG. 23D). In agreement, TransAM ELISA using oligonucleotides comprising consensus NF-κB-binding sequences showed that FOXC1 considerably increased the DNA-binding activity of p65 (FIG. 23E). To corroborate that FOXC1 enhances NF-κB activity, an NF-κB-responsive luciferase reporter construct was used. As illustrated in FIG. 23F, FOXC1 overexpression significantly increased NF-κB-driven luciferase activity. Co-expression of a super-repressor IκBα, a p65-inhibiting protein, abolished this FOXC1 effect. Interestingly, FOXC1 overexpression sensitized MCF-7 cells to pharmacologic inhibition of NF-κB by its small-molecule inhibitor BMS-345541 in cell proliferation assays (FIG. 23G). Similar results were obtained with other ERα-positive breast cancer cell lines (data not shown). Taken together, these results demonstrate that FOXC1 is a potent inducer of NF-κB activation.

NF-κB Downregulates ERα Expression.

Figure 24:
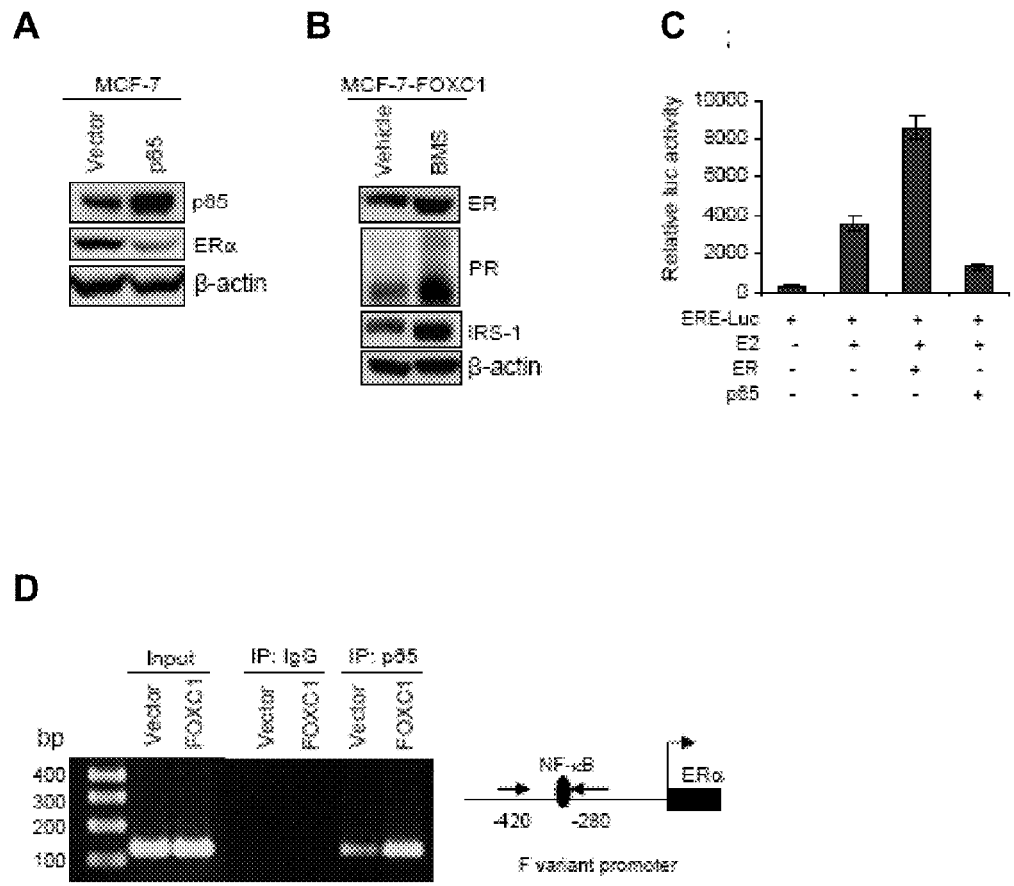
FIG. 24 shows that NF-κB downregulates ERα in breast cancer cells. (A) Expression of p65 and ERα in MCF-7 cells transfected with p65 or the vector for 48 h was examined by immunoblotting. (B) Expression of ERα, PR, and IRS-1 in MCF-7 cells treated with the IKK inhibitor BMS-345541 (5 µM) for 24 h was examined by immunoblotting. (C) MCF-7 cells were transiently transfected with ERE-luc and ERα or p65, and then treated with $10^{-8}$ M E2 for 24 h. ER activity was assessed by luciferase assays. Each bar represents mean±SD of three independent experiments. (D) ChIP assays were performed as described in Materials and Methods. Antibodies against p65 protein were utilized to immunoprecipitate p65-DNA complexes. The input control was 1% of the protein-chromatin supernatant subjected to ChIP assays. The amplified ERα promoter region is −420/−280 (right).
Figure 25:
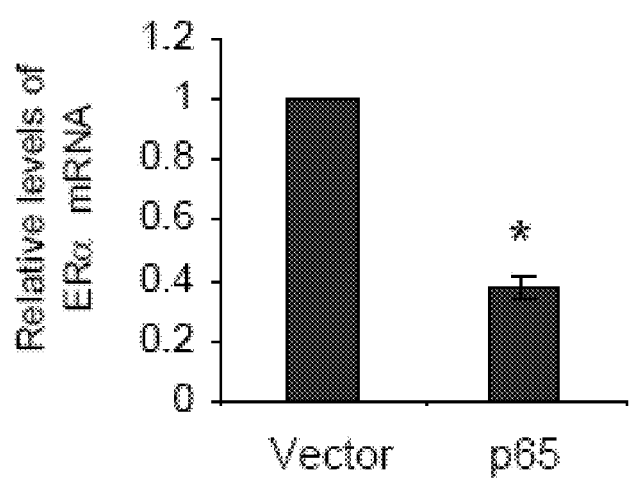
FIG. 25 shows that NF-κB downregulates ERα in breast cancer cells. Expression of ERα in MCF-7 cells transfected with p65 or the vector for 48 h was examined by real-time RT-PCR. Data represent mean±SD of three independent experiments.*, P<0.05 vs the vector control.

NF-κB is associated with ERα negative status in breast cancer (Biswas et al., 2004; Nakshatri et al., 1997). It has been shown that NF-κB negatively regulates ERα expression (Biswas et al., 2005; Holloway et al., 2004). To further investigate whether NF-κB plays a role in the effect of FOXC1 on ERα expression, the NF-κB p65 subunit in MCF-7 cells was overexpressed by transfection. Immunoblotting showed that increased p65 expression lowered ERα protein levels in MCF-7 cells (FIG. 24A). Real-time RT-PCR indicated that ERα mRNA levels were also decreased (FIG. 25). Conversely, inhibition of NF-κB by the IKK inhibitor BMS-345541 in FOXC1-overexpressing MCF-7 cells elevated levels of ERα, PR, and IRS-1 (FIG. 24B). In addition, when p65 or ERα was transiently co-transfected with a ERE luciferase reporter construct, E2-induced luciferase activity was substantially decreased by p65 co-transfection, while increased by ERα co-transfection (FIG. 24C).

The human ERα mRNA is transcribed from at least seven different promoters with unique 5'-untranslated regions (Kos et al., 2001). All these ERα transcripts utilize a same splice accept site at nucleotide +163 from the transcription start site in the originally identified exon 1 (Green et al., 1986). Previous studies showed that p65 binds to the B promoter of the ERα gene (Tanimoto et al., 1999). Notably, there is also a highly conserved p65-binding site GGGACTTTCA at position −430 in the ERα F promoter (Mahmoodzadeh et al., 2009). To confirm that p65 binds to this promoter region, chromatin immunoprecipitation (ChIP) assays were performed using cell extracts prepared from control and FOXC1-overexpressing MCF-7 cells. The 140 bp amplified promoter region spans the binding site. As presented in FIG. 24D, p65 binding to the ERα F promoter was increased by FOXC1 overexpression. Taken together, these results suggest that p65 mediates the FOXC1 suppression of ER expression.

In this study, it was shown that expression of FOXC1, a transcription factor essential for mesoderm tissue development in vertebrates (Berry et al., 2002; Saleem et al., 2003) and a marker for basal-like breast cancer (Ray et al., 2010), inversely correlates with levels of ERα in breast cancer tissues and cell lines. Specifically, it was found that FOXC1 upregulates the NF-κB p65 subunit, which then downregulates ERα expression via a transcriptional mechanism. Upregulation of p65 also desensitizes breast cancer cells to estradiol and the antiestrogen tamoxifen. Essentially, FOXC1 overexpression causes cells to switch from estrogen-dependent to NF-κB-dependent proliferation, a finding confirmed by breast cancer cell sensitivity to NF-κB inhibition. NF-κB is a well-established transcription factor that plays a central role in regulating the expression of many genes associated with cell proliferation, immune response, inflammation, cell survival, and oncogenesis (Karin et al., 2002; Lin et al.). This study provides evidence for NF-κB-mediated crosstalk between ERα and FOXC1.

Previous studies have revealed that forkhead box A1 (FOXA1) and GATA binding protein 3 (GATA-3) are expressed in close association with ERα (Albergaria et al., 2009). Both are transcription factors implicated in ERα-mediated action in breast cancer (Eeckhoute et al., 2007; Lupien et al., 2008; van der Heul-Nieuwenhuijsen et al., 2009). FOXA1 binds to chromatin DNA and opens the chromatin structure, thereby enhancing the binding of ERα to the promoters of its target genes. The binding site of FOXA1 is usually in close proximity to ERα binding sites. In this regard, FOXA1 acts as a priming factor in the recruitment of ERα to its cis-regulatory elements in the genome and subsequent transcriptional induction of target genes such as cyclin D1 in breast cancer cells (Carroll et al., 2005; Laganiere et al., 2005). GATA-3 is required for estrogen stimulation of cell cycle progression in breast cancer cells. It upregulates ERα by binding to two cis-regulatory elements located within the ERα gene; this binding allows recruitment of RNA polymerase II to ERα promoters (Eeckhoute et al., 2007). Another forkhead box transcription factor FOXO3a also induces ERα expression via binding to the ERα promoter (Belguise and Sonenshein, 2007; Guo and Sonenshein, 2004).

In addition to its association with ERα-negative breast cancer in general, NF-κB activation has been linked to EGFR or HER-2 overexpression-induced loss of ER in inflammatory breast cancer (Van Laere et al., 2007). This is consistent with an earlier finding that NF-κB mediates the downregulation of ER by hyperactive MAPK (Holloway et al., 2004; Oh et al., 2001), commonly induced by EGFR and HER-2 overexpression. It should be noted that mechanisms for the inhibition of ERα by NF-κB are still not well understood. NF-κB p65 may act by directly binding to the ERα promoter (Mahmoodzadeh et al., 2009; Tanimoto et al., 1999). In addition to the reported NF-κB binding sites in the B promoter of the ERα gene (Tanimoto et al., 1999), there is a highly conserved NF-κB binding site in the F promoter of ERα at nucleotides −380 to −420 (Mahmoodzadeh et al., 2009). CHIP analysis confirmed that NF-κB can bind to the region containing the conserved sequences. Another possibility is that p65 interacts with ERα and thereby inhibits ERα activity (Gionet et al., 2009; Stein and Yang, 1995). This may in turn reduce ERα transcription, which can be positively regulated by estrogen-activated ERα itself through half EREs in its promoter (Piva et al., 1988; Treilleux et al., 1997). The NF-κB effect may also be explained in part by its regulation of genes that modulate ERα expression.

In summary, this study delineates a mechanism for the low or absent ERα expression in basal-like breast cancer and proposes a new paradigm for investigating the control of ERα expression during breast cancer progression. These findings build on a previous report that expression of cyclin D1 and other growth-promoting genes is increased in FOXC1-over-expressing cells. A link between ERα and FOXC1/NF-κB may have clinical implications for ERα-positive breast cancer patients who recur with ERα-negative cancer.

Example 6

Prognostic Stratification of HER2-Enriched Patients Utilizing Semi-Quantitative Gene Expression Microarray Assessment of FOXC1

Human epidermal growth factor receptor 2 (HER2) enriched tumors display either gene amplification or protein overexpression. This subtype of breast cancer is notable for its variable prognosis and response to systemic therapy. It has been suggested that a subset of HER2-positive tumors exhibit basal-like characteristics, the so-called basal-HER2 subtype. The basal-HER2 subtype has been shown to have the worst prognosis within HER2-overexpressing tumors. It has been suggested that the basal-HER2 subtype simultaneously co-expresses HER2 and markers typical of basal-like breast cancer. As described in the examples above, FOXC1 is a theranostic biomarker of the basal-like breast cancer molecular subtype. Therefore, FOXC1 expression may be investigated within HER2-overexpressing tumors to determine whether FOXC1 expression represents the basal-HER2 subtype and prognosticates poor overall survival (OS).

Gene expression microarray data from 58 HER2-amplified tumors were obtained from a publicly available database that contained linked clinical outcomes data (J Clin Oncol. 2010 Apr. 10; 28(11):1813-20. Epub 2010 March 15). The data was analyzed for FOXC1 expression and a median cutoff value (50th percentile) was used to segregate tumors into FOXC1 high and FOXC1 low designations. Prognostic significance of FOXC1 (high vs. low) was assessed using univariate and multivariate analyses.

Figure 14:
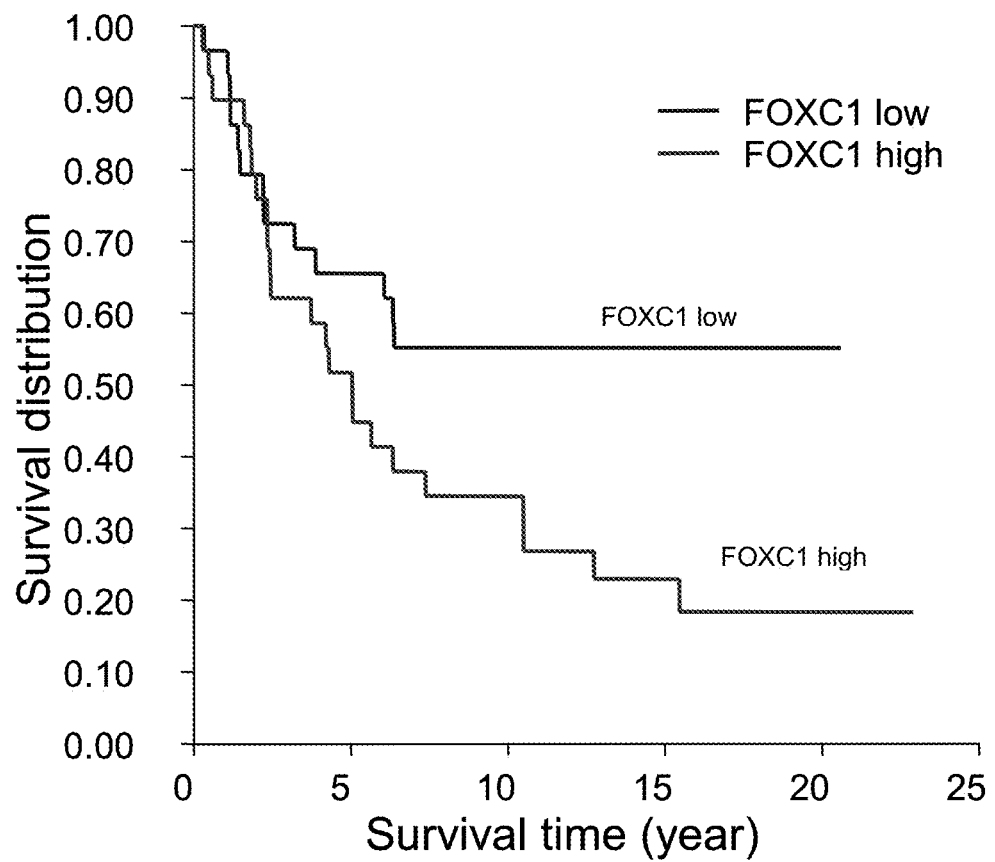
FIG. 14 is a Kaplan-Meier curve of overall survival using microarray data from 58 HER2-amplified tumors. Semiquantitative FOXC1 mRNA expression above the 50$^{th}$ percentile was found to be a significant predictor of poor survival (p=0.0313 on univariate analysis). On multivariate analysis, when controlled for age, tumor size and nodal status, FOXC1 mRNA expression greater than 50$^{th}$ percentile cutoff value was an independent prognosticator of poor survival (HR 2.54, 95% CI 1.21-5.33, p=0.0138). Nodal status and age were not significant prognosticators on multivariate analysis (Staaf et al. 2010).

FIG. 14 shows that the FOXC1 high designation had a significantly worse OS compared to the FOXC1 low designation (p=0.0313). FOXC1 high designation was an independent prognostic indicator for worse OS when controlled for age, tumor size, and lymph node status (HR 2.54, 95% CI 1.21-5.33, p=0.0138).

Tumors that co-express FOXC1 and HER2 may represent the hybrid basal-like/HER2+ subtype. Patients with HER2-enriched tumors that have an elevated FOXC1 expression display worse survival. Assessment of FOXC1 expression within HER2-enriched tumors may represent a pragmatic approach for the diagnosis and prognosis of the basal-HER2 subtype.

Example 7

Prognostic Stratification of Luminal Patients Utilizing Semi-Quantitative Gene Expression Microarray Assessment of FOXC1

Estrogen receptor and/or progesterone receptor-enriched tumors display either gene amplification or protein overexpression of ER and/or PR. A subset of ER-positive and/or PR positive tumors may exhibit basal-like characteristics, the so-called hybrid basal-like/luminal subtype. The hybrid basal-like/luminal subtype likely has the worst prognosis within ER or PR overexpressing tumors. The hybrid basal-like/luminal subtype likely simultaneously co-expresses ER and/or PR and markers typical of basal-like breast cancer. As described in the examples above, FOXC1 is a theranostic biomarker of the basal-like breast cancer molecular subtype. Therefore, FOXC1 expression may be investigated within ER and/or PR overexpressing tumors to determine whether FOXC1 expression represents the hybrid basal-like/luminal subtype and prognosticates poor overall survival (OS).

Gene expression microarray data from ER and/or PR amplified tumors may be obtained from a publicly available database that contains linked clinical outcomes data. The data may be analyzed for FOXC1 expression and a median cutoff value should be used to segregate tumors into FOXC1 high and FOXC1 low designations. Prognostic significance of FOXC1 (high vs. low) may be assessed using univariate and multivariate analyses.

FOXC1 high designation likely has a significantly worse OS compared to the FOXC1 low designation within the luminal subtype. FOXC1 high designation is likely an independent prognostic indicator for worse OS when controlled for age, tumor size, and lymph node status.

Tumors that co-express FOXC1 and ER and/or PR may represent the hybrid basal-like/luminal subtype. Patients with ER and/or PR enriched tumors that have an elevated FOXC1 expression are likely to display worse survival. Assessment of FOXC1 expression within ER and/or PR enriched tumors may represent a pragmatic approach for the diagnosis and prognosis of the hybrid basal-like/luminal subtype.

Example 8

Prognostic Stratification of Triple Negative Patients Utilizing Semi-Quantitative Gene Expression Microarray Assessment of FOXC1

Triple negative tumors do not express ER, PR or HER2. A subset of triple-negative tumors may exhibit basal-like characteristics, the so-called hybrid basal-like/triple negative subtype. The hybrid basal-like/triple negative subtype is associated with the worst prognosis within triple negative tumors. The hybrid basal-like/triple negative subtype likely expresses markers typical of basal-like breast cancer. As described in the examples above, FOXC1 is a theranostic biomarker of the basal-like breast cancer molecular subtype. Therefore, FOXC1 expression may be investigated within triple negative tumors to determine whether FOXC1 expression represents the hybrid basal-like/triple negative subtype and prognosticates poor overall survival (OS).

Gene expression microarray data from triple negative tumors may be obtained from a publicly available database that contains linked clinical outcomes data. The data may be analyzed for FOXC1 expression and a median cutoff value should be used to segregate tumors into FOXC1 high and FOXC1 low designations. Prognostic significance of FOXC1 (high vs. low) may be assessed using univariate and multivariate analyses.

FOXC1 high designation likely has a significantly worse OS compared to the FOXC1 low designation within the triple negative subtype. FOXC1 high designation is likely an independent prognostic indicator for worse OS when controlled for age, tumor size, and lymph node status.

Tumors that express FOXC1 and not ER, PR and HER2 may represent the hybrid basal-like/triple negative subtype. Patients with triple negative tumors that have an elevated FOXC1 expression are likely to display worse survival. Assessment of FOXC1 expression within triple negative tumors may represent a pragmatic approach for the diagnosis and prognosis of the hybrid basal-like/luminal subtype.

REFERENCES

The references listed below, and all references cited in the specification are hereby incorporated by reference in their entirety.

Akaike H. A new look at the statistical model identification. IEEE Trans Automatic Control 1974; 19:716-23.

Akaogi K, Nakajima Y, Ito I, Kawasaki S, Oie S H, Murayama A et al (2009). KLF4 suppresses estrogen-dependent breast cancer growth by inhibiting the transcriptional activity of ERalpha. *Oncogene* 28: 2894-902.

Albergaria A, Paredes J, Sousa B, Milanezi F, Carneiro V, Bastos J et al (2009). Expression of FOXA1 and GATA-3 in breast cancer: the prognostic significance in hormone receptor-negative tumours. *Breast Cancer Res* 11: R40.

Andre F, Job B, Dessen P, et al. Molecular characterization of breast cancer with high-resolution oligonucleotide comparative genomic hybridization array. Clin Cancer Res 2009; 15:441-51.

Aslakson C J, Miller F R. Selective events in the metastatic process defined by analysis of the sequential dissemination of subpopulations of a mouse mammary tumor. Cancer Res 1992; 52:1399-405.

Belguise K, Sonenshein G E (2007). PKCtheta promotes c-Rel-driven mammary tumorigenesis in mice and humans by repressing estrogen receptor alpha synthesis. *J Clin Invest* 117: 4009-21.

Berry F B, Saleem R A, Walter M A (2002). FOXC1 transcriptional regulation is mediated by N- and C-terminal activation domains and contains a phosphorylated transcriptional inhibitory domain. *J Biol Chem* 277: 10292-7.

Berry F B, Mirzayans F, Walter M A. Regulation of FOXC1 stability and transcriptional activity by an epidermal growth factor-activated mitogen-activated protein kinase signaling cascade. J Biol Chem 2006; 281:10098-104.

Biswas D K, Shi Q, Baily S, Strickland I, Ghosh S, Pardee A B et al (2004). NF-kappa B activation in human breast cancer specimens and its role in cell proliferation and apoptosis. *Proc Natl Acad Sci USA* 101: 10137-42.

Biswas D K, Singh S, Shi Q, Pardee A B, Iglehart J D (2005). Crossroads of estrogen receptor and NF-kappaB signaling. *Sci STKE* 2005: pe27.

Bloushtain-Qimron N, Yao J, Snyder E L, et al. Cell type-specific DNA methylation patterns in the human breast. Proc Natl Acad Sci USA 2008; 105:14076-81.

Carey L A, Perou C M, Livasy C A, et al. Race, breast cancer subtypes, and survival in the Carolina Breast Cancer Study. JAMA 2006; 295:2492-502.

Carroll J S, Liu X S, Brodsky A S, Li W, Meyer C A, Szary A J et al (2005). Chromosome-wide mapping of estrogen receptor binding reveals long-range regulation requiring the forkhead protein FoxA1. *Cell* 122: 33-43.

Charafe-Jauffret E, Monville F, Bertucci F, et al. Moesin expression is a marker of basal breast carcinomas. Int J Cancer 2007; 121: 1779-85.

Cheang M C, Voduc D, Bajdik C, Leung S, McKinney S, Chia S K, et al. Basal-like breast cancer defined by five biomarkers has superior prognostic value than triple-negative phenotype. Clin Cancer Res. 2008 Mar. 1; 14(5):1368-76.

Couse J F, Korach K S (1999). Estrogen receptor null mice: what have we learned and where will they lead us? *Endocr Rev* 20: 358-417.

Cui X, Zhang P, Deng W, Oesterreich S, Lu Y, Mills G B et al (2003). Insulin-like growth factor-I inhibits progesterone receptor expression in breast cancer cells via the phosphatidylinositol 3-kinase/Akt/mammalian target of rapamycin pathway: progesterone receptor as a potential indicator of growth factor activity in breast cancer. *Mol Endocrinol* 17: 575-88.

Cox D R H D. Theoretical Statistics. New York, N.Y., Chapman and Hall, 1974.1974.

deConinck E C, McPherson L A, Weigel R J (1995). Transcriptional regulation of estrogen receptor in breast carcinomas. *Mol Cell Biol* 15: 2191-6.

Dent R, Trudeau M, Pritchard K I, et al. Triple-negative breast cancer: clinical features and patterns of recurrence. Clin Cancer Res 2007; 13:4429-34.

Dhasarathy A, Kajita M, Wade P A (2007). The transcription factor snail mediates epithelial to mesenchymal transitions by repression of estrogen receptor-alpha. *Mol Endocrinol* 21: 2907-18.

Eeckhoute J, Keeton E K, Lupien M, Krum S A, Carroll J S, Brown M (2007). Positive cross-regulatory loop ties GATA-3 to estrogen receptor alpha expression in breast cancer. *Cancer Res* 67: 6477-83.

Elsheikh S E, Green A R, Rakha E A, et al. Caveolin 1 and caveolin 2 are associated with breast cancer basal-like and triple-negative immunophenotype. Br J Cancer 2008; 99:327-34.

Farmer P, Bonnefoi H, Becette V, et al. Identification of molecular apocrine breast tumours by microarray analysis. Oncogene 2005; 24:4660-71.

Fuqua S A, Schiff R, Parra I, Moore J T, Mohsin S K, Osborne C K et al (2003). Estrogen receptor beta protein in human breast cancer: correlation with clinical tumor parameters. *Cancer Res* 63: 2434-9.

Ginestier C, Cervera N, Finetti P, Esteyries S, Esterni B, Adelaide J et al (2006). Prognosis and gene expression profiling of 20q13-amplified breast cancers. *Clin Cancer Res* 12: 4533-44.

Gionet N, Jansson D, Mader S, Pratt M A (2009). NF-kappaB and estrogen receptor alpha interactions: Differential function in estrogen receptor-negative and -positive hormone-independent breast cancer cells. *J Cell Biochem* 107: 448-59.

Green S, Walter P, Kumar V, Krust A, Bornert J M, Argos P et al (1986). Human oestrogen receptor cDNA: sequence, expression and homology to v-erb-A. *Nature* 320: 134-9.

Guo S, Sonenshein G E (2004). Forkhead box transcription factor FOXO3a regulates estrogen receptor alpha expression and is repressed by the Her-2/neu/phosphatidylinositol 3-kinase/Akt signaling pathway. *Mol Cell Biol* 24: 8681-90.

Hasegawa M, Moritani S, Murakumo Y, et al. CD109 expression in basal-like breast carcinoma. Pathol Int 2008; 58: 288-94.

Herschkowitz J I, Simin K, Weigman V J, et al. Identification of conserved gene expression features between murine mammary carcinoma models and human breast tumors. Genome Biol 2007; 8:R76.

Hess K R, Anderson K, Symmans W F, et al. Pharmacogenomic predictor of sensitivity to preoperative chemotherapy with paclitaxel and fluorouracil, doxorubicin, and cyclophosphamide in breast cancer. J Clin Oncol 2006; 24:4236-44.

Holloway J N, Murthy S, El-Ashry D (2004). A cytoplasmic substrate of mitogen-activated protein kinase is responsible for estrogen receptor-alpha down-regulation in breast cancer cells: the role of nuclear factor-kappaB. Mol Endocrinol 18: 1396-410.

Nosey A M, Gorski J J, Murray M M, Quinn J E, Chung W Y, Stewart G E et al (2007). Molecular basis for estrogen receptor alpha deficiency in BRCA1-linked breast cancer. J Natl Cancer Inst 99: 1683-94.

Hu Z, Fan C, Oh D S, et al. The molecular portraits of breast tumors are conserved across microarray platforms. BMC Genomics 2006; 7:96.

Ihemelandu C U, Leffall L D, Jr., Dewitty R L, Naab T J, Mezghebe H M, Makambi K H, et al. Molecular breast cancer subtypes in premenopausal and postmenopausal African-American women: age-specific prevalence and survival. J Surg Res. 2007 November; 143(1):109-18.

Ihemelandu C U, Naab T J, Mezghebe H M, Makambi K H, Siram S M, Leffall L D, Jr., et al. Treatment and survival outcome for molecular breast cancer subtypes in black women. Ann Surg. 2008 March; 247(3):463-9.

Ivshina A V, George J, Senko O, et al. Genetic reclassification of histologic grade delineates new clinical subtypes of breast cancer. Cancer Res 2006; 66:10292-301.

Karin M, Cao Y, Greten F R, Li Z W (2002). NF-kappaB in cancer: from innocent bystander to major culprit. Nat Rev Cancer 2: 301-10.

Keen J C, Davidson N E (2003). The biology of breast carcinoma. Cancer 97: 825-33.

Korsching E, Jeffrey S S, Meinerz W, Decker T, Boecker W, Buerger H. Basal carcinoma of the breast revisited: an old entity with new interpretations. J Clin Pathol 2008; 61: 553-60.

Kos M, Reid G, Denger S, Gannon F (2001). Minireview: genomic organization of the human ERalpha gene promoter region. Mol Endocrinol 15: 2057-63.

Kreike B, van Kouwenhove M, Horlings H, et al. Gene expression profiling and histopathological characterization of triple-negative/basal-like breast carcinomas. Breast Cancer Res 2007; 9:R65.

Kuiper G G, Carlsson B, Grandien K, Enmark E, Haggblad J, Nilsson S et al (1997). Comparison of the ligand binding specificity and transcript tissue distribution of estrogen receptors alpha and beta. Endocrinology 138: 863-70.

Laganiere J, Deblois G, Lefebvre C, Bataille A R, Robert F, Giguere V (2005). From the Cover: Location analysis of estrogen receptor alpha target promoters reveals that FOXA1 defines a domain of the estrogen response. Proc Natl Acad Sci USA 102: 11651-6.

Landis S H, Murray T, Bolden S, Wingo P A (1999). Cancer statistics, 1999. CA Cancer J Clin 49: 8-31, 1.

Lin Y, Bai L, Chen W, Xu S The NF-kappaB activation pathways, emerging molecular targets for cancer prevention and therapy. Expert Opin Ther Targets 14: 45-55.

Lin Z, Yin P, Reierstad S, O'Halloran M, Coon V J, Pearson E K et al Adenosine A1 receptor, a target and regulator of estrogen receptoralpha action, mediates the proliferative effects of estradiol in breast cancer. Oncogene 29: 1114-22.

Livasy C A, Karaca G, Nanda R, et al. Phenotypic evaluation of the basal-like subtype of invasive breast carcinoma. Mod Pathol 2006; 19:264-71.

Lu S, Simin K, Khan A, Mercurio A M. Analysis of integrin beta4 expression in human breast cancer: association with basal-like tumors and prognostic significance. Clin Cancer Res 2008; 14: 1050-8.

Lu X, Wang Z C, Iglehart J D, Zhang X, Richardson A L (2008). Predicting features of breast cancer with gene expression patterns. Breast Cancer Res Treat 108: 191-201.

Lupien M, Eeckhoute J, Meyer C A, Wang Q, Zhang Y, Li W et al (2008). FoxA1 translates epigenetic signatures into enhancer-driven lineage-specific transcription. Cell 132: 958-70.

Mahmoodzadeh S, Fritschka S, Dworatzek E, Pham T H, Becher E, Kuehne A et al (2009). Nuclear factor-kappaB regulates estrogen receptor-alpha transcription in the human heart. J Biol Chem 284: 24705-14.

Mani S A, Yang J, Brooks M, et al. Mesenchyme Forkhead 1 (FOXC2) plays a key role in metastasis and is associated with aggressive basal-like breast cancers. Proc Natl Acad Sci USA 2007; 104: 10069-74.

McShane L M, Altman D G, Sauerbrei W, Taube S E, Gion M, Clark G M. REporting recommendations for tumour MARKer prognostic studies (REMARK). Br J. Cancer. 2005 Aug. 22; 93(4):387-91.

Miller L D, Smeds J, George J, et al. An expression signature for p53 status in human breast cancer predicts mutation status, transcriptional effects, and patient survival. Proc Natl Acad Sci USA 2005; 102:13550-5.

Moyano J V, Evans J R, Chen F, et al. AlphaB-crystallin is a novel oncoprotein that predicts poor clinical outcome in breast cancer. J Clin Invest 2006; 116: 261-70.

Nakshatri H, Bhat-Nakshatri P, Martin D A, Goulet R J, Jr., Sledge G W, Jr. (1997). Constitutive activation of NF-kappaB during progression of breast cancer to hormone-independent growth. Mol Cell Biol 17: 3629-39.

Nielsen T O, Hsu F D, Jensen K, et al. Immunohistochemical and clinical characterization of the basal-like subtype of invasive breast carcinoma. Clin Cancer Res 2004; 10:5367-74.

Nishimura D Y, Swiderski R E, Alward W L, Searby C C, Patil S R, Bennet S R et al (1998). The forkhead transcription factor gene FKHL7 is responsible for glaucoma phenotypes which map to 6p25. Nat Genet. 19: 140-7.

Oh A S, Lorant L A, Holloway J N, Miller D L, Kern F G, El-Ashry D (2001). Hyperactivation of MAPK induces loss of ERalpha expression in breast cancer cells. Mol Endocrinol 15: 1344-59.

Osborne C K (1998). Steroid hormone receptors in breast cancer management. Breast Cancer Res Treat 51: 227-38.

Park W C, Jordan V C (2002). Selective estrogen receptor modulators (SERMS) and their roles in breast cancer prevention. Trends Mol Med 8: 82-8.

Parker J S, Mullins M, Cheang M C, et al. Supervised risk predictor of breast cancer based on intrinsic subtypes. J Clin Oncol 2009; 27: 1160-7.

Pawitan Y, Bjohle J, Amler L, et al. Gene expression profiling spares early breast cancer patients from adjuvant therapy: derived and validated in two population-based cohorts. Breast Cancer Res 2005; 7: R953-64.

Perou C M, Sorlie T, Eisen M B, et al. Molecular portraits of human breast tumours. Nature 2000; 406:747-52.

Piva R, Bianchini E, Kumar V L, Chambon P, del Senno L (1988). Estrogen induced increase of estrogen receptor RNA in human breast cancer cells. *Biochem Biophys Res Commun* 155: 943-9.

Pollack J R, Sorlie T, Perou C M, Rees C A, Jeffrey S S, Lonning P E et al (2002). Microarray analysis reveals a major direct role of DNA copy number alteration in the transcriptional program of human breast tumors. *Proc Natl Acad Sci USA* 99: 12963-8.

Qu Y, Wang J, Sim M S, Liu B, Giuliano A, Barsoum J et al (2009). Elesclomol, counteracted by Akt survival signaling, enhances the apoptotic effect of chemotherapy drugs in breast cancer cells. *Breast Cancer Res Treat*.

Ray P, Wang J, Qu Y, Sim M, Shamonki J, Bagaria S P et al (2010). FOXC1 Is a Potential Prognostic Biomarker with Functional Significance in Basal-like Breast Cancer. *Cancer Research May* 15.

Rakha E A, Elsheikh S E, Aleskandarany M A, Habashi H O, Green A R, Powe D G, et al. Triple-negative breast cancer: distinguishing between basal and nonbasal subtypes. Clin Cancer Res. 2009 Apr. 1; 15(7):2302-10.

Richardson A L, Wang Z C, De Nicolo A, et al. X chromosomal abnormalities in basal-like human breast cancer. Cancer Cell 2006; 9:121-32.

Rosen E M, Fan S, Isaacs C (2005). BRCA1 in hormonal carcinogenesis: basic and clinical research. *Endocr Relat Cancer* 12: 533-48.

Ryo A, Suizu F, Yoshida Y, Perrem K, Liou Y C, Wulf G et al (2003). Regulation of NF-kappaB signaling by Pin1-dependent prolyl isomerization and ubiquitin-mediated proteolysis of p65/RelA. *Mol Cell* 12: 1413-26.

Saceda M, Grunt T W, Colomer R, Lippman M E, Lupu R, Martin M B (1996). Regulation of estrogen receptor concentration and activity by an erbB/HER ligand in breast carcinoma cell lines. *Endocrinology* 137: 4322-30.

Saleem R A, Banerjee-Basu S, Berry F B, Baxevanis A D, Walter M A (2003). Structural and functional analyses of disease-causing missense mutations in the forkhead domain of FOXC1. *Hum Mol Genet.* 12: 2993-3005.

Sarrio D, Rodriguez-Pinilla S M, Hardisson D, Cano A, Moreno-Bueno G, Palacios J. Epithelial-mesenchymal transition in breast cancer relates to the basal-like phenotype. Cancer Res 2008; 68:989-97.

Schuetz C S, Bonin M, Clare S E, Nieselt K, Sotlar K, Walter M et al (2006). Progression-specific genes identified by expression profiling of matched ductal carcinomas in situ and invasive breast tumors, combining laser capture microdissection and oligonucleotide microarray analysis. *Cancer Res* 66: 5278-86.

Seewaldt V L, Scott V. Images in clinical medicine. Rapid progression of basal-type breast cancer. N Engl J Med 2007; 356:e12.

Shirley S H, Rundhaug J E, Tian J, Cullinan-Ammann N, Lambertz I, Conti C J et al (2009). Transcriptional regulation of estrogen receptor-alpha by p53 in human breast cancer cells. *Cancer Res* 69: 3405-14.

Singh S, Shi Q, Bailey S T, Palczewski M J, Pardee A B, Iglehart J D et al (2007). Nuclear factor-kappaB activation: a molecular therapeutic target for estrogen receptor-negative and epidermal growth factor receptor family receptor-positive human breast cancer. *Mol Cancer Ther* 6: 1973-82.

Sorlie T, Perou C M, Tibshirani R, Aas T, Geisler S, Johnsen H et al (2001). Gene expression patterns of breast carcinomas distinguish tumor subclasses with clinical implications. *Proc Natl Acad Sci USA* 98: 10869-74.

Sorlie T, Tibshirani R, Parker J, et al. Repeated observation of breast tumor subtypes in independent gene expression data sets. *Proc Natl Acad Sci USA* 2003; 100:8418-23.

Staaf J, Ringnér M, Vallon-Christersson J, Jönsson G, Bendahl P O, Holm K, Arason A, Gunnarsson H, Hegardt C, Agnarsson B A, Luts L, Grabau D, Fernö M, Malmström P O, Johannsson O T, Loman N, Barkardottir R B, Borg A. Identification of subtypes in human epidermal growth factor receptor 2-positive breast cancer reveals a gene signature prognostic of outcome. J Clin Oncol. 2010 Apr. 10; 28(11):1813-20.

Stein B, Yang M X (1995). Repression of the interleukin-6 promoter by estrogen receptor is mediated by NF-kappa B and C/EBP beta. *Mol Cell Biol* 15: 4971-9.

Tanimoto K, Eguchi H, Yoshida T, Hajiro-Nakanishi K, Hayashi S (1999). Regulation of estrogen receptor alpha gene mediated by promoter B responsible for its enhanced expressionin human breast cancer. *Nucleic Acids Res* 27: 903-9.

Treilleux, Peloux N, Brown M, Sergeant A (1997). Human estrogen receptor (ER) gene promoter-P1: estradiol-independent activity and estradiol inducibility in ER+ and ER− cells. *Mol Endocrinol* 11: 1319-31.

van der Heul-Nieuwenhuijsen L, Dits N F, Jenster G (2009). Gene expression of forkhead transcription factors in the normal and diseased human prostate. *BJU Int* 103: 1574-80.

van de Vijver M J, He Y D, van't Veer L J, et al. A gene-expression signature as a predictor of survival in breast cancer. N Engl J Med 2002; 347:1999-2009.

Van Laere S J, Van der Auwera I, Van den Eynden G G, van Dam P, Van Marck E A, Vermeulen P B et al (2007). NF-kappaB activation in inflammatory breast cancer is associated with oestrogen receptor downregulation, secondary to EGFR and/or ErbB2 overexpression and MAPK hyperactivation. *Br J Cancer* 97: 659-69.

Wang Y, Klijn J G, Zhang Y, et al. Gene-expression profiles to predict distant metastasis of lymph-node-negative primary breast cancer. Lancet 2005; 365:671-9.

Yaziji H, Goldstein L C, Barry T S, Werling R, Hwang H, Ellis G K, et al. HER-2 testing in breast cancer using parallel tissue-based methods. JAMA. 2004 Apr. 28; 291(16):1972-7. Bland J M, Altman D G. Survival probabilities (the Kaplan-Meier method). BMJ. 1998 Dec. 5; 317(7172):1572.

Yoshida T, Eguchi H, Nakachi K, Tanimoto K, Higashi Y, Suemasu K et al (2000). Distinct mechanisms of loss of estrogen receptor alpha gene expression in human breast cancer: methylation of the gene and alteration of trans-acting factors. *Carcinogenesis* 21: 2193-201.

Zhao H, Langerod A, Ji Y, Nowels K W, Nesland J M, Tibshirani R et al (2004). Different gene expression patterns in invasive lobular and ductal carcinomas of the breast. *Mol Biol Cell* 15: 2523-36.

Zhao J J, Lin J, Yang H, Kong W, He L, Ma X et al (2008). MicroRNA-221/222 negatively regulates estrogen receptor alpha and is associated with tamoxifen resistance in breast cancer. *J Biol Chem* 283: 31079-86.

What is claimed is:

1. A method of theranostic classification of a breast cancer tumor, the method comprising:

determining an expression level of FOXC1 in a breast cancer tumor sample, wherein the expression level of FOXC1 is determined by quantitative reverse transcriptase polymerase chain reaction (qRT-PCR), using forward and reverse cDNA primers having the cDNA sequences of SEQ ID NO: 6 and SEQ ID NO: 7, respectively; and classifying the breast cancer tumor sample as a theranostic basal-like breast cancer subtype or a theranostic hybrid basal-like breast cancer tumor subtype when the breast cancer tumor sample is determined to have a high expression level of FOXC1, wherein the high expression level of FOXC1 is above a 90th percentile level of FOXC1 expression levels for a dataset of breast cancer tumors, the dataset comprising all known breast cancer subtypes.

2. The method of claim 1, wherein the breast cancer tumor sample is a formalin-fixed paraffin embedded (FFPE) sample.

* * * * *